US009107933B2

(12) United States Patent
Sacks et al.

(10) Patent No.: US 9,107,933 B2
(45) Date of Patent: Aug. 18, 2015

(54) COMPOSITIONS AND METHODS OF TARGETING APOLIPOPROTEIN B FOR THE REDUCTION OF APOLIPOPROTEIN C-III

(75) Inventors: Frank M. Sacks, Belmont, MA (US); Diane Tribble, Carlsbad, CA (US)

(73) Assignees: Isis Pharmaceuticals, Inc., Carlsbad, CA (US); President and Fellows of Harvard College, Cambridge, MA (US)

( * ) Notice: Subject to any disclaimer, the term of this patent is extended or adjusted under 35 U.S.C. 154(b) by 285 days.

(21) Appl. No.: 13/257,260

(22) PCT Filed: Mar. 16, 2010

(86) PCT No.: PCT/US2010/027541
§ 371 (c)(1),
(2), (4) Date: Feb. 1, 2012

(87) PCT Pub. No.: WO2010/107838
PCT Pub. Date: Sep. 23, 2010

(65) Prior Publication Data
US 2012/0129911 A1    May 24, 2012

Related U.S. Application Data

(60) Provisional application No. 61/160,671, filed on Mar. 16, 2009.

(51) Int. Cl.
*A61K 31/7088*    (2006.01)
(52) U.S. Cl.
CPC .................. *A61K 31/7088* (2013.01)
(58) Field of Classification Search
USPC .................. 435/6, 91.1, 91.31, 455, 458, 6.1; 514/44; 536/23.1, 24.5
See application file for complete search history.

(56) References Cited

U.S. PATENT DOCUMENTS

| 5,220,006 A | 6/1993 | Ross et al. |
|---|---|---|
| 5,434,058 A | 7/1995 | Davidson et al. |
| 5,618,674 A | 4/1997 | Sanchez-Pescador et al. |
| 5,656,612 A | 8/1997 | Monia |
| 5,712,257 A | 1/1998 | Carter |
| 5,786,206 A | 7/1998 | Smith et al. |
| 5,801,154 A | 9/1998 | Baracchini et al. |
| 5,877,009 A | 3/1999 | Zannis et al. |
| 5,945,290 A | 8/1999 | Cowsert |
| 5,998,148 A | 12/1999 | Bennett et al. |
| 6,010,849 A | 1/2000 | Edwards et al. |
| 6,033,910 A | 3/2000 | Monia et al. |
| 6,096,516 A | 8/2000 | Kwak et al. |
| 6,156,315 A | 12/2000 | Goldberg et al. |
| 6,172,216 B1 | 1/2001 | Bennett et al. |
| 6,184,212 B1 | 2/2001 | Miraglia et al. |
| 6,235,470 B1 | 5/2001 | Sidransky |
| 6,300,132 B1 | 10/2001 | Monia et al. |
| 6,500,672 B1 | 12/2002 | Sladek et al. |
| 6,512,161 B1 | 1/2003 | Rouy et al. |
| 6,534,277 B1 | 3/2003 | Hancock et al. |
| 6,582,908 B2 | 6/2003 | Fodor et al. |
| 6,660,737 B2 | 12/2003 | Almstead et al. |
| 6,670,461 B1 | 12/2003 | Wengel et al. |
| 6,852,536 B2 | 2/2005 | Dobie |
| 6,878,729 B2 | 4/2005 | Almstead et al. |
| 6,949,367 B1 | 9/2005 | Dempcy et al. |
| 7,407,943 B2 | 8/2008 | Crooke et al. |
| 7,511,131 B2 * | 3/2009 | Crooke et al. ............... 536/24.5 |
| 7,598,227 B2 | 10/2009 | Crooke et al. |
| 7,750,141 B2 | 7/2010 | Crooke et al. |
| 7,803,930 B2 | 9/2010 | Crooke et al. |
| 7,888,324 B2 | 2/2011 | Crooke et al. |
| 2001/0053519 A1 | 12/2001 | Fodor et al. |
| 2002/0068708 A1 | 6/2002 | Wengel et al. |
| 2002/0123617 A1 | 9/2002 | Starling et al. |
| 2003/0083280 A1 | 5/2003 | Crooke et al. |
| 2003/0087853 A1 | 5/2003 | Crooke et al. |
| 2003/0215943 A1 | 11/2003 | Crooke et al. |
| 2003/0228597 A1 | 12/2003 | Cowsert et al. |
| 2003/0228613 A1 | 12/2003 | Bornarth et al. |
| 2004/0171566 A1 | 9/2004 | Monia et al. |
| 2004/0208856 A1 | 10/2004 | Crooke et al. |
| 2004/0209838 A1 | 10/2004 | Monia et al. |
| 2004/0214325 A1 | 10/2004 | Crooke et al. |
| 2004/0241651 A1 | 12/2004 | Olek et al. |
| 2004/0266714 A1 | 12/2004 | Freier et al. |

(Continued)

FOREIGN PATENT DOCUMENTS

| EP | 0332435 | 9/1989 |
|---|---|---|
| EP | 0530794 | 3/1993 |

(Continued)

OTHER PUBLICATIONS

Chan et al., Metabolism, vol. 51, No. 8, pp. 1041-1046 (2002).*
Kawakami et al., Circulation, vol. 113, pp. 691-700 (2006).*
Agrawal et al., "Antisense therapeutics: is it as simple as complementary base recognition?" Mol. Med. Today (2000) 6:72-81.
Bayarsaihan et al., "Single-strand-DNA-binding factors specifically recognize the pyrimidine element in the chick a2(I) collagen gene promoter" Biochem J. (1996) 314:293-296.
Bennett et al., "Inhibition of endothelial cell adhesion molecule expression with antisense oligonucleotides." Journal of Immunology (1994) 152(7):3530-3540.
Bennett et al., "Antisense Oligonucleotides as a tool for gene functionalization and target validation" Biochimica et Biophysica Acta (1999) vol. 1489:19-30.
Boren et al., "A simple and efficient method for making site-directed mutants, deletions, and fusions of large DNA such as P1 and BAC clones" *Genome Research* (1996) 6:1123-1130.

(Continued)

*Primary Examiner* — Jane Zara
(74) *Attorney, Agent, or Firm* — Isis Pharmaceuticals, Inc. Patent Dept. Grant IP, Inc.

(57) ABSTRACT

Disclosed herein are compositions and methods for lowering Apolipoprotein C-III (ApoC-III) in a subject in need thereof. Subjects in need of ApoC-III reduction include subjects with elevated ApoC-III levels, subjects with a condition associated with ApoC-III, subjects with diabetes, obese subjects and subjects with cardiovascular disease. Compositions to lower ApoC-III include compounds targeting Apolipoprotein B (ApoB) such as Mipomersen and other antisense compound targeting ApoB.

34 Claims, No Drawings

(56) References Cited

U.S. PATENT DOCUMENTS

| | | |
|---|---|---|
| 2005/0009088 A1 | 1/2005 | Crooke et al. |
| 2005/0014713 A1 | 1/2005 | Freier |
| 2005/0043524 A1 | 2/2005 | Bhanot et al. |
| 2005/0130923 A1 | 6/2005 | Bhat et al. |
| 2005/0164271 A1 | 7/2005 | Bhanot et al. |
| 2005/0272680 A1 | 12/2005 | Bhanot et al. |
| 2005/0287558 A1 | 12/2005 | Crooke et al. |
| 2006/0009410 A1 | 1/2006 | Crooke et al. |
| 2006/0025373 A1 | 2/2006 | Bhanot et al. |
| 2006/0035858 A1 | 2/2006 | Geary et al. |
| 2007/0031844 A1 | 2/2007 | Khvorova et al. |
| 2007/0087987 A1 | 4/2007 | Monia et al. |
| 2007/0238688 A1 | 10/2007 | Bhanot et al. |
| 2007/0238689 A1 | 10/2007 | Bhanot et al. |
| 2008/0146788 A1 | 6/2008 | Bhat et al. |
| 2008/0242629 A1 | 10/2008 | Crooke et al. |
| 2009/0306180 A1 | 12/2009 | Bhanot et al. |
| 2009/0326040 A1 | 12/2009 | Geary |

FOREIGN PATENT DOCUMENTS

| | | |
|---|---|---|
| EP | 0911344 | 4/1999 |
| EP | 1239051 | 9/2002 |
| WO | WO 92/10590 | 6/1992 |
| WO | WO 94/13794 | 6/1994 |
| WO | WO 97/20924 | 6/1997 |
| WO | WO 97/35538 | 10/1997 |
| WO | WO 98/20166 | 5/1998 |
| WO | WO 98/32846 | 7/1998 |
| WO | WO 98/36641 | 8/1998 |
| WO | WO 99/14226 | 3/1999 |
| WO | WO 99/18237 | 4/1999 |
| WO | WO 99/18986 | 4/1999 |
| WO | WO 99/35241 | 7/1999 |
| WO | WO 00/00504 | 1/2000 |
| WO | WO 00/56916 | 9/2000 |
| WO | WO 00/56920 | 9/2000 |
| WO | WO 01/12789 | 2/2001 |
| WO | WO 01/30354 | 3/2001 |
| WO | WO 01/30395 | 5/2001 |
| WO | WO 01/52902 | 7/2001 |
| WO | WO 01/72765 | 10/2001 |
| WO | WO 01/77384 | 10/2001 |
| WO | WO 02/26768 | 4/2002 |
| WO | WO 03/011887 | 2/2003 |
| WO | WO 03/074723 | 9/2003 |
| WO | WO 03/097662 | 11/2003 |
| WO | WO 2004/044181 | 5/2004 |
| WO | WO 2004/046160 | 6/2004 |
| WO | WO 2004/077384 | 9/2004 |
| WO | WO 2004/093783 | 11/2004 |
| WO | WO 2005/049621 | 6/2005 |
| WO | WO 2006/020676 | 1/2006 |
| WO | WO 2007/031081 | 3/2007 |
| WO | WO 2007/090071 | 9/2007 |
| WO | WO 2007/131238 | 11/2007 |
| WO | WO 2007/134181 | 11/2007 |
| WO | WO 2007/146511 | 12/2007 |
| WO | WO 2008/118883 | 10/2008 |

OTHER PUBLICATIONS

Bonow, "Primary Prevention of Cardiovascular Disease: A Call to Action" Circulation (2002) 106:3140-3141.

Braasch et al., "Novel Antisense and Peptide Nucleic Acid Strategies for Controlling Gene Expression" Biochem. (2002) 41(14):4503-4510.

Branch et al., "A good antisense molecule is hard to find," *TIBS* (1998) 23:45-50.

Campos et al., "Distinct patterns of lipoproteins with apoB defines by presence of apoE or apoC-III in hypercholesterolemia and hypertriglyceridemia" J. Lipid Res. (2001) 42:1239-1349.

Chan et al., "Apolipoprotein B-100 kinetics in visceral obesity: Associations with plasma apolipoprotein C-III concentration" Metabolism Clinical and Experimental (2002) 51(8):1041-1046.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Chapter 1: Basic Principles of Antisense Therapeutics" *Antisense Research and Applications* (1998) 131:1-50.

Crooke, "Antisense oligonucleotides as therapeutics for hyperlipidaemias" Expert Opinion on Biological Therapy (2005) 5(7):907-917.

Crooke, "Progress in Antisense Technology" Ann. Rev. Med. (2004) 55:61-95.

Cuchel et al., "Inhibition of Microsomal Triglyceride Transfer Protein in Familial Hypercholesterolemia" New England Journal of Medicine (2007) 356:148-156.

Dammerman et al., "An apolipoprotein CII haplotype protective against hypertriglyceridemia is specified by promoter and 3' untranslated region polymorohisms" Proc. Natl. Sci. U. S. A., (1993)90:4562-4566.

Davidson et al., "Apolipoprotein B: mRNA editing, lipoprotein assembly, and presecretory degradation" *Annu. Rev. Nutr.* (2000) 20:169-193.

Davis et al., "Atherosclerosis Is a Liver Disease of the Heart" Arteriscler. Thromb. Vasc. Biol. (2001) 21:887-898.

De Mesmaeker et al., "Backbone modifications in oligonucleotides and peptide nucleic acid systems" *Curr Opin Struct Biol* (1995) 5:343-355.

De Silva et al., "Overexpression of human apolipoprotein C-III in transgenic mice results in an accumulation of apolipoprotein B48 remnants that is corrected by excess apolipoprotein E" J. Biol. Chem. (1994) 269:2324-2335.

DeCatarina et al., "Fatty Acid Modulation of Endothelial Activation" American Journal of Clinical Nutrition (2000) 71(suppl.):213S-223S.

Deeb et al., "Chromosomal localization of the human apolipoprotein B gene and detection of homologous RNA in monkey intestine" *Proc. Natl. Acad. Sci. USA* (1986) 83:419-422.

Deere et al., "Antisense Phosphorodiamidate Morpholino Oligomer Length and Target Position Effects on Gene-Specific Inhibition in *Escherichia coli*" Antimicrobial Agents and Chemotherapy (2005) 49:249-255.

Duivenvoorden et al., "Apolipoprotein C3 Deficiency Results in Diet-Induced Obesity and Aggravated Insulin Resistance in Mice" Diabetes (2005) 54:664-671.

Eggerman et al., "Use of Oligonucleotides to Target Nucleic Acid Sequences Encoding Apolipoprotein B to Decrease Serum Apolipoprotein B and Cholesterol Levels" *Federal Register* (2000) 65:110.

Farese et al., "Knockout of the mouse apolipoprotein B gene results in embryonic lethality in homozygotes and protection against diet-induced hypercholesterolemia in heterozygotes" Proc. Natl. Acad. Sci. USA (1995) 92:1774-1778.

Geary et al., "Pharmacokinetics of a tumor necrosis factor-alpha phosphorothioate 2'-O-(2-methoxyethyl) modified antisense oligonucleotide: comparison across species" Drug Metab. Dispos. (2003) 31:1419-1428.

Heymsfield, "Effects of Weight Loss With Orlistat on Glucose Tolerance and Progression to Type 2 Diabetes in Obese Adults" Archives of Internal Medicine 160:1321-1326.

Iijima et al., "Red Wine Polyphenols Inhibit Vascular Smooth Muscle Cell Migration Through Two Distinct Signaling Pathways" Circulation (2002) 105(20):2404-2410.

Innerarity et al., "Familial defective apolipoprotein B-100: low density lipoproteins with abnormal receptor binding" Proc. Natl. Acad. Sci. USA (1987) 84:6919-6923.

Ito et al., "Hypertriglyceridemia as a result of human apo CIII gene expression in transgenic mice" Science (1990) 249:790-793.

James, "Towards gene-inhibition therapy; a review of progress and prospects in the field of antiviral antisense nucleic acids and ribozymes" Antiviral Chemistry and Chemotherapy (1991) vol. 2, No. 4, pp. 191-214.

Jen et al., "Suppression of Gene Expression by Targeted Disruption of Messenger RNA: Available Options and Current Strategies" *Stem Cells* (2000) 18:307-319.

(56) References Cited

OTHER PUBLICATIONS

Jong et al., "Role of ApoCs in Lipoprotein Metabolism—Functional Differences Between ApoC1, ApoC2, and ApoC3" Arterioscler. Thromb. Vasc. Biol. (1999) 19:472-484.

Jover et al., "Cytochrome P450 regulation by hepatocyte nuclear factor 4 in human hepatocytes: a study using adenovirus-mediated antisense targeting" Hepatology (2001) 33(3):668-675.

Karathanasis "Apolipoprotein multigene family: tandem organization of human apolipoprotein AI, CIII, and AIV genes" Proc. Natl. Acad. Sci. U. S. A. (1985) 82:6374-6378.

Kardassis et al., "Direct physical interactions between HNF-4 and Sp1 mediate synergistic transact vation of the apolipoprotein CIII promoter" Biochemistry (2002) 41:1217-1228.

Kardassis et al., "SMAD proteins transactivate the human ApoCIII promoter by interacting physically and functionally with hepatocyte nuclear factor 4" J. Biol. Chem. (2000) 275:41405-41414.

Kastelein et al., "Potent reduction of apolipoprotein B and low-density lipoprotein cholesterol by short-term administration of an antisense inhibitor of apolipoprotein B" Circulation (2006) 114(16):1729-1735.

Katan et al., "Characteristics of human hypo- and hyperresponders to dietary cholesterol" Am. J. Epidemiol. (1987) 125:387-399.

Kim et al., "Genetically modified mice for the study of apolipoprotein B," J. Lipid Res. (1998) 39:703-723.

Klein et al., "P284: Apoprotein C-III (ApoCIII) Protein Concentrations and Gene Polymorphisms in Type 1 Diabetes" Aretioscler. Thromb. Vasc. Biol. (2002) 22(5):A-50.

Knopp, "Drug Treatment of Lipid Disorders" New Engl J. Med (1999) 341:498-511.

Koba et al., "Small dense LDL phenotype is associated with postprandial increases of large VLDL and remnant-like particles in patients with acute myocardial infarction" Atherosclerosis (2003) 170(1):131-140.

Lai et al., "Association between obesity and hyperlipidemia among children." Yale Journal of Biology and Medicine (2001) 74:205-210.

Latorra et al., "Enhanced allele-specific PCR discrimination in SNP genotyping using 3' locked nucleic acid (LNA) primers," Human Mutation (2003) 22:79-85.

Law et al., "Human apolipoprotein B-100: cloning, analysis of liver mRNA, and assignment of the gene to chromosome 2," Proc. Natl. Acad. Sci. USA (1985) 82:8340-8344.

Lee et al., "LDL Containing Apolipoprotein CIII Is and Independent Risk Factor for Coronary Events in Diabetic Patients" Arteriosclerosis, Thrombosis, and Vascular Biology (2003) 23:853-858.

Levy-Wilson et al., "Isolation and DNA sequence of full-length cDNA for human preapolipoprotein CIII" DNA (1984) 3:359-364.

Li et al., "Common genetic variation in the promoter of the human apo CIII gene abolishes regulation by insulin and may contribute to hypertriglyceridemia" J. Clin. Invest. (1995) 96:2601-2605.

Ma et al., "Synthetic oligonucleotides as therapeutics: the coming age," Biotechnology Annual Review (2000) 5:155-196.

Maeda et al., "Molecular cloning of a human apoC-III variant: Thr 74 - - - Ala 74 mutation prevents O-glycosylation" J. Lipid Res. (1987) 28:1405-1409.

Maeda et al., "Targeted disruption of the apolipoprotein C-III gene in mice results in hypotriglyceridemia and protection from postprandial hypertriglyceridemia" J. Biol. Chem. (1994) 269:23610-23616.

Maxwell et al., "Proprotein Convertase Subtilisin Kexin 9: The Third Locus Implicated in Autosomal Dominant Hypercholesterolemia" Current Opinion in Lipidology (2005) 16:167-172.

McCormick et al., "Transgenic mice expressing human ApoB95 and ApoB97. Evidence that sequences within the carboxyl-terminal portion of human apoB100 are important for the assembly of lipoprotein," J. Biol. Chem. (1997) 272:23616-23622.

Milner et al., "Selecting effective antisense reagents on combinatorial oligonucleotide arrays" Nature Biotechnology (1997) 15:537-541.

New England Biolabs, 1998/1999 Catalog, pp. 121 and 284.

Nielsen, "Systemic Delivery: The Last Hurdle?" Gene Therapy (2005) 12:956-957.

Nishina et al., "Synthetic low and high fat diets for the study of atherosclerosis in the mouse," J. Lipid Res. (1990) 31:859-869.

Nowak-Gottl et al., "Lipoprotein (a): its role in childhood thromboembolism," Pediatrics (1997) 99:1-3.

Ogami et al., "Purification and characterization of a heat stable nuclear factor CIIIB1 involved in the regulation of the human ApoC-III gene" J. Biol. Chem. (1991) 266:9640-9646.

Olivieri et al., "ApoC-III gene polymorphisms and risk of coronary artery disease" J. Lipid Res. (2002) 43:1450-1457.

Olivieri et al., "Apolipoprotein C-III, n-3 Polyunsaturated Fatty Acids, and "Insulin-Resistant" T-455C APOC3 Gene Polymorphism in Heart Disease Patients: Example of Gene-Diet Interaction" Clin. Chem. (2005) 51(2):360-367.

Opalinska et al., "Nucleic-Acid Therapeutics: Basic Principles and Recent Applications" Nature Rev. Drug Discov. (2002) 1:503-514.

Parrish et al., "Functional anatomy of a dsRNA trigger: differential requirement for the two trigger strands in RNA interference," Molecular Cell (2000) 6:1077-1087.

Patil et al., "DNA-based therapeutics and DNA delivery systems: a comprehensive review," AAPS Journal (2005) 7:E61-E77.

Petersen et al., "Locked nucleic acid (LNA) recognition of RNA: NMR solution structures of LNA:RNA hybrids," Journal of the American Chemical Society (2002) 124:5974-5982.

Pittner et al., "Effects of PYY[3-36] in rodent models of diabetes and obesity" Int. J. Obes. Relat. Metab. Disord. (2004) 28:963-971.

Protter et al., "Isolation and sequence analysis of the human apolipoprotein CIII gene and the intergenic region between the apo AI and apo CIII genes" DNA (1984) 3:449-456.

Raspe et al., "Identification of Rev-erbalpha as a physiological repressor of apoC-III gene transcription" J. Lipid Res. (2002) 43:2172-2179.

Reynolds et al., "Rational siRNA design for RNA interference" Nature Biotechnology (2004) 22(3):326-330.

Roglans et al., "Atorvastatin Treatment Induced Peroxisome Proliferator-Activated Receptor Alpha Expression and Decreased Plasma Nonesterified Fatty Acids and Liver Triglyceride in Fructose-Fed Rats" Journal of Pharmacology and Experimental Therapeutics (2002) 302:232-239.

Rojanasakul, "Antisense Oligonucleotide Therapeutics: Drug Delivery and Targeting" Advanced Drug Delivery Reviews (1996) 18:115-131.

Rossi et al., "Introductory Remarks on the General Application of Antisense RNAs and Ribozymes," METHODS: A Companion to Methods in Enzymology (1993) 5:1-5.

Sandkamp et al., "Lipoprotein(a) is an independent risk factor for myocardial infarction at a young age," Clin. Chem. (1990) 36:20-23.

Sanghvi et al., "Heterocyclic Base Modifications in Nucleic Acids and Their Applications in Antisense Oligonucleotides" Antisense Research and Applications (1993) pp. 273-288.

Schoonjans et al., "3-Hydroxy-3-methylglutaryl CoA reductase inhibitors reduce serum triglyceride levels through modulation of apolipoprotein C-III and lipoprotein lipase" FEBS Lett. (1999) 452:160-164.

Seed et al., "Relation of serum lipoprotein(a) concentration and apolipoprotein(a) phenotype to coronary heart disease in patients with familial hypercholesterolemia," N Engl J Med (1990) 322:1494-1498.

Senior, "Antisense inhibitor provides new treatment approach for hypercholesterolaemia" Drug Discovery Today (2002) 7:840-841.

Sewell et al., "Phase I Trial of ISIS 104838, a 2'-Methoxyethyl Modified Antisense Oligonucleotide Targeting Tumor Necrosis Factor-α" Journal of Pharmacology and Experimental Therapeutics (2002) 303:1334-1343.

Shachter "Apolipoproteins C-I and C-III as important modulators of lipoprotein metabolism" Curr. Opin. Lipidol. (2001) 12:297-304.

Sharpe et al., "Human apolipoproteins AI, AII, CII and CIII. cDNA sequences and mRNA abundance" Nucleic Acids Res. (1984) 12:3917-3932.

Simeonov et al., "Single nucleotide polymorphism genotyping using short, fluorescently labeled locked nucleic acid (LNA) probes and fluorescence polarization detection," Nucleic Acids Research (2002) 30:E91.

(56) References Cited

OTHER PUBLICATIONS

Skrapari et al., "Glibenclamide improves postprandial hypertriglyceridaemia in type 2 diabetic patients by reducing chylomicrons but not the very low-density lipoprotein subfraction levels," *Diabet Med* (2001) 18:781-785.

Smith et al., "Rational selection for antisense oligonucleotide sequences" European Journal of Pharmaceutical Sciences (2000) 11(3):191-198.

Tamm et al., "Antisense therapy in oncology: new hope for an old idea?" The Lancet (2001) 358:489-497.

Tanaka et al., "Regulation of apolipoprotein B production and secretion in response to the change of intracellular cholesteryl ester contents in rabbit hepatocytes," *Journal of Biological Chemistry* (1993) 268:12713-12718.

Tang et al., "The Inhibition of Antisense Oligodeoxynucleotides on the Expression of Apolipoprotein B in Rat Liver Cells," *Zhongguo Dongmai Yinghua ZaZhi Bianjibu (Chinese Journal)* (1999) 7:315-318.

Ugawa et al., "YM-53601, a novel squalene synthase inhibitor, suppresses lipgenic biosynthesis and lipid secretion in rodents" British Journal of Pharmacology (2003) 139:140-146.

Veniant et al., "Susceptibility to atherosclerosis in mice expressing exclusively apolipoprotein B48 or apolipoprotein B100," *J. Clin. Invest.* (1997) 100:180-188.

Vessby et al., "Diverging effects of cholestyramine on apolipoprotein B and lipoprotein Lp(a). A dose-response study of the effects of cholestyramine in hypercholesterolaemia," *Atherosclerosis* (1982) 44:61-71.

Vu-Dac et al., "Retinoids increase human apo C-III expression at the transcriptional level via the retinoid X receptor. Contribution to the hypertriglyceridemic action of retinoids." J. Clin. Invest. (1998) 102:625-632.

Wimberly, "Rosuvastatin (Crestor) A new statin for the treatment of dyslipidemia" PharmaNote (2003) 19:1-6.

Woolf et al., "Specificity of antisense oligonucleotides in vivo" PNAS (1992) 89:7305-7309.

Yamamoto et al., "Overexpression of PACAP in Transgenic Mouse Pancreatic B-Cells Enhances Insulin Secretion and Ameliorates Streptozotocin-induced Diabetes" Diabetes (2003) 52:1155-1162.

Yu et al., "Antisense oligonucleotide reduction of DGAT expression improves hepatic steatosis and hyperlipidemia in obese mice" Hepatology (2005) 42(2):362-371.

Yu et al., "Pharmacokinetics and Pharmacodynamics of an Antisesne Phosphoroth oate Oligonucleotide Targeting Fas mRNA in Mice" J. Pharmacol. Exp. Ther. (2001) 296:388-395.

International Search Report for application PCT/US10/27541 dated May 25, 2010.

Merki et al., "A second generation antisense oligonucleotide directed to human apolipoprotein B-100 reduces lipoprotein(a) levels and oxidized phospholipids on apolipoprotein B-100 particles in lipoprotein(a)-transgenic mice" Journal of the American College of Cardiology (2008) 51(10) Suppl. 1, p. A294.

"Isis 301012" retrieved from the Internet: URL: http://integyity.thomson-pharma.com/integyity/xmlxsl/pk_ref_list.xml_show_ficha_ref?p_ref_id=1132978 [retrieved on Nov. 29, 2012].

European Search Report for application EP 10754009.8 dated Dec. 19, 2012.

Fluiter et al., "On the in vitro and in vivo properties of four locked nucleic acid nucleotides incorporated into an anti-h-ras antisense oligonucleotide" Chembiochem—A European Journal of Chemical Biology (2005) 6(6):1104-1109.

Frieden et al., "Expanding the design horizon of antisense oligonucleotides with alpha-L-LNA" Nucleic Acids Research, Oxford University Press, Surrey, GB, (2003) 31(21):6365-6372.

Funatsu et al., "Reduction in hepatic non-esterified fatty acid concentration after long-term treatment with atorvastatin lowers hepatic triglyceride synthesis and its secretion in sucrose-fed rats" Biochimica et Biophysica Acta (2002) 1580:161-170.

Ganji et al., "Niacin and cholesterol: role in cardiovascular disease (Review)" The Journal of Nutritional Biochemistry (2003) 14:293-305.

Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.

Geary et al., "Pharmacokinetics of a tumor necrosis factor-alpha phosphorothioate 2'-O-(2-methoxyethyl) modified antisense oligonucleotide: comparison across species" Drug Metab. Dispos. (2003) 31:1417-1428.

Gewirtz et al., "Facilitating oligonucleotide delivery: Helping antisense deliver on its promise" PNAS USA (1996) 93:3161-3163.

Graham et al., "Inhibition of ApoB-100 as a Therapeutic Strategy for the Treatment of Hyperlipidemias" *AHA Abstracts* (2002) Abstract ID:20009.

Hajjar et al., "The role of lipoprotein(a) in atherogenesis and thrombosis" *Annu. Rev. Med.* (1996) 47:423-442.

Hammond et al., "Post-transcriptional gene silencing by double-stranded RNA" *Nature Reviews Genetics* (2001) 2:110-119.

Hertz et al., "Mode of action of peroxisome proliferators as hypolipidemic drugs. Suppression of apolipoprotein C-III" J. Biol. Chem. (1995) 270:13470-13475.

Heymsfield, "Effects of Weight Loss With Orlistat on Glucose Tolerance and Progression to Type 2 Diabetes in Obese Adults" Archives of Internal Medicine 160:1321-1326, (2000).

Huang et al., "Hypobetalipoproteinemia due to an apolipoprotein B gene exon 21 deletion derived by Alu-Alu recombination" *Journal of Biological Chemistry* (1989) 264:11394-11400. (Genbank NM_000384).

Burnett, "Drug evaluation: ISIS-301012, an antisense oligonucleotide for the treatment of hypercholesterolemia" Current Opinion in Molecular Therapeutics (2006) 8(5):461-467.

Elias et al., "Decreased Production Rates of VLDL Triglycerides and ApoB-100 in Subjects Heterozygous for Familial Hypobetalipoproteinemia" Metabolism of Triglycerides and ApoB-100 in FHBL, Arterioscler. Thromb. Vasc. Biol. (1999) 9:2714-2721.

Lemonidis et al., "Abstracts of the 11th International Congress on Cardiovascular Pharmacotherapy. Montreal, Canada, May 18-21, 2002" Cardiovascular Drugs and Therapy/Sponsored by the International Society of Cardiovascular Pharmacotherapy (2002) 16(1):P471.

PR Newswire, "Isis Pharmaceuticals initiates phase I study of second-generation antisense drug for cardiovascular disease" New York, Dec. 29, 2003.

PR Newswire, "Second-generation antisense drug for cardiovascular disease demonstrates significant and durable reductions in cholesterol" Aug. 11, 2004.

Rosenson, "Clinical Role of LDL and HDL Subclasses and Apolipoprotein Measurements" ACC Current Journal Review (2004) 33-37.

Rubies-Prat et al., "Low-density lipoprotein particle size, triglyceride-rich lipoproteins, and glucose tolerance in non-diabetic men with essential hypertension" Clinical and Experimental Hypertension (2001) 23:489-500.

Sniderman et al., "Substrate Delivery as a Determinant of Hepatic ApoB Secretion" Arterioscler. Thromb. Vasc. Biol. (1993) 13:629-636.

Zhengming et al., "Serum cholesterol concentration and coronary heart disease in population with low cholesterol concentrations" BMJ. (1991) 303:276-282.

\* cited by examiner

COMPOSITIONS AND METHODS OF TARGETING APOLIPOPROTEIN B FOR THE REDUCTION OF APOLIPOPROTEIN C-III

CROSS REFERENCED TO RELATED APPLICATIONS

This application is a U.S. National Phase filing under 35 U.S.C. §371 claiming priority to International Serial No. PCT/US2010/027541 filed Mar. 16, 2010, which claims priority to U.S. Provisional Application 61/160,671, filed Mar. 16, 2009, each of which is incorporated herein by reference in its entirety.

FIELD OF THE INVENTION

The present invention provides compositions and methods for lowering plasma Apolipoprotein C-III (ApoC-III) and ApoC-III in lipoproteins. More specifically, the invention relates to compositions and methods of targeting Apolipoprotein B (ApoB) for reducing ApoC-III.

SEQUENCE LISTING

The present application is being filed along with a Sequence Listing in electronic format. The Sequence Listing is provided as a file entitled BIOL0110USASEQ.TXT, created Sep. 12, 2011, which is 124 Kb in size. The information in the electronic format of the sequence listing is incorporated herein by reference in its entirety.

BACKGROUND OF THE INVENTION

Coronary heart disease (CHD) has been the leading cause of death in the United States for over a century, and complications from atherosclerosis are the most common causes of death in Western societies (Knopp, *New Engl. J. Medicine*, 1999, 341, 498-511; Davis and Hui, *Arterioscler. Thromb. Vasc. Biol.*, 2001, 21, 887-898; Bonow, *Circulation*, 2002, 106, 3140-3141). Elevated low density lipoprotein-cholesterol (LDL-C) is widely recognized as a risk factor for CHD and lowering of LDL-C is highly recommended. However, despite pharmacologic intervention, many individuals are unable to lower LDL-C levels.

Low density lipoproteins (LDL) are one of five broad classes of lipoproteins, which include the following: chylomicrons, responsible for the transport dietary lipids from intestine to tissues; very low density lipoproteins (VLDL); intermediate density lipoproteins (IDL); low density lipoproteins (LDL); all of which transport triacylglycerols and cholesterol from the liver to tissues; and high density lipoproteins (HDL), which transport endogenous cholesterol from tissues to the liver. Lipoprotein particles undergo continuous metabolic processing and have variable properties and compositions. The protein components of lipoproteins are known as apolipoproteins. At least nine apolipoproteins, such as Apolipoprotein B (also known as ApoB, apolipoprotein B-100, ApoB-100, apolipoprotein B-48, ApoB-48 and Ag(x) antigen) and Apolipoprotein C-III (ApoC-III), are distributed in significant amounts among the various human lipoproteins.

ApoB performs a variety of functions, including the absorption and processing of dietary lipids, as well as the regulation of circulating lipoprotein levels (Davidson and Shelness, *Annu. Rev. Nutr.*, 2000, 20, 169-193). Two forms of apolipoprotein B exist in mammals: ApoB-100 and ApoB-48.

ApoC-III is thought to delay catabolism and clearance of triglyceride-rich particles such as VLDL and LDL. Increased ApoC-III levels can induce development of hypertriglyceridemia and ApoC-III concentrations in VLDL and LDL are associated with coronary heart disease (Campos et al., Distinct patterns of lipoproteins with apoB defined by presence of apoE or apoC-III in hypercholesterolemia and hypertriglyceridemia. *J. Lipid Res.* 2001, 42:1239-1249).

Mipomersen (ISIS 301012), and other second-generation antisense oligonucleotides targeting ApoB-100, have been shown to reduce hepatic production of ApoB. Mipomersen is currently undergoing clinical studies to determine whether it is effective in decreasing LDL-C and triglycerides in specific populations. Although the effect of Mipomersen on ApoB has been studied in detail, its effect, if any, on ApoC-III was unknown.

SUMMARY OF THE INVENTION

Provided herein are compounds useful for modulating gene expression and associated pathways via antisense mechanisms of action such as RNaseH, RNAi and dsRNA enzymes, as well as other mechanisms based on target degradation or target occupancy.

Provided herein are methods, compounds, and compositions for inhibiting or reducing expression of ApoC-III levels in a human subject.

Provided herein are methods of lowering plasma ApoC-III levels in a human subject, comprising: a) selecting a human subject with elevated ApoC-III levels or a condition associated with ApoC-III; and b) administering to the human subject a therapeutically effective amount of a compound comprising a modified oligonucleotide having 12-30 linked nucleosides, or a salt thereof, wherein said modified oligonucleotide is 100% complementary to a nucleic acid encoding human ApoB. The administration of the modified oligonucleotide targeting ApoB reduces plasma ApoC-III levels in the human subject.

A method for treating, reducing the incidence of, or ameliorating a symptom of coronary heart disease in a diabetic subject, comprising: a) selecting a human subject with diabetes having or at risk of having coronary heart disease; and b) administering to the human subject a therapeutically effective amount of a compound comprising a modified oligonucleotide having 12-30 linked nucleosides, or a salt thereof, wherein the modified oligonucleotide is 100% complementary to a nucleic acid encoding human apolipoprotein B. The administration of the modified oligonucleotide targeting ApoB reduces plasma ApoC-III levels in the diabetic human subject.

Provided herein are methods for treating, reducing the incidence of, or ameliorating a symptom of coronary heart disease in an obese subject, comprising: a) selecting an obese human subject having or at risk of having coronary heart disease; and b) administering to the obese human subject a therapeutically effective amount of a compound comprising a modified oligonucleotide having 12-30 linked nucleosides, or a salt thereof, wherein the modified oligonucleotide is 100% complementary to a nucleic acid encoding human apolipoprotein B. The administration of the modified oligonucleotide targeting ApoB reduces plasma ApoC-III levels in the obese human subject.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference in their entirety.

Unless otherwise indicated, the following terms have the following meanings:

"2'-O-methoxyethyl" (also 2'-MOE and 2'-O(CH2)2-OCH3) refers to an O-methoxy-ethyl modification of the 2' position of a furosyl ring. A 2'-O-methoxyethyl modified sugar is a modified sugar.

"2'-O-methoxyethyl nucleoside" means a nucleoside comprising a 2'-O-methoxyethyl modified sugar moiety.

"5-methylcytosine" means a cytosine modified with a methyl group attached to the 5' position. A 5-methylcytosine is a modified nucleobase.

A subject is "at risk" of developing a particular condition or disorder when that subject exhibits one or more signs or symptoms recognized by one skilled in the art as associated with the condition or disorder. For example, a subject is "at risk" for developing coronary heart disease when the subject exhibits, e.g., elevated LDL cholesterol.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration.

"Administering" means providing a pharmaceutical agent to an individual, and includes, but is not limited to administering by a medical professional and self-administering.

"Antisense compound" means an oligomeric compound that is capable of undergoing hybridization to a target nucleic acid through hydrogen bonding.

"Antisense inhibition" means reduction of target nucleic acid levels in the presence of an antisense compound complementary to a target nucleic acid compared to target nucleic acid levels in the absence of the antisense compound.

"Bicyclic sugar" means a furosyl ring modified by the bridging of two non-geminal ring atoms. A bicyclic sugar is a modified sugar moiety.

"Cardiovascular disease" or "cardiovascular disorder" refers to a group of conditions related to the heart, blood vessels, or the circulation. Examples of cardiovascular diseases include, but are not limited to, aneurysm, angina, arrhythmia, atherosclerosis, cerebrovascular disease (stroke), coronary heart disease, and hypertension.

"Chimeric antisense compounds" means antisense compounds that have at least 2 chemically distinct regions, each region having a plurality of subunits, for example, nucleosides.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-esterified cholesterol present in the plasma or serum.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Complementarity" means the capacity for pairing between nucleobases of a first nucleic acid and a second nucleic acid.

"Comprise," "comprises" and "comprising" will be understood to imply the inclusion of a stated step or element or group of steps or elements but not the exclusion of any other step or element or group of steps or elements.

A "condition associated with elevated apolipoprotein C-III" refers to a disorder or condition afflicting a human subject that results from or manifests as elevated plasma apolipoprotein C-III concentrations. In certain embodiments, such apolipoprotein C-III concentrations are measured in particular lipoprotein, e.g., VLDL-C, LDL-C, IDL-C, and/or HDL-C.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive glucose in the urine (glycosuria), excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy. "Type 2 diabetes," (also known as "type 2 diabetes mellitus" or "diabetes mellitus, type 2", and formerly called "diabetes mellitus type II", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Diabetic dyslipidemia" or "Type II diabetes with dyslipidemia" means a condition characterized by Type II diabetes, reduced HDL, elevated serum triglycerides, and elevated small, dense LDL particles.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual. In other embodiments, the pharmaceutical agent is administered by infusion over an extended period of time or continuously. Doses may be stated as the amount of pharmaceutical agent per hour, day, week or month.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dyslipidemia" refers to a disorder of lipid and/or lipoprotein metabolism, including lipid and/or lipoprotein overproduction or deficiency. Dyslipidemia may be manifested by elevation of lipids such as cholesterol and triglycerides as well as lipoproteins such as low-density lipoprotein (LDL) cholesterol.

"Elevated apolipoprotein C-III" means a concentration of apolipoprotein C-III in a subject at which apolipoprotein C-III-lowering therapy is recommended. In certain embodiments, apolipoprotein C-III can be measured in particular lipoprotein, e.g., LDL-C, VLDL-C, IDL-C and/or HDL-C.

"Elevated total cholesterol" means total cholesterol at a concentration in an individual at which lipid-lowering therapy is recommended, and includes, without limitation, "elevated LDL-C", "elevated VLDL-C," "elevated IDL-C" and "elevated non-HDL-C." In certain embodiments, total cholesterol concentrations of less than 200 mg/dL, 200-239 mg/dL, and greater than 240 mg/dL are considered desirable, borderline high, and high, respectively. In certain embodiments, LDL-C concentrations of 100 mg/dL, 100-129 mg/dL, 130-159 mg/dL, 160-189 mg/dL, and greater than 190 mg/dL are considered optimal, near optimal/above optimal, borderline high, high, and very high, respectively.

"Elevated lipoprotein" means a concentration of lipoprotein in a subject at which lipid-lowering therapy is recommended.

"Elevated triglyceride" means a concentration of triglyceride in the serum or liver at which lipid-lowering therapy is recommended, and includes "elevated serum triglyceride" and "elevated liver triglyceride." In certain embodiments, triglyceride concentration of 150-199 mg/dL, 200-499 mg/dL, and greater than or equal to 500 mg/dL is considered borderline high, high, and very high, respectively.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid. In certain such embodiments, an antisense oligonucleotide is a first nucleic acid and a target nucleic acid is a second nucleic acid.

"Gapmer" means an antisense compound in which an internal region having a plurality of nucleotides that supports RNaseH cleavage is positioned between external regions having one or more nucleotides that are chemically distinct from the nucleosides of the internal region. A "gap segment" means the plurality of nucleotides that make up the internal region of a gapmer. A "wing segment" means the external region of a gapmer.

"Gap-widened" means an antisense compound which has a gap segment of 12 or more contiguous 2'-deoxyribonucleotides positioned between and immediately adjacent to 5' and 3' wing segments having from one to six nucleotides having modified sugar moieties.

"High density lipoprotein-C (HDL-C)" means cholesterol associated with high density lipoprotein particles. Concentration of HDL-C in serum (or plasma) is typically quantified in mg/dL or nmol/L. "Serum HDL-C" and "plasma HDL-C" mean HDL-C in the serum and plasma, respectively.

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins and triglycerides.

"Hypertriglyceridemia" means a condition characterized by elevated triglyceride levels.

"Improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

"Internucleoside linkage" refers to the chemical bond between nucleosides.

"Intravenous administration" means administration into a vein.

"Linked nucleosides" means adjacent nucleosides which are bonded together.

"Lipoprotein", such as VLDL, LDL and HDL, refers to a group of proteins found in the serum, plasma and lymph and are important for lipid transport. The chemical composition of each lipoprotein differs, for example, in that the HDL has a higher proportion of protein versus lipid, whereas the VLDL has a lower proportion of protein versus lipid.

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Mixed dyslipidemia" means a condition characterized by elevated serum cholesterol and elevated serum triglycerides.

"Modified internucleoside linkage" refers to a substitution and/or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified oligonucleotide" means an oligonucleotide comprising a modified internucleoside linkage, a modified sugar, and/or a modified nucleobase. A modified oligonucleotide can also have a nucleoside mimetic or nucleotide mimetic.

"Modified sugar" refers to a substitution and/or any change from a natural sugar.

"Motif" means the pattern of unmodified and modified nucleosides in an antisense compound.

"Naturally occurring internucleoside linkage" means a 3' to 5' phosphodiester linkage.

"Natural sugar" means a sugar found in DNA (2'-H) or RNA (2'-OH).

"Nucleobase" means a heterocyclic moiety capable of pairing with a base of another nucleic acid.

"Nucleobase sequence" means the order of contiguous nucleobases independent of any sugar, linkage, and/or nucleobase modification.

"Nucleoside" means a nucleobase linked to a sugar.

"Nucleotide" means a nucleoside having a phosphate group covalently linked to the sugar portion of the nucleoside.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Obese" and "obesity" refers to a condition affecting a subject or conditions having a body mass index (BMI) of 30 kg/m² or higher. In one embodiment, an obese subject includes those having a BMI of between about 25 kg/m² and about 30 kg/m².

"Oligomeric compound" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration," means administration through injection or infusion. Parenteral administration includes, but is not limited to, subcutaneous administration, intravenous administration, or intramuscular administration.

"Pharmaceutically acceptable carrier" means a medium or diluent that does not interfere with the structure or the function of the oligonucleotide. Certain of such carriers enable pharmaceutical compositions to be formulated as, for example, tablets, pills, dragees, capsules, liquids, gels, syrups, slurries, suspension and lozenges for the oral ingestion by a subject. For example, a pharmaceutically acceptable carrier can be a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Pharmaceutical composition" or "composition" means a mixture of substances suitable for administering to an individual. For example, a composition may comprise one or more antisense oligonucleotides and a sterile aqueous solution.

"Phosphorothioate internucleoside linkage" or "phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prodrug" means a therapeutic agent that is prepared in an inactive form that is converted to an active form (i.e., drug) within the body or cells thereof by the action of endogenous enzymes or other chemicals and/or conditions.

"Subcutaneous administration" means administration just below the skin.

The term "sugar surrogate" overlaps with the slightly broader term "nucleoside mimetic" but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Targeted" or "targeted to" means having a nucleobase sequence that will allow specific hybridization of an antisense compound to a target nucleic acid to induce a desired effect.

"Target nucleic acid," "target RNA," "target RNA transcript" and "nucleic acid target" all mean a nucleic acid capable of being targeted by antisense compounds.

"Therapeutically effective amount" or "effective amount" means an amount of a pharmaceutical agent that provides a therapeutic benefit to an individual. "Effective amount" in the context of modulating an activity or of treating or preventing a condition means the administration of that amount of active ingredient to a subject in need of such inhibition, treatment or prophylaxis, either in a single dose or as part of a series, that is effective for inhibition of that effect, or for treatment or prophylaxis or improvement of that condition. The effective amount will vary depending upon the health and physical condition of the subject to be treated, the taxonomic group of subjects to be treated, the formulation of the composition, the assessment of the medical situation, and other relevant factors.

"Total cholesterol" means all types of cholesterol, including, but not limited to, LDL-C, HDL-C, IDL-C and VLDL-C. Concentration of total cholesterol in serum (or plasma) is typically quantified in mg/dL or nmol/L.

"Treat" refers to administering a pharmaceutical composition to effect an alteration or improvement of a disease, disorder, or condition.

"Triglycerides" means lipids that are the triesters of glycerol. "Serum triglycerides" or "plasma triglycerides" means triglycerides present in serum or plasma, respectively. "Liver triglycerides" mean triglycerides present in liver tissue.

"Unmodified nucleotide" means a nucleotide composed of naturally occurring nucleobases, sugar moieties and internucleoside linkages. In certain embodiments, an unmodified nucleotide is an RNA nucleotide (i.e., β-D-ribonucleosides) or a DNA nucleotide (i.e., β-D-deoxyribonucleoside).

"Very low density lipoprotein-cholesterol (VLDL-C)" means cholesterol associated with very low density lipoprotein particles. Concentration of VLDL-C in serum (or plasma) is typically quantified in mg/dL or nmol/L. "Serum VLDL-C" and "plasma VLDL-C" mean VLDL-C in the serum or plasma, respectively.

Certain Embodiments

In certain aspects, provided herein are compositions and methods for reduction of apolipoprotein C-III concentrations in human subjects. In certain embodiments, provided herein are compounds for use in treatment of conditions associated with apolipoprotein C-III. Thus, in certain embodiments provided herein is a compound comprising a modified oligonucleotide having 12-30 linked nucleosides, wherein said modified oligonucleotide is 100% complementary to a nucleic acid encoding human apolipoprotein B, for treatment of a condition associated with apolipoprotein C-III. In certain embodiments, said treatment is of a human subject with elevated apolipoprotein C-III concentrations. In certain embodiments, treatment of said human subject results in a decrease in plasma apolipoprotein C-III concentrations in said human subject.

In certain embodiments, the condition associated with apolipoprotein C-III is hyperlipidemia, hypertriglyceridemia, hypercholesterolemia, elevated total cholesterol, elevated LDL-C, elevated VLDL-C, elevated IDL-C, elevated lipoprotein concentrations (including apolipoprotein A-I, apolipoprotein A-II, apolipoprotein A-IV, apolipoprotein A-V, apolipoprotein B, apolipoprotein B100, apolipoprotein C-I, apolipoprotein C-II, apolipoprotein C-III, apolipoprotein C-IV, apolipoprotein D, apolipoprotein E, and/or apolipoprotein H; in certain embodiments the condition is not associated with any one or more of elevated apolipoprotein A-I, apolipoprotein A-II, apolipoprotein A-IV, apolipoprotein A-V, apolipoprotein B, apolipoprotein B100, apolipoprotein C-I, apolipoprotein C-II, apolipoprotein C-III, apolipoprotein C-IV, apolipoprotein D, apolipoprotein E, and/or apolipoprotein H), elevated plasma glucose concentrations, elevated plasma triglyceride concentrations, elevated liver triglyceride concentrations, or hepatic steatosis.

In certain embodiments, provided herein is a compound comprising a modified oligonucleotide having 12-30 linked nucleosides, wherein said modified oligonucleotide is 100% complementary to a nucleic acid encoding human apolipoprotein B, for use in the reduction of apolipoprotein C-III concentrations in a human subject in need of such reduction. In certain embodiments, said human subject is a human subject with elevated apolipoprotein C-III concentrations. In certain embodiments, the human subject does not have elevated plasma apolipoprotein B concentrations.

In a particular embodiment, provided is a compound comprising a modified oligonucleotide having 12-30 linked nucleosides, wherein said modified oligonucleotide is 100% complementary to a nucleic acid encoding human apolipoprotein B, for treatment of hepatic steatosis. In another particular embodiment, provided is a compound comprising a modified oligonucleotide having 12-30 linked nucleosides, wherein said modified oligonucleotide is 100% complementary to a nucleic acid encoding human apolipoprotein B, for reduction of liver triglyceride concentrations.

In another aspect, provided herein are compositions and methods for the manufacture of a medicament for reduction of apolipoprotein C-III concentrations in human subjects. In certain embodiments, provided herein are compounds for the manufacture of a medicament for treatment of conditions associated with apolipoprotein C-III. Thus, in certain embodiments provided herein is a compound comprising a modified oligonucleotide having 12-30 linked nucleosides, wherein said modified oligonucleotide is 100% complementary to a nucleic acid encoding human apolipoprotein B, for the manufacture of a medicament for treatment of a condition associated with apolipoprotein C-III. In certain embodiments, said treatment is of a human subject with elevated apolipoprotein C-III concentrations. In certain embodiments, treatment of said human subject results in a decrease in plasma apolipoprotein C-III concentrations in said human subject.

In certain embodiments, the condition associated with apolipoprotein C-III is hyperlipidemia, hypertriglyceridemia, hypercholesteremia, elevated total cholesterol, elevated lipoprotein concentrations (including apolipoprotein A-I, apolipoprotein A-II, apolipoprotein A-IV, apolipoprotein A-V, apolipoprotein B, apolipoprotein B100, apolipoprotein C-I, apolipoprotein C-II, apolipoprotein C-III, apolipoprotein C-IV, apolipoprotein D, apolipoprotein E, and/or apolipoprotein H; in certain embodiments the condition is not associated with any one or more of elevated apolipoprotein A-I, apolipoprotein A-II, apolipoprotein A-IV, apolipoprotein A-V, apolipoprotein B, apolipoprotein B100, apolipoprotein C-I, apolipoprotein C-II, apolipoprotein C-III, apolipoprotein C-IV, apolipoprotein D, apolipoprotein E, and/or apolipoprotein H), elevated plasma glucose concentrations, elevated plasma triglycerides, elevated liver triglycerides, or hepatic steatosis.

In a particular embodiment, provided is a compound comprising a modified oligonucleotide having 12-30 linked nucleosides, wherein said modified oligonucleotide is 100% complementary to a nucleic acid encoding human apolipoprotein B, for the manufacture of a medicament for treatment of hepatic steatosis. In another particular embodiment, provided is a compound comprising a modified oligonucleotide having 12-30 linked nucleosides, wherein said modified oligonucleotide is 100% complementary to a nucleic acid encoding human apolipoprotein B, for the manufacture of a medicament for reduction of liver triglyceride concentrations.

In certain embodiments, provided herein is a compound comprising a modified oligonucleotide having 12-30 linked nucleosides, wherein said modified oligonucleotide is 100% complementary to a nucleic acid encoding human apolipoprotein B, for the manufacture of a medicament for the reduction of apolipoprotein C-III concentrations in a human subject in need of such reduction. In certain embodiments, said human subject is a human subject with elevated apolipoprotein C-III concentrations. In certain embodiments, the human subject does not have elevated plasma apolipoprotein B concentrations.

In certain embodiments, the modified oligonucleotide has a nucleobase sequence comprising at least an 8 nucleobase portion of SEQ ID NO:10. In certain embodiments, the modified oligonucleotide has a nucleobase sequence comprising at least a 12 nucleobase portion of SEQ ID NO:10. In certain embodiments, the modified oligonucleotide has a nucleobase sequence comprising SEQ ID NO:10. In certain embodiments, the modified oligonucleotide has a nucleobase sequence consisting of SEQ ID NO:10.

In certain embodiments, the antisense oligonucleotide comprises at least one modified internucleoside linkage. In certain embodiments, the modified internucleoside linkage is a phosphorothioate internucleoside linkage.

In certain embodiments, the modified oligonucleotide comprises at least one modified sugar moiety. In certain embodiments, the modified sugar moiety is a 2'-O-methoxyethyl sugar moiety. In certain embodiments, the modified sugar moiety is a bicyclic sugar moiety. In certain embodiments, the bicyclic sugar moiety comprises a 4'-$CH_2$—O-2' bridge. In certain embodiments, the modified sugar moiety comprises a 2'-O-methoxyethyl group.

In certain embodiments, the modified oligonucleotide comprises at least one nucleoside mimetic. In certain embodiments, the nucleoside mimetic is a tetrahydropyran nucleoside wherein a tetrahydropyran ring replaces the furanose ring.

In certain embodiments, the modified oligonucleotides comprises at least one modified nucleobase. In certain embodiments, the modified nucleobase is a 5-methylcytosine.

In certain embodiments, the modified oligonucleotide is a chimeric oligonucleotide having a plurality of 2'-deoxyribonucleosides flanked on each side by at least one modified nucleoside. In certain embodiments, the modified oligonucleotide consists of 20 linked nucleosides and, wherein nucleosides 1-5 and 16-20 are 2'-O-methoxyethyl nucleosides, nucleosides 6-15 are 2'-deoxyribonucleosides and each internucleoside linkage is a phosphorothioate internucleoside linkage.

In certain embodiments, the compound comprises the salt of the modified oligonucleotide. In certain embodiments, the compound comprises the sodium salt of the modified oligonucleotide.

In certain embodiments, the compound is formulated as a composition comprising a pharmaceutically acceptable excipient, vehicle, carrier or diluent.

In certain embodiments, a therapeutically effective amount is delivered in one or a plurality of doses of the compound.

In certain embodiments, the plurality of doses results in a plasma trough concentration of the compound from about 12 ng/mL to about 40 ng/mL or 18 ng/mL to about 40 ng/mL in the plasma of the human subject. In certain embodiments, the plurality of doses results in a plasma trough AUC of the compound from about 12 µg·hr/mL to about 20 µg·hr/mL or 12 µg·hr/mL to about 60 µg·hr/mL in the plasma of the human subject.

In certain embodiments, the compound is mipomersen.

In certain embodiments, each of the plurality of doses is at least about 100 mg or 200 mg of mipomersen. In certain embodiments, each of the plurality of doses is about 200 mg to about 400 mg of mipomersen. In certain embodiments, each of the plurality of doses is about 100 mg, 200 mg, about 300 mg, or about 400 mg of mipomersen In certain embodiments, at least one dose of said plurality of doses is administered about twice a week. In certain embodiments, at least one dose of said plurality of doses is administered about once a week. In certain embodiments, at least one dose of said plurality of doses is administered about once every other week. In certain embodiments, at least one dose of said plurality of doses is administered about once a month.

In certain embodiments, the reduction of plasma apolipoprotein C-III levels depends on the dose of the compound administered to the subject. In certain embodiments, the plasma apolipoprotein C-III levels are reduced at least about 10% relative to the amount of plasma apolipoprotein C-III observed in the subject prior to administration of the compound. In certain embodiments, the plasma apolipoprotein C-III levels are reduced at least about 20% relative to the amount of plasma apolipoprotein C-III observed in the subject prior to administration of the compound. In certain embodiments, the plasma apolipoprotein C-III levels are reduced at least about 30% relative to the amount of plasma apolipoprotein C-III observed in the subject prior to administration of the compound. In certain embodiments, the plasma apolipoprotein C-III levels are reduced at least about 40% relative to the amount of plasma apolipoprotein C-III observed in the subject prior to administration of the compound. In certain embodiments, the plasma apolipoprotein C-III levels are reduced at least about 50% relative to the amount of plasma apolipoprotein C-III observed in the subject prior to administration of the compound. In certain embodiments, the plasma apolipoprotein C-III levels are reduced at least about 54% relative to the amount of plasma apolipoprotein C-III observed in the subject prior to administration of the compound. In certain embodiments, the plasma apolipoprotein C-III levels are reduced at least about 60% relative to the amount of plasma apolipoprotein C-III observed in the subject prior to administration of the compound. In certain embodiments, the plasma apolipoprotein C-III levels are reduced at least about 62% relative to the amount of plasma apolipoprotein C-III observed in the subject prior to administration of the compound.

Certain Indications

Surprisingly, antisense inhibition of ApoB is shown herein to reduce plasma concentrations of ApoC-III and ApoC-III-containing lipoproteins in a dose-dependent manner. More specifically, a reduction is achieved in apoC-III concentration in total plasma, VLDL and suggestively in HDL. The new finding that antisense reduction of ApoB decreases ApoC-III is relevant to certain treatment indications.

Patients with non-insulin-dependent diabetes (NIDDM) have 2 to 3 times higher the risk of coronary heart disease (CHD) than nondiabetic patients. Plasma cholesterol, LDL cholesterol, and HDL cholesterol (HDL-C) are strong risk factors for CHD in NIDDM. Diabetic patients also have higher plasma triglyceride concentrations than nondiabetic patients. The metabolism of triglyceride-rich lipoproteins, chylomicrons, and some types of VLDL and LDL is also abnormal in NIDDM. The production of triglyceride and VLDL by the liver is elevated, and the activity of lipoprotein lipase, which metabolizes triglyceride in VLDL, is decreased (Lee et al. *Arteriosclerosis, Thrombosis, and Vascular Biology.* 2003; 23:853-858).

Triglyceride-rich lipoproteins that contain ApoC-III are also prominent in diabetic dyslipidemia. It is theorized that these lipoproteins increase coronary disease risk in diabetic patients beyond that caused by standard lipid risk factors. Specifically, LDL with ApoC-III has been found to be a predictor of coronary events in diabetic patients independently of other lipids and is thought to be an atherogenic remnant of triglyceride-rich VLDL metabolism (Lee et al. *Arteriosclerosis, Thrombosis, and Vascular Biology.* 2003; 23:853-858).

Additionally, studies have found that ApoC-III in HDL (or the cholesterol concentration of HDL that has ApoC-III) is associated with risk of CHD. Also, ApoC-III has a direct pro-atherogenic, pro-inflammatory effect on monocytes and vascular endothelial cells. ApoC-III in HDL does not have a protective action against monocyte adhesion to vascular endothelial cells.

ApoC-III is a small protein on the surface of ApoB lipoproteins which strongly effects their metabolism. VLDL and LDL (apoB lipoproteins) contain subpopulations that have ApoCIII and ApoCIII is increased in ApoB lipoproteins in patients with diabetes. ApoCIII is an inhibitor of the activity of lipoprotein lipase, which metabolizes triglyceride in VLDL and facilitates their clearance from plasma. ApoCIII also obstructs the clearance from plasma of VLDL and LDL by interfering with their interaction with hepatic lipoprotein (Lee et al. *Arteriosclerosis, Thrombosis, and Vascular Biology.* 2003; 23:853-858).

Antisense reduction of ApoC-III coincides with a reduction in serum cholesterol and triglycerides, liver triglycerides, glucose and fat in hyperlipidemic models (U.S. application Ser. No. 10/553,722.

The lowering ApoC-III by antisense inhibition of ApoB therefore renders such ApoB targeting compounds useful for diabetic and/or obese subjects or subjects suffering from diabetic dyslipidemia, mixed dyslipidemia or steatosis.

Accordingly, in a first aspect, provided is a method for treating, reducing the incidence of, or ameliorating a symptom of coronary heart disease in a diabetic subject, comprising selecting a human subject with diabetes having or at risk of having coronary heart disease; and administering to said human subject a therapeutically effective amount of a compound comprising a modified oligonucleotide having 12-30 linked nucleosides, or a salt thereof, wherein said modified oligonucleotide is 100% complementary to a nucleic acid encoding human apolipoprotein B, and wherein plasma apolipoprotein C-III levels in said human subject are lowered.

In certain embodiments, said subject has one or more of elevated plasma total cholesterol concentrations, elevated plasma LDL cholesterol, elevated plasma triglyceride concentrations, elevated plasma HDL cholesterol concentrations or elevated liver triglycerides concentrations. In certain embodiments, said subject has elevated plasma total cholesterol concentrations, elevated plasma LDL cholesterol, elevated plasma triglyceride concentrations, and elevated plasma HDL cholesterol concentrations. In certain embodiments, said subject has or is at risk of having diabetic dyslipidemia or mixed dyslipidemia. In certain embodiments, said subject has elevated Apo C-III concentrations in one or more lipoprotein subfractions. In certain embodiments, said subject has elevated apolipoprotein C-III concentrations in HDL cholesterol particles relative to a non-diabetic subject. In certain embodiments, said subject has elevated apolipoprotein C-III concentrations in VLDL cholesterol particles relative to a non-diabetic subject. In certain embodiments, said subject has elevated apolipoprotein C-III concentrations in cholesterol particles comprising apolipoprotein B relative to a non-diabetic subject. In certain embodiments, said subject has elevated apolipoprotein C-III concentrations in one or more of apolipoprotein B containing VLDL, HDL and LDL.

In another aspect, provided is a method for treating, reducing the incidence of, or ameliorating a symptom of coronary heart disease in an obese subject, comprising selecting an obese human subject having or at risk of having coronary heart disease; and administering to said obese human subject a therapeutically effective amount of a compound comprising a modified oligonucleotide having 12-30 linked nucleosides, or a salt thereof, wherein said modified oligonucleotide is 100% complementary to a nucleic acid encoding human apolipoprotein B, and wherein plasma apolipoprotein C-III levels in said obese human subject are lowered.

In certain embodiments, said subject has one or more of elevated plasma total cholesterol concentrations, elevated plasma LDL cholesterol, elevated plasma triglyceride concentrations, elevated plasma HDL cholesterol concentrations or elevated liver triglycerides concentrations. In certain embodiments, said subject has elevated plasma total cholesterol concentrations, elevated plasma LDL cholesterol, elevated plasma triglyceride concentrations, and elevated plasma HDL cholesterol concentrations. In certain embodiments, said subject has or is at risk of having diabetic dyslipidemia or mixed dyslipidemia. In certain embodiments, said subject has elevated Apo C-III concentrations in one or more lipoprotein subfractions. In certain embodiments, said subject has elevated apolipoprotein C-III concentrations in HDL cholesterol particles relative to a non-obese subject. In certain embodiments, said subject has elevated apolipoprotein C-III concentrations in VLDL cholesterol particles relative to a non-obese subject. In certain embodiments, said subject has elevated apolipoprotein C-III concentrations in cholesterol particles comprising apolipoprotein B relative to a non-obese subject. In certain embodiments, said subject has elevated apolipoprotein C-III concentrations in one or more of apolipoprotein B containing VLDL, HDL and LDL.

Certain Combination Therapies

The invention also provides methods of combination therapy, wherein, one or more compositions or compounds targeting ApoB and one or more other therapeutic/prophylactic agents are administered to treat a condition and/or disease state as described herein. In certain embodiments, a compound targeting ApoB and the therapeutic/prophylactic agent(s) are co-administered as a mixture or administered concomitantly. In certain embodiments, the route of administration is the same for the compound targeting ApoB and the therapeutic/prophylactic agent(s), while in other embodiments, the compound targeting ApoB and the therapeutic/prophylactic agents(s) are administered by different routes. In one embodiment, the dosages of the compound targeting ApoB and the therapeutic/prophylactic agent(s) are amounts that are therapeutically or prophylactically effective for each compound when administered as independent therapy. Alternatively, the combined administration permits use of lower dosages than would be required to achieve a therapeutic or prophylactic effect if administered as independent therapy. In certain embodiments, combination therapy methods are useful in decreasing one or more side effects of either the ApoB targeting compound or other agent.

In certain embodiments, one or more compounds targeting ApoB are co-administered with one or more other therapeutic/prophylactic agents. In certain embodiments, such one or more other therapeutic/prophylactic agent are designed to treat the same disease or condition as the compounds targeting ApoB. In certain embodiments, such one or more other therapeutic/prophylactic agents are designed to treat a different disease or condition. In certain embodiments, one or more compounds targeting ApoB and one or more other therapeutic/prophylactic agents are administered at the same time. In certain embodiments, one or more compounds targeting ApoB and one or more other therapeutic/prophylactic agents are administered at different times. In certain embodiments, one or more compounds targeting ApoB and one or more other therapeutic/prophylactic agents are prepared together in a single formulation. In certain embodiments, one or more compounds targeting ApoB and one or more other therapeutic/prophylactic agents are prepared separately. In certain embodiments, an additive or synergistic effect is achieved by administering one or more compounds and one or more other suitable therapeutic/prophylactic compounds.

Suitable therapeutic/prophylactic compound(s) include, but are not limited to, glucose-lowering agents (also referred to herein, as glucose-lowering drugs or glucose-lowering therapeutics), anti-obesity agents (also referred to herein, as anti-obesity drugs or anti-obesity therapeutics), and lipid lowering agents (also referred to herein, as lipid-lowering drugs or lipid-lowering therapeutics).

Glucose Lowering Agents

Diabetes agents include insulin, other hormones and hormone analogs and mimetics, and other glucose lowering agents, including orally administered glucose lowering drugs. The term "glucose-lowering agent" includes, but is not limited to, the sulfonylureas, biguanides, meglitinides, peroxisome proliferator-activated receptor-gamma (PPAR-gamma) agonists (e.g., thiazolidinediones) and alpha-glucosidase inhibitors.

Sulfonylureas work by stimulating beta-cell insulin secretion in the pancreas, and may also improve insulin sensitivity in peripheral tissues. Early sulfonylureas such as acetohexamide (Dymelor™), chlorpropamide (Diabinese™, Glucamide™), tolbutamide (Orinase™, Mobenol™), and tolazamide (Tolamide™, Tolinase™) have been generally replaced with newer sulfonureas with better side-effect profiles (specifically lower cardiovascular risk), such as glimepiride (Amaryl™), glipizide (Glucotrol™), glipizide extended release (Glucotrol XL™), glyburide (Micronase™, Euglucon™, Diabeta™), gliclazide (Diamicron™), and micronized glyburide (Glynase™) (Luna & Feinglos; AACE et al., 2002). Side effects of sulfonylureas include hypoglycemia and weight gain.

Biguanides such as Metformin (Glucophage™) work by decreasing hepatic glucose output and enhancing insulin sensitivity in hepatic and peripheral tissues. Metformin is contraindicated in patients with congestive heart failure or severe liver disease.

Meglitinides work by stimulating the beta cells in the pancreas to produce insulin. Nateglinide (Starlix™) and repaglinide (Prandin™) are examples of this class.

Peroxisome proliferator-activated receptor-gamma (PPAR-gamma) agonists such as the thiazolidinediones enhance insulin sensitivity in muscle and adipose tissue and, to a lesser extent, inhibit hepatic glucose production. Thiazolidinediones include pioglitazone (Actos™) and rosiglitazone (Avandia™; GlaxoSmithKline). The first thiazolidinedione approved for use in the United States, troglitazone (Rezulin™), was withdrawn from the market because of severe liver toxicity. Thiazolidinediones also affect the lipid profiles of patients with type 2 diabetes. Studies have described that rosiglitazone is associated with increases in total, LDL, and HDL cholesterol levels, and either no changes or increases in triglyceride levels. Pioglitazone has been associated with mean decreases in triglyceride levels, mean increases in HDL cholesterol levels, and no consistent mean changes in LDL and total cholesterol levels. Other potential side effects associated with thiazolidinediones include weight gain, slow onset of action, and potential liver toxicity (Luna & Feinglos, 2001).

New PPAR-gamma agonists are being developed; these include isaglitazone (netoglitazone) and the dual-acting PPAR agonists which have affinities for both PPAR-gamma and PPAR-alpha. Examples of dual-acting PPAR agonists are BMS-298585 and tesaglitazar. Agonists of other PPARs (e.g., alpha, delta) or pan-PPAR agonists may also be useful.

Alpha-glucosidase inhibitors inhibit an enzyme found in the lining of the small intestine that is responsible for the breakdown of complex carbohydrates before they are absorbed. Such inhibitors include acarbose (Precose™) and miglitol (Glyset™)

Oral glucose-lowering drugs are often used in combination to treat Type 2 diabetes. While many combinations of the above are possible, several are already marketed as a combined formulation (for example, Avandamet™ (Rosiglitazone+Metformin); Glucovance™ (glyburide/metformin); and Metaglip™ (glipizide/metformin). These and other combined formulations for treatment of diabetes or obesity may be administered in combination with one or more ApoB targeting compound.

Other classes of glucose-lowering, diabetes drugs are being developed. As alternatives to regular insulin, which is administered by injection, insulin analogs such as insulin lispro (Humalog™) and insulin glargine (Lantus™) may be used. Both are given by injection as is regular insulin, but result in fewer hypoglycemic events than regular insulin. In addition the onset and duration of action with these is different from regular insulin. A follow-up analog to insulin glargine, insulin glulisine, is being developed by Aventis. Novo Nordisk is developing insulin detemir, a long-acting analog.

Alternative formulations/delivery methods for regular insulin are also being developed. Both liquid and dry powder inhaled insulin formulations are currently in late-stage development or have been recently approved—examples include recently approved Exubera™ (Nektar/Pfizer/Aventis), which is a powder, and AERx™ (Aradigm/Novo Nordisk), which is an aerosolized liquid. While inhaled insulin is expected to be viewed as more convenient and less invasive than injected insulin, the cost is expected to be much greater for inhaled insulin.

Several companies are developing oral formulations of insulin. Oralin™ (Generex Biotechnology) is the farthest along in development but there are others.

Other hormones and hormone mimetics being developed include pramlintide acetate (Symlin™), and GLP-1. GLP-1 receptor agonists and GLP-1 analogs are being evaluated for clinical use as antidiabetic agents. GLP-1 itself has a short half-life due to N-terminal degradation of the peptide by Dipeptidyl Peptidase (DPP-IV)-mediated cleavage at the position 2 alanine. This limits the clinical usefulness of native GLP-1 or synthetic versions thereof. Longer acting analogs have been developed, including Exendin-4 (Exenatide™, Exenatide LAR™), a DP IV-resistant GLP-1 analog and Liraglutide™, an acylated albumin-bound human GLP-1 analog.

DPP-IV inhibitors are also being explored as drugs and one (LAF-237, Novartis) is currently in advanced clinical trials. Glucagon inhibitors may also be useful for diabetes.

Other peptides such as pituitary adenylate cyclase-activating polypeptide (PACAP) and Peptide YY (PYY) (and its subpeptide PYY[3-36]) are also under study for diabetes and/or obesity (Yamamoto et al., 2003, Diabetes 52, 1155-1162; Pittner et al., Int. J. Obes. Relat. Metab. Disord. 2004, 28, 963-71).

ApoB targeting compounds can also be used in combination with other antisense compounds targeting metabolic targets (e.g., PTP-1B and SGLT2 targeting compounds)

Anti-Obesity Agents

In certain embodiments, compounds provided herein are advantageous for reducing fat and may be useful in treatment of obesity. The use of weight loss agents has also been considered useful in diabetes management in general and for delaying or preventing the development or progression of frank Type 2 diabetes in patients with impaired glucose tolerance (Heymsfield S B, 2000, Archives of Internal Medicine, 160, 1321-1326). Thus, anti-obesity drugs are useful in combination with compounds targeting ApoB. Examples of anti-obesity drugs (also called "diet drugs") include, without limitation, appetite suppressants such as phentermine and Meridia™, fat absorption inhibitors such as orlistat (Xenical™), and Axokine™, a modified form of ciliary neurotrophic factor, which inhibits hunger signals that stimulate appetite. Other drugs or classes of drugs under evaluation for obesity are CB1 inverse agonists, PYY, MCH4 and MTP inhibitors. ApoB targeting compounds can also be used in combination with other antisense compounds targeting obesity related targets.

Lipid Lowering Agents

Therapeutic/prophylactic compound(s) for the reduction of lipids include, but are not limited to, bile salt sequestering resins (e.g., cholestyramine, colestipol, and colesevelam hydrochloride), cholesterol biosynthesis inhibitors, especially HMG CoA reductase inhibitors (such as atorvastatin, pravastatin, simvastatin, lovastatin, fluvastatin, cerivastatin, rosuvastatin, and pitivastatin (itavastatin/risivastatin)), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe and pamaqueside), CETP inhibitors (e.g. torcetrapib, and JTT-705) MTP inhibitors (e.g., implitapide), squalene synthetase inhibitors, bile acid sequestrants such as cholestyramine, inhibitors of bile acid transporters (apical sodium-dependent bile acid transporters), regulators of hepatic CYP7a, ACAT inhibitors (e.g. Avasimibe), estrogen replacement therapeutics (e.g., tamoxigen), synthetic HDL (e.g. ETC-216), anti-inflammatories (e.g., glucocorticoids) and antisense compounds targeting cardiovascular targets (e.g., ApoC-III targeting compounds).

Dosing

In certain embodiments, pharmaceutical compositions are administered according to a dosing regimen (e.g., dose, dose frequency, and duration) wherein the dosing regimen can be selected to achieve a desired effect.

In certain embodiments, the variables of the dosing regimen are adjusted to result in a desired concentration of pharmaceutical composition in a subject. "Concentration of pharmaceutical composition" as used with regard to dose regimen can refer to the compound, oligonucleotide, or active ingredient of the pharmaceutical composition. For example, in certain embodiments, dose and dose frequency are adjusted to provide plasma concentration of a pharmaceutical composition at an amount sufficient to achieve a desired effect. In certain such embodiments, the pharmaceutical composition includes a modified oligonucleotide. In certain such embodiments, the modified oligonucleotide is ISIS 301012 (SEQ ID NO: 10). In certain of such embodiments the plasma concentration is maintained above the minimal effective concentration (MEC). In certain embodiments, pharmaceutical compositions of the present invention are administered with a dosage regimen designed to maintain a concentration above the MEC for 10-90% of the time, between 30-90% of the time, or between 50-90% of the time.

In certain embodiments, the dosing regimen can be selected to achieve a desired plasma trough concentration of a pharmaceutical composition. In certain such embodiments, the pharmaceutical composition includes a modified oligonucleotide. In certain such embodiments, the modified oligonucleotide is ISIS 301012. In certain such embodiments, the desired plasma trough concentration is from 5-100 ng/mL. In certain such embodiments, the desired plasma trough concentration is from 5-50 ng/mL. In certain such embodiments, the desired plasma trough concentration is from 10-40 ng/mL. In certain such embodiments, the desired plasma trough concentration is from 12-40 ng/mL. In certain such embodiments, the desired plasma trough concentration is from 15-35 ng/mL. In certain such embodiments, the desired plasma trough concentration is from 20-30 ng/mL. In certain such embodiments, the desired plasma trough concentration is from 18-40 ng/mL. In certain such embodiments, the desired plasma trough concentration is about 18 ng/mL or more. In certain embodiments, the plasma trough is achieved from about 3 to about 33 days after administration of at least one dose of the pharmaceutical composition.

In certain embodiments, the dosing regimen can be selected to achieve a desired plasma trough AUC of a pharmaceutical composition. In certain such embodiments, the pharmaceutical composition includes a modified oligonucleotide. In certain such embodiments, the modified oligonucleotide is ISIS 301012. In certain such embodiments, the desired plasma trough AUC is between about 2 to 40 μg·hr/mL, 2 to 30 μg·hr/mL, 2 to 20 μg·hr/mL, 2 to 10 μg·hr/mL, or 2 to 7 μg·hr/mL. In certain embodiments, the oligonucleotide is administered so that the plasma trough AUC is about 2 μg·hr/mL to about 40 μg·hr/mL, about 5 μg·hr/mL to about 30 μg·hr/mL, about μg·hr/mL to about 25 μg·hr/mL, about 12 μg·hr/mL to about 20 μg·hr/mL or about 12 μg·hr/mL to about 60 μg·hr/mL. In certain embodiments, the oligonucleotide is administered so that the plasma trough AUC is about 2 μg·hr/mL, about 3 μg·hr/mL, about 4 μg·hr/mL, about 5 μg·hr/mL, about 6 μg·hr/mL, about 7 μg·hr/mL, about 8 μg·hr/mL, about 9 μg·hr/mL, about 10 μg·hr/mL, about 11 μg·hr/mL, about 12 μg·hr/mL, about 13 μg·hr/mL, about 14 μg·hr/mL, about μg·hr/mL, about 16 μg·hr/mL, about 17 μg·hr/mL, about 18 μg·hr/mL, about 19 μg·hr/mL, about 20 μg·hr/mL, about 21 μg·hr/mL, about 22 μg·hr/mL, about 23 μg·hr/mL, about 24 μg·hr/mL, about 25 μg·hr/mL, about 26 μg·hr/mL, about 27 μg·hr/mL, about 28 μg·hr/mL, about 29 μg·hr/mL, about 30 μg·hr/mL, 31 μg·hr/mL, about 32 μg·hr/mL, about 33 μg·hr/mL, about 34 μg·hr/mL, about 35 μg·hr/mL, about 36 μg·hr/mL, about 37 μg·hr/mL, about 38 μg·hr/mL, about 39 μg·hr/mL or about 40 μg·hr/mL or greater. In certain embodiments, the plasma trough AUC is achieved from about 3 to about 33 days after administration of at least one dose of the pharmaceutical composition.

In certain embodiments, the dosing regimens comprise administering a pharmaceutical composition in certain doses. In certain embodiments, the pharmaceutical composition includes a modified oligonucleotide. In certain such embodiments, the modified oligonucleotide is ISIS 301012. In certain such embodiments, the desired dose is selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, the dose is selected from 25 mg, 50 mg, 75 mg, 100 mg, 150 mg, 200 mg, 250 mg, 300 mg, 350 mg, 400 mg, 500 mg, 600 mg, 700 mg, and 800 mg. In certain embodiments, the dose is selected from 50 mg, 100 mg, 150 mg, 200 mg, 250 mg, 300 mg, and 400 mg. In certain embodiments, the dose is selected from a range defined by any two of the preceding values.

In certain embodiments, the dosing regimen includes administering the pharmaceutical composition in a plurality of doses. In certain embodiments, the pharmaceutical composition includes a modified oligonucleotide. In certain such embodiments, the modified oligonucleotide is ISIS 301012. In certain embodiments, the dose is administered to a subject daily, twice a week, weekly, every two weeks, twice a month, monthly, every other month or on a mixed schedule. In certain embodiments, the pharmaceutical composition is administered at a dose/frequency of 50 mg/month, 100 mg/month, 150 mg/month, 200 mg/month, 250 mg/month, 300 mg/month, 350 mg/month or 400 mg/month. In certain embodiments, pharmaceutical composition is administered at 50 mg twice a month, 100 mg twice a month, 150 mg twice a month, 200 mg twice a month, 250 mg twice a month, 300 twice a month, 350 mg twice a month or 400 mg twice a month. In certain embodiments, pharmaceutical composition is administered at 50 mg/wk, 100 mg/wk, 150 mg/wk, 200 mg/wk, 250 mg/wk, 300 mg/wk, 350 mg/wk or 400 mg/wk. In certain embodiments, pharmaceutical composition is administered at 50 mg twice a week, 100 mg twice a week, 150 mg twice a week, 200 mg twice a week, 250 mg twice a week, 300 twice a week, 350 mg twice a week or 400 mg twice a week. In certain embodiments, pharmaceutical composition is administered at 25 mg/day, 30 mg/day, 35 mg/day, 40 mg/day, 45 mg/day, 50 mg/day, 100 mg/day, 150 mg/day, 200 mg/day, 250 mg/day, 300 mg/day, 350 mg/day or 400 mg/day.

In certain embodiments, a plurality of doses is administered to a subject in a mixed schedule comprising an induction phase (also known as a loading phase) and a maintenance phase.

In certain embodiments, the induction phase includes one, two, three, four, five, six, seven, eight, nine, ten, eleven, twelve, thirteen, fourteen, fifteen, sixteen, seventeen, eighteen, nineteen, twenty, or more than twenty doses. In certain embodiments where the induction phase includes more than one dose, the doses administered during the induction phase are all the same amount as one another. In certain embodiments, the doses administered during the induction phase are not all the same amount. In certain embodiments, the doses increase over time. In certain embodiments, the doses decrease over time.

In certain embodiments, the dose(s) during the induction phase are selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, the dose(s) during the induction phase are selected from 25 mg, 50 mg, 75 mg, 100 mg, 150 mg, 200 mg, 250 mg, 300 mg, 350 mg, 400 mg, 500 mg, 600 mg, 700 mg, and 800 mg. In certain such embodiments, the dose(s) during the induction phase are selected from 100 mg, 125 mg, 150 mg, 175 mg, 200 mg, 225 mg, 250 mg, 275 mg, 300 mg, 325 mg, 350 mg, 375 mg, and 400 mg. In certain such embodiments, the dose(s) during the induction phase are selected from 100 mg, 125 mg, 150 mg, 175 mg, 200 mg, 225 mg, 250 mg, and 300 mg.

In certain embodiments, the induction phase lasts from one day to six months. In certain embodiments an induction phase lasts from one week to five months as measured from administration of the first dose of the induction phase to administration of the first dose of the maintenance phase. In certain embodiments an induction phase lasts from one week to five months, from two weeks to five months, from three weeks to four months or from five weeks to three months, as measured from administration of the first dose of the induction phase to administration of the first dose of the maintenance phase. In certain embodiments an induction phase lasts one week, two weeks, three weeks, four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks, twenty-three weeks, twenty-four weeks or twenty-five weeks, as measured from administration of the first dose of the induction phase to administration of the first dose of the maintenance phase. In certain embodiments an induction phase lasts one, two, three, four, five, six, seven, eight, nine, ten, eleven, twelve, thirteen or fourteen days as measured from administration of the first dose of the induction phase to administration of the first dose of the maintenance phase.

In certain embodiments, dose, dose frequency, and duration of the induction phase can be selected to achieve a desired effect within one to thirteen weeks. In certain such embodiments, the dose can be the same and the dose frequency can varied to achieve the desired effect within one to thirteen weeks. In certain embodiments, the dose increases over time and the dose frequency remains constant. In certain such embodiments, doses and frequency are selected to achieve a desired effect within one week, two weeks, three weeks, four weeks, five weeks, six weeks, seven weeks, eight weeks, nine weeks, ten weeks, eleven weeks, twelve weeks or thirteen weeks.

In certain embodiments, the dose(s) administered during the induction phase are lower than, equal to or higher than the dose(s) administered during the maintenance phase. In certain embodiments, it is desirable to achieve a desired effect as quickly as possible. In such embodiments, an induction phase with a high dose and/or high dose frequency can be desirable. In certain embodiments, one or more doses of the induction phase is greater than one or more doses of the maintenance phase. In certain embodiments, each of the induction doses is greater than each of the maintenance doses. In certain embodiments, it is desirable to mitigate an undesired side effect. In certain embodiments, an induction phase with a low dose and/or low dose frequency and/or long duration can be desirable. For example, a long induction phase, with relatively low doses, can result in better tolerance of the pharmaceutical agent. In certain embodiments, an induction phase results in physiological changes that result in reduced overall side effects. In certain embodiments, such a dose regimen can result in reduced liver toxicity when compared to higher initial doses and/or frequency. Such embodiments can include gradual increases of dose over time.

In certain embodiments, the maintenance phase includes one, two, three, four, five, six, seven, eight, nine, ten, eleven, twelve, thirteen, fourteen, fifteen, sixteen, seventeen, eighteen, nineteen, twenty, or more than twenty doses.

In certain embodiments, the maintenance phase lasts from one day to the lifetime of the subject. In certain embodiments the maintenance phase lasts from one week to twenty years, from two weeks to fifteen years, three weeks to ten years, four weeks to ten years as measured from administration of the last dose of the induction phase to administration of the last dose of the maintenance phase. In certain embodiments the maintenance phase lasts one, two, three, four, five, six, seven, eight, nine, ten, eleven, twelve, thirteen, fourteen, fifteen, sixteen, seventeen, eighteen, nineteen, twenty, or more weeks. In certain embodiments the maintenance phase lasts as long as the dose continues to be needed, effective, and tolerated.

In certain embodiments where the maintenance phase includes more than one dose, the doses administered during the maintenance phase are all the same as one another. In certain embodiments, the doses administered during the maintenance phase are not all the same. In certain such embodiments, the doses increase over time. In certain embodiments, the doses decrease over time.

In certain embodiments, the dose(s) during the maintenance phase are selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, the dose(s) during the maintenance phase are selected from 25 mg, 50 mg, 75 mg, 100 mg, 150 mg, 200 mg, 250 mg, 300 mg, 350 mg, 400 mg, 500 mg, 600 mg, 700 mg, and 800 mg. In certain such embodiments, the dose(s) during the maintenance phase are selected from 100 mg, 125 mg, 150 mg, 175 mg, 200 mg, 225 mg, 250 mg, 275 mg, 300 mg, 325 mg, 350 mg, 375 mg, and 400 mg. In certain such embodiments, the dose(s) during the maintenance phase are selected from 100 mg, 125 mg, 150 mg, 175 mg, 200 mg, 225 mg, and 250 mg.

In certain embodiments, doses, dose frequency, and duration of the maintenance phase can be selected to achieve a desired effect. In certain embodiments, those variables are adjusted to result in a desired concentration of pharmaceutical agent in a subject. For example, in certain embodiments, dose and dose frequency are adjusted to provide plasma concentration of a pharmaceutical agent at an amount sufficient to achieve a desired effect. In certain of such embodiments the plasma concentration is maintained above the minimal effective concentration (MEC). In certain embodiments, pharmaceutical composition is administered with a dosage regimen designed to maintain a concentration above the MEC for 10-90% of the time, between 30-90% of the time, or between 50-90% of the time.

In certain embodiments, doses, dose frequency, and duration of the maintenance phase can be selected to achieve a desired plasma trough concentration of the pharmaceutical composition. In certain such embodiments, the pharmaceutical composition includes a modified oligonucleotide. In certain such embodiments, the modified oligonucleotide is ISIS 301012. In certain such embodiments, the desired plasma trough concentration is from 5-100 ng/mL. In certain such embodiments, the desired plasma trough concentration is from 5-50 ng/mL. In certain such embodiments, the desired plasma trough concentration is from 10-40 ng/mL. In certain such embodiments, the desired plasma trough concentration is from 12-40 ng/mL. In certain such embodiments, the desired plasma trough concentration is from 15-35 ng/mL. In certain such embodiments, the desired plasma trough concentration is from 20-30 ng/mL. In certain such embodiments, the desired plasma trough concentration is from 18-40 ng/mL.

In certain embodiments, doses, dose frequency, and duration of the maintenance phase can be selected to achieve a desired safety profile. For example, in certain embodiments, such variables may be selected to mitigate toxicity of the pharmaceutical composition. In certain such embodiments, such variables are selected to mitigate liver toxicity. In certain such embodiments, such variables are selected to mitigate renal toxicity. In certain such embodiments, doses increase over time.

In certain embodiments, doses, dose frequency, and duration of the maintenance phase can be adjusted from time to time to achieve a desired effect. In certain embodiments, subjects are monitored for effects (therapeutic and/or toxic effects) and doses, dose frequency, and/or duration of the maintenance phase may be adjusted based on the results of such monitoring. Dose, dose frequency, and duration for the induction phase and for the maintenance phase can be manipulated independently to achieve a desired effect.

In certain embodiments, a dose regimen includes administering to a subject a pharmaceutical composition in a plurality of doses. In a certain embodiment, the pharmaceutical composition includes a modified oligonucleotide. In a certain embodiment, the modified oligonucleotide is ISIS 301012. In certain embodiments, the dose regimen includes administering to a subject 200 mg every week for at least 13 weeks or as long as is necessary to sustain the desired effect. In certain embodiments, the dose regimen includes administering to a subject 300 mg every, week for at least 13 weeks or as long as is necessary to sustain the desired effect. In certain embodiments, the dose regimen includes an induction phase, where an induction dose of 200 mg is administered to a subject four times during an eleven day period. The induction phase is followed by a maintenance phase, where a maintenance dose of 200 mg is administered every other week for at least 11 weeks or as long as is necessary to sustain the desired effect.

In certain embodiments, the frequency of administration of the maintenance dose is adjusted to achieved desired efficacy and/or desired safety profile. In certain such embodiments, the frequency of the maintenance dose is adjusted to achieve a desired plasma trough concentration of antisense oligonucleotide ISIS 301012. In certain embodiments, the plasma trough concentration of the administered composition is about 12 ng/mL or more, 15 ng/mL or more, 18 ng/mL or more, 20 ng/mL or more, 25 ng/mL or more, 30 ng/mL or more, 35 ng/mL or more, or 40 ng/mL or more. In certain embodiments, the plasma trough concentration of the administered composition is 12-40 ng/mL, 15-35 ng/mL, 18-30 ng/mL or 20-25 ng/mL. In certain such embodiments, the plasma trough AUC of the administered composition is about 12 µg·hr/mL or more, 15 µg·hr/mL or more, 18 µg·hr/mL or more, 20 µg·hr/mL or more, 25 µg·hr/mL or more, 30 µg·hr/mL or more, 35 µg·hr/mL or more, 40 µg·hr/mL or more, 45 µg·hr/mL or more, 50 µg·hr/mL or more, 55 µg·hr/mL or more, 60 µg·hr/mL or more, 65 µg·hr/mL or more, 70 µg·hr/mL or more, 75 µg·hr/mL or more, 80 µg·hr/mL or more, 85

μg·hr/mL or more, 90 μg·hr/mL or more, 95 μg·hr/mL or more, 100 μg·hr/mL or more, 110 μg·hr/mL or more, 125 μg·hr/mL or more, 150 μg·hr/mL or more. In certain such embodiments, the plasma trough AUC of the administered composition is 12-60 μg·hr/mL, 12-160 μg·hr/mL, 15-125 μg·hr/mL, 18-100 μg·hr/mL, 20-95 μg·hr/mL, 25-90 μg·hr/mL, 30-85 μg·hr/mL, 35-80 μg·hr/mL, 40-75 μg·hr/mL, 45-70 μg·hr/mL, 50-65 μg·hr/mL, 30-40 μg·hr/mL, 30-50 μg·hr/mL, 30-55 μg·hr/mL, 55-60 μg·hr/mL. In certain such embodiments, the desired effect is reduced Apo C-III Compositions having an oligonucleotide targeting ApoB other than ISIS 301012 may vary in activity (e.g., as defined by percent reduction of target nucleic acid levels) from a composition having ISIS 301012. In certain embodiments, reductions in ApoB mRNA levels are indicative of inhibition of ApoB expression. Reductions in levels of ApoB protein are also indicative of inhibition of target mRNA expression. Further, phenotypic changes are indicative of inhibition of ApoB expression. For example, the lowering of ApoC-III is indicative of inhibition of target mRNA expression. In certain embodiments, the level of activity of a composition is higher or lower than that of a composition containing ISIS 301012. In such embodiment, the dose is adjusted accordingly lower or higher to achieve the desired efficacy.

Administration

In certain embodiments, pharmaceutical compositions can be administered to a subject by various methods. In certain embodiments, the method of administering a pharmaceutical composition to a subject comprises administering the pharmaceutical composition in the form of a dosage unit (e.g., tablet, capsule, bolus, etc.).

In certain embodiments, the pharmaceutical composition is administered by parenteral administration. In certain such embodiments, the parenteral administration is subcutaneous injection. In certain such embodiments, the parenteral administration is intravenous infusion.

In certain embodiments, where subcutaneous administration is desired, a dose of the pharmaceutical composition can be administered in two or more subcutaneous injections. In certain such embodiments, when the desired dose of the pharmaceutical composition requires a volume not easily accommodated by a single injection, two or more subcutaneous injections may be used to achieve the desired dose. In certain such embodiments, two or more subcutaneous injections may be used to administer the desired dose to minimize or eliminate an injection site reaction in a subject.

In certain embodiments in which a pharmaceutical composition is administered locally, the dosage regimen is selected to achieve a desired local concentration of the pharmaceutical agent of the present invention.

Certain Compounds

Modified oligonucleotide ISIS 301012 was designed to target human Apolipoprotein B RNA, using published sequence GenBank accession number NM_000384.1, SEQ ID NO: 1. ISIS 301012 is a chimeric oligonucleotide synthesized using methods as described in WO 2004044181, which is incorporated herein by reference in its entirety. The chimeric ISIS 301012 oligonucleotide is a "gapmer" 20 nucleobases in length (GCCTCAGTCTGCTTCGCACC; SEQ ID NO: 10), composed of a central "gap" region having ten contiguous 2'-deoxyribonucleosides, and flanked on both sides (5' and 3' directions) by "wing" regions having five contiguous 2'-O-methoxyethyl (2'-MOE) nucleosides. ISIS 301012 is shown in Table 1. The 2'-deoxyribonucleoside gap (nucleosides 6-15) are indicated by plain type and 2'-MOE nucleosides (nucleosides 1-5 and 16-20) are indicated by emboldened, underlined type. The internucleoside (backbone) linkages are phosphorothioate (P=S) throughout the modified oligonucleotide. All cytidine residues are 5-methylcytidines.

Modified oligonucleotides have been designed to target the human Apolipoprotein B RNA or DNA, using published sequences such as GenBank accession number NM_000384.1, incorporated herein as SEQ ID NO: 1; GenBank accession number NM_000384.2, incorporated herein as SEQ ID NO: 2; GenBank accession number M19734.1, incorporated herein as SEQ ID NO: 3; GenBank accession number M18471.1, incorporated herein as SEQ ID NO: 4; GenBank accession number M17779.1, incorporated herein as SEQ ID NO: 5; GenBank accession number X04714.1, incorporated herein as SEQ ID NO: 6; GenBank accession number M14162.1, incorporated herein as SEQ ID NO: 7; nucleotides 39835 to 83279 of GenBank accession number NT_022227.9, incorporated herein as SEQ ID NO: 8; and, GenBank accession number AI249040.1, incorporated herein as SEQ ID NO: 9.

Examples of oligonucleotides designed to target human Apolipoprotein B RNA can be found in U.S. application Ser. Nos. 11/123,656, 11/573,537 and 10/712,795, herein incorporated by reference.

Length

Compounds include, but are not limited to, those having an oligomeric sequence including oligonucleotides, oligonucleosides, oligonucleotide analogs, oligonucleotide mimetics, antisense compounds, antisense oligonucleotides, and siRNAs. A compound may have a nucleobase portion that is "antisense" to a target nucleic acid, meaning that is capable of undergoing hybridization to a target nucleic acid through hydrogen bonding. In such embodiment, the compound is targeted to the nucleic acid.

In certain embodiments, a compound has a nucleobase portion that, when written in the 5' to 3' direction, comprises the reverse complement of the target segment of a target nucleic acid to which it is targeted. In certain such embodiments, the compound has a modified oligonucleotide with a nucleobase sequence that, when written in the 5' to 3' direction, comprises the reverse complement of the target segment of a target nucleic acid to which it is targeted.

In certain embodiments, a compound targeted to an Apo B nucleic acid has an oligomeric sequence that is 12 to 30 subunits in length. In other words, the oligomeric sequence is from 12 to 30 linked subunits. In other embodiments, the compound has a an oligomeric sequence that is 8 to 80, 12 to 50, 15 to 30, 18 to 24, 19 to 22, or 20 linked subunits. In certain such embodiments, the compound has an oligomeric sequence that is 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits, or a range defined by any two of the above values. In certain embodiments the compound has a modified oligonucleotide sequence, and the linked subunits are nucleosides.

In certain embodiments, a compound has a shortened or truncated sequence targeted to an Apo B nucleic acid. In certain embodiments the trucated sequence has a single subunit deleted from the 5' end (5' truncation), or alternatively from the 3' end (3' truncation). A compound with a shortened or truncated sequence targeted to an Apo B nucleic acid may have two subunits deleted from the 5' end, or alternatively may have two subunits deleted from the 3' end, of the sequence. Alternatively, the deleted subunits may be dispersed throughout the sequence, for example, in a sequence having one subunit deleted from the 5' end and one subunit deleted from the 3' end. In certain embodiments the sequence is a modified oligonucleotide sequence, and the subunits are nucleosides.

When a single additional subunit is present in a lengthened sequence targeted to an Apo B nucleic acid, the additional subunit may be located at the 5' or 3' end of the sequence. When two or more additional subunits are present, the added subunits may be adjacent to each other, for example, two subunits can be added to the 5' end (5' addition), or alternatively to the 3' end (3' addition), of the sequence. Alternatively, the added subunits may be dispersed throughout the sequence, for example, one subunit can added to the 5' end and one subunit added to the 3' end. In certain embodiments the sequence is a modified oligonucleotide sequence, and the subunits are nucleosides.

It is possible to increase or decrease the length of a sequence targeted to an Apo B nucleic acid, such as modified oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Motifs

In certain embodiments, compounds having oligomeric sequences targeted to an Apo B nucleic acid have chemically modified subunits arranged in patterns, or motifs, to confer to the certain properties such as enhanced inhibitory activity, increased binding affinity for a target nucleic acid, or resistance to degradation by in vivo nucleases.

Chimeric sequences typically contain at least one region modified so as to confer increased resistance to nuclease degradation, increased cellular uptake, increased binding affinity for the target nucleic acid, and/or increased inhibitory activity. A second region of a chimeric sequence may optionally serve as a substrate for the cellular endonuclease RNase H, which cleaves the RNA strand of an RNA:DNA duplex. In certain embodiments the chimeric sequence is a chimeric oligonucleotide.

Oligomeric sequence with a gapmer motif are considered chimeric. In a gapmer, an internal region or "gap" having a plurality of subunits that support RNaseH cleavage is positioned between external regions or "wings" having a plurality of subunits that are chemically distinct from the subunits of the internal region. In the case of an antisense oligonucleotide having a gapmer motif, the gap segment has consecutive linked 2' deoxyribonucleosides and generally serves as the substrate for endonuclease cleavage, while the wing segments comprise 1 or more consecutive modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the compounds described herein can have a sequence with a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 5-10-5, 4-8-4, 4-12-3, 4-12-4, 3-14-3, 2-13-5, 2-16-2, 1-18-1, 3-10-3, 2-10-2, 1-10-1 or 2-8-2.

In certain embodiments, the compound has a sequence with a "wingmer" motif, having a wing-gap or gap-wing configuration, i.e. an X-Y or Y-Z configuration as described above for the gapmer configuration. Thus, wingmer configurations of the present invention include, but are not limited to, for example 5-10, 8-4, 4-12, 12-4, 3-14, 16-2, 18-1, 10-3, 2-10, 1-10, 8-2, 2-13, or 5-13.

In certain embodiments, antisense compounds targeted to an Apo B nucleic acid possess a 5-10-5 gapmer motif.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an Apo B nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or C(R1)(R2) (R=H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH3 and 2'-O(CH2)2OCH3 substituent groups. The substituent at the 2' position can also be selected from allyl, amino, azido, thio, O-allyl, O—C1-C10 alkyl, OCF3, O(CH2)2SCH3, O(CH2)2-O—N(Rm) (Rn), and O—CH2-C(=O)—N(Rm)(Rn), where each Rm and Rn is, independently, H or substituted or unsubstituted C1-C10 alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH2)-O-2' (LNA); 4'-(CH2)-S-2'; 4'-(CH2)-O-2' (LNA); 4'-(CH2)2-O-2' (ENA); Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring.

Many other bicyclo and tricyclo sugar surrogate ring systems are also know in the art that can be used to modify nucleosides for incorporation into antisense compounds Such ring systems can undergo various additional substitutions to enhance activity.

In nucleotides having modified sugar moieties, the nucleobase moieties (natural, modified or a combination thereof) are maintained for hybridization with an appropriate nucleic acid target.

In certain embodiments, antisense compounds targeted to an Apo B nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH₃) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an Apo B nucleic acid comprise one or more modified nucleobases. In certain embodiments, antisense oligonucleotides targeted to an Apo B nucleic acid comprise one or more modified nucleobases. In certain embodiments, the modified nucleobase is 5-methylcytosine. In certain embodiments, each cytosine is a 5-methylcytosine.

Hybridization

In some embodiments, hybridization occurs between an antisense compound disclosed herein and an Apo B nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with an Apo B nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an Apo B nucleic acid).

Non-complementary nucleobases between an antisense compound and an Apo B nucleic acid may be tolerated provided that the antisense compound remains able to specifically hybridize to a target nucleic acid. Moreover, an antisense compound may hybridize over one or more segments of an Apo B nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an Apo B nucleic acid, a target region, target segment, or specified portion thereof. Percent complementarity of an antisense compound with a target nucleic acid can be determined using routine methods. For example, an antisense compound in which 18 of 20 nucleobases of the antisense compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarily of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to an Apo B nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an Apo B nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an Apo B nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Compositions and Methods for Formulating Pharmaceutical Compositions

The compounds provided herein may be admixed with pharmaceutically acceptable active or inert substance for the preparation of pharmaceutical compositions or formulations. Compositions and methods for the formulation of compositions are dependent upon a number of criteria, including, but not limited to, route of administration, extent of disease, or dose to be administered.

The Compounds provided herein can be utilized in pharmaceutical compositions by combining the compound with a suitable pharmaceutically acceptable excipient, vehicle, carrier or diluent. Such pharmaceutically acceptable excipient, vehicle, carrier or diluent can include phosphate-buffered saline (PBS). In certain embodiments PBS is used in compositions to be delivered parenterally. Accordingly, in one embodiment, employed in the methods described herein is a composition comprising a compound targeted to an Apo B nucleic acid and a pharmaceutically acceptable excipient, vehicle, carrier or diluent. In certain embodiments, the pharmaceutically acceptable excipient, vehicle, carrier or diluent is PBS. In certain embodiments, the compound includes a modified oligonucleotide.

Pharmaceutical compositions comprising compounds targeting Apo B nucleic acid encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts compounds, oligonucleotides, prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

The oligomeric sequences provided herein may be covalently linked to one or more moieties or conjugates which enhance the activity, cellular distribution or cellular uptake of the resulting oligomeric sequence. In certain embodiments, the oligomeric sequence is a modified oligonucleotide. In certain embodiments, the modified oligonucleotide is a single stranded oligonucleotide. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Oligomeric sequences can also be modified to have one or more stabilizing groups that are generally attached to one or both termini of the sequence to enhance properties such as, for example, nuclease stability. In certain embodiments, the oligomeric sequence is a modified oligonucleotide. In certain embodiments, the modified oligonucleotide is a single stranded oligonucleotide. Included in stabilizing groups are cap structures. These terminal modifications protect the compounds having terminal nucleotides from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003, herein incorporated by reference.

Analysis of Inhibition of Target Levels or Expression

Inhibition of levels or expression of an ApoB nucleic acid can be assayed in a variety of ways known in the art (Sambrooke and Russell, Molecular Cloning: A Laboratory Manual, $3^{rd}$ Ed., 2001). For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Carlsbad, Calif.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to an ApoB nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of Apo B nucleic acids can be assessed by measuring ApoB protein levels. Protein levels of Apo B can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrooke and Russell, Molecular Cloning: A Laboratory Manual, $3^{rd}$ Ed., 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat Apo B are commercially available.

It is understood that the sequence set forth in each SEQ ID NO in the Examples contained herein is independent of any nucleotide modification including modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Mipomersen (ISIS 301012)

Modified oligonucleotides have been designed to target the human Apolipoprotein B RNA or DNA, using published sequences such as GenBank accession number NM_000384.1, incorporated herein as SEQ ID NO: 1; GenBank accession number NM_000384.2, incorporated herein as SEQ ID NO: 2; GenBank accession number M19734.1, incorporated herein as SEQ ID NO: 3; GenBank accession number M18471.1, incorporated herein as SEQ ID NO: 4; GenBank accession number M17779.1, incorporated herein as SEQ ID NO: 5; GenBank accession number X04714.1, incorporated herein as SEQ ID NO: 6; GenBank accession number M14162.1, incorporated herein as SEQ ID NO: 7; nucleotides 39835 to 83279 of GenBank accession number NT_022227.9, incorporated herein as SEQ ID NO: 8; and, GenBank accession number AI249040.1, incorporated herein as SEQ ID NO: 9.

Examples of oligonucleotides designed to target human Apolipoprotein B RNA can be found in U.S. application Ser. Nos. 11/123,656, 11/573,537 and 10/712,795, herein incorporated by reference.

Modified oligonucleotide ISIS 301012 was designed to target human Apolipoprotein B RNA, using published sequence GenBank accession number NM_000384.1, SEQ ID NO: 1. ISIS 301012 is a chimeric oligonucleotide synthesized using methods as described in WO 2004044181, which is incorporated herein by reference in its entirety. The chimeric ISIS 301012 oligonucleotide is a "gapmer" 20 nucleobases in length (GCCTCAGTCTGCTTCGCACC; SEQ ID NO: 10), composed of a central "gap" region having ten contiguous 2'-deoxyribonucleosides, and flanked on both sides (5' and 3' directions) by "wing" regions having five contiguous 2'-O-methoxyethyl (2'-MOE) nucleosides. ISIS 301012 is shown in Table 1. The 2'-deoxyribonucleoside gap (nucleosides 6-15) are indicated by plain type and 2'-MOE nucleosides (nucleosides 1-5 and 16-20) are indicated by emboldened, underlined type. The internucleoside (backbone) linkages are phosphorothioate (P=S) throughout the modified oligonucleotide. All cytidine residues are 5-methylcytidines.

In Table 1, "Target site" indicates the first (5'-most) nucleotide number on the particular target sequence to which the oligonucleotide binds.

TABLE 1

| ISIS # | REGION | TARGET SITE | SEQUENCE | SEQ ID NO |
|---|---|---|---|---|
| 301012 | Coding Region | 3249 | GCCTCAGTCTGCTTCGCACC | 10 |

ISIS 301012 has been shown to reduce human Apolipoprotein B in vitro and in vivo (U.S. application Ser. Nos. 11/123,656 and 11/200,710, incorporated herein by reference in their entirety).

Example 2

Effects of Apolipoprotein B Antisense Inhibition in Cynomolgus Monkeys

Cynomolgus monkeys (male or female) were used to evaluate antisense oligonucleotides for their potential to lower Apolipoprotein B mRNA or protein levels in vivo, as well as to evaluate phenotypic endpoints associated with Apolipoprotein B expression. As part of this example, LDL-cholesterol and total cholesterol levels of the treated monkeys were determined.

ISIS 301012 in Lean Cynomolgus Monkeys

The oligonucleotide ISIS 301012 was investigated in a long-term study for its effects on Apolipoprotein B expression and serum lipid levels in Cynomolgus monkeys.

Male and female Cynomolgus monkeys were treated with 2, 4 or 12 mg/kg of ISIS 301012 intravenously, or 2 or 20 mg/kg subcutaneously, at a frequency of every two days for the first week, and every 4 days thereafter, for 1 and 3 month treatment periods. Saline-treated animals served as negative controls. Each treatment group included 2 to 3 animals of each sex.

At a one month interval and at the 3 month study termination, the animals were sacrificed and evaluated for Apolipoprotein B expression in liver, lipid levels in serum and indicators of toxicity. RNA was isolated from liver tissue and Apolipoprotein B mRNA expression was measured by real-time PCR as described in U.S. application Ser. No. 10/712,795, which is herein incorporated by reference in its entirety. Serum lipids, including total cholesterol, LDL-cholesterol, HDL-cholesterol and triglycerides, were evaluated by routine clinical analysis, e.g., using an Olympus Clinical Analyzer (Olympus America Inc., Melville, N.Y.). Ratios of LDL-cholesterol to HDL-cholesterol and total cholesterol to HDL-cholesterol were also calculated. Analyses of serum alanine aminotransferase (ALT) and serum asparate aminotransferase (AST), inflammatory infiltrates in tissue and basophilic granules in tissue provided an assessment of toxicities related to the treatment. Hepatic steatosis, or accumulation of lipids in the liver, was assessed by routine histological analysis with oil red O stain and measurement of liver tissue triglycerides using a Triglyceride GPO Assay (Sigma-Aldrich, St. Louis, Mo.).

The results from the one month interval of the long term treatment are shown in Table 2 and were normalized to saline-treated animals for mRNA and to untreated baseline values for lipid levels. Total cholesterol, LDL-cholesterol, HDL-cholesterol, LDL particle concentration and triglyceride levels in serum were measured by nuclear magnetic resonance spectroscopy by Liposcience (Raleigh, N.C.). Additionally, the concentration of intact oligonucleotide in liver was measured by capillary gel electrophoresis and is presented as micrograms of oligonucleotide per gram of liver tissue. Each result represents the average of data from 4 animals (2 males and 2 females). Where present, "N.D." indicates "not determined."

ISIS 301012, total cholesterol, LDL-cholesterol, HDL-cholesterol, LDL particle concentration and triglyceride levels in serum were measured by nuclear magnetic resonance spectroscopy by LipoScience, Inc. (Raleigh, N.C.). These data are shown in Table 3 and are normalized to untreated baseline values. Each result represents the average of data from 4 animals (2 males and 2 females).

TABLE 3

Effects of ISIS 301012 in lean Cynomolgus monkeys after 13 weeks of treatment

| Lipid parameters, % change normalized to untreated baseline value | Saline | 2 mg/kg | 20 mg/kg |
|---|---|---|---|
| Total cholesterol | +11 | +7 | +11 |
| LDL-cholesterol | +36 | +4 | −3 |
| HDL-cholesterol | −8 | +18 | +5 |
| LDL/HDL | +64 | −6 | −20 |
| Total cholesterol/HDL | +30 | +5 | −11 |
| Triglyceride | +36 | +5 | +10 |
| LDL Particle concentration | +31 | −3 | −7 |

These data illustrate significantly decreased LDL-cholesterol and total cholesterol/HDL and LDL/HDL ratios following 13 weeks of treatment with ISIS 301012. Furthermore, HDL-cholesterol levels were significantly increased.

Hepatic steatosis, or accumulation of lipids in the liver, was not observed following 4 weeks of treatment with the doses indicated. Expected dose-related toxicities were observed at the higher doses of 12 and 20 mg/kg, including a transient 1.2-1.3 fold increase in activated partial thromboplastin time (APTT) during the first 4 hours and basophilic granules in the liver and kidney (as assessed by routine histological examination of tissue samples). No functional changes in kidney were observed.

In a similar experiment, male and female Cynomolgus monkeys received an intravenous dose of ISIS 301012 at 4

TABLE 2

Effects of ISIS 301012 in lean Cynomolgus monkeys after 4 weeks of treatment

| | | Intravenous delivery | | | Subcutaneous injection | |
|---|---|---|---|---|---|---|
| | Saline | 2 mg/kg | 4 mg/kg | 12 mg/kg | 3.5 mg/kg | 20 mg/kg |
| apolipoprotein B expression (% change normalized to saline) | | −45 | −76 | −96 | N.D. | −94 |
| antisense oligonucleotide concentration in liver (µg/g) | | 92 | 179 | 550 | N.D. | 855 |
| Lipid Parameters (% change normalized to untreated baseline value) | | | | | | |
| Total cholesterol | +1 | −6 | −2 | −2 | +5 | −5 |
| LDL-cholesterol | +17 | +15 | +9 | +3 | −4 | −16 |
| HDL-cholesterol | −11 | −23 | −15 | −8 | +13 | +5 |
| LDL/HDL | +62 | +94 | +38 | +44 | −15 | −19 |
| Total cholesterol/HDL | +30 | +44 | +22 | +21 | −7 | −10 |
| Triglyceride | +37 | +26 | +32 | +15 | +1 | −3 |
| LDL Particle concentration | +15 | +8 | +8 | −11 | −14 | −21 |

These data show that ISIS 301012 inhibited Apolipoprotein B expression in a dose-dependent manner in a primate species and concomitantly lowered lipid levels at higher doses of ISIS 301012. Furthermore, these results demonstrate that ISIS 301012 accumulated in the liver in a dose-dependent manner.

Following 13 weeks of treatment with a 2 mg/kg intravenous dose of ISIS 301012 or a 20 mg/kg subcutaneous dose of mg/kg, every two days for the first week and every 4 days thereafter. Groups of animals were sacrificed after the first dose and the fourth dose, as well as 11, 15 and 23 days following the fourth and final dose. Liver RNA was isolated and Apolipoprotein B mRNA levels were evaluated by real-time PCR as described in U.S. application Ser. No. 10/712, 795, which is herein incorporated by reference in its entirety. The results of this experiment demonstrated a 40% reduction in Apolipoprotein B mRNA expression after a single intravenous dose of 4 mg/kg ISIS 301012. Furthermore, after 4 doses of ISIS 301012 at 4 mg/kg, Apolipoprotein B mRNA was reduced by approximately 85% and a 50% reduction in Apolipoprotein B mRNA was sustained for up to 16 days following the cessation of ISIS 301012 treatment.

Example 3

Evaluation of Mipomersen (ISIS 301012) in a Phase I Clinical Study

As described below, ISIS 301012 was tested in a double blind, placebo-controlled, Phase I, dose-escalation study for the purpose of evaluating the safety and tolerability of single and multiple doses of ISIS 301012 administered to humans intravenously and subcutaneously. In addition, these studies evaluated the pharmacokinetic profile of single and multiple doses of ISIS 301012 administered intravenously and subcutaneously; and also evaluated the pharmacodynamics of ISIS 301012 administered intravenously and subcutaneously.

For this Example, a solution of ISIS 301012 (250 mg/mL, 0.5 mL) in sterile, unpreserved, buffered saline contained in 2-mL stoppered glass vials was provided. The study drug was stored securely at 2° C. to 8° C. and protected from light. The placebo was 0.9% sterile saline.

Study Design

Subjects, 18 to 65 years of age with total cholesterol between 200 and 300 mg/dL after an overnight fast and a body mass index (BMI) of less than 30 kg/m2, were randomized into Cohorts to receive ISIS 301012 or placebo in a 3:1 ratio. The dosing cohorts were as follows: Cohort A, 50 mg ISIS 301012 or placebo; Cohort B, 100 mg ISIS 301012 or placebo; Cohort C, 200 mg ISIS 301012 or placebo; Cohort D, 400 mg ISIS 301012 or placebo.

The study consisted of a single dose component (SD) followed by a multiple dose component (MD). In the single dose component, each subject received one subcutaneous dose of study drug, which was followed by a 4 week observation period. Subjects who completed the single dose component and the observation period of the study were continued in the multiple dose component of the study. Additional subjects were recruited for the multiple dose component of the study only. The multiple dose period was following by a post-treatment evaluation period (PD).

During the multiple dose component, subjects from the single dose component of the study continued to receive the study drug (ISIS 301012 or placebo) to which they had previously been randomized. During the first week of the multiple dose treatment period, subjects received three intravenous doses at their respective cohort dose levels on alternate days followed by a single weekly subcutaneous dose for three weeks. This dosing regimen resulted in estimated tissue concentrations that were approximately 70 to 80% of steady state levels.

On Day SD1 (day 1 of single dose period), blood for a lipid panel (total cholesterol, LDL-cholesterol, HDL-cholesterol, VLDL-cholesterol, Apolipoprotein B, triglyceride, lipoprotein(a) and high-sensitivity CRP) was collected following an overnight fast (at least 12 hours). These measurements represent baseline measurements. Study drug was administered via a subcutaneous injection (s.c.) with the end of the injection designated as Time 0 (t=zero). Blood samples for pharmacokinetic (PK) analysis were collected at the following timepoints: 0.5, 1, 1.5, 2, 3, 4, 6, 8, and 12 hrs after study drug administration. Urine samples for PK analysis were collected over a 24 hour period, beginning at Time 0 (t=zero) on Day SD1 and ending on Day SD2. On SD4, blood samples were collected for PK analysis and lipid panel analysis.

Individual cohort treatments for the single dose administration period are summarized in Table 4. The subjects in the placebo group receive the same injection volume as in the Cohort to which they were assigned.

TABLE 4

| Single Dose Treatment Period | | |
|---|---|---|
| Total Dose | # Subjects | All SQ injections at 250 mg/mL SD1 |
| Placebo | 7 | According to cohort |
| 50 mg | 8 | 1 injection, 0.2 mL |
| 100 mg | 8 | 1 injection, 0.4 mL |
| 200 mg | 9 | 1 injection, 0.8 mL |
| 400 mg | 4 | 2 injections, 0.8 mL |

During the multiple dose component, study drug was administered intravenously as a 2-hour infusion on Days MD1, MD3 and MD5 of Week 1 and as a subcutaneous injection(s) of no more than 200 mg per injection on Days MD8, MD15 and MD22. All subjects were required to fast for at least 12 hours before the blood sampling for the lipid panel on MD1, MD8, MD15, MD22, MD25, PD14, PD30, and, if applicable, on Days PD44, PD58, PD72, and PD86.

On Day MD1 (day 1 of multiple dose period), study drug was administered via a 2-hour intravenous (i.v.) infusion with the start of the infusion designated Time 0 (t=zero). Blood samples for pharmacokinetic (PK) analysis were collected 0.5, 1, 2, 2.25, 2.5, 3, 4, 6, and 8 hrs after start of study drug infusion. The 2 hour PK sampling was collected just prior to the end of study drug infusion. In addition, a 24-hour urine collection was performed beginning at Time 0 (t=zero) for PK analysis.

On Days MD3 and Day MD5, study drug was administered via intravenous infusion and blood samples for PK analysis were collected 5 minutes prior to the start of study drug infusion and 2 hours after the start of study drug infusion.

On Days MD2, MD4, MD6, blood samples for PK were collected 24 hours after the start of study drug infusion.

On Days MD8, MD15, study drug was administered via subcutaneous injection. Blood samples for PK analysis and urine samples for urinalysis were collected.

On Day MD22, study drug was administered via subcutaneous injection. Blood samples for PK analysis were collected prior to and 0.5, 1, 1.5, 2, 3, 4, 6, 8, and 12 hours after study drug administration. A urine sample for urinalysis was collected over a 24 hour period, beginning at time of dosing on Day MD22 and ending on Day MD23.

On Day MD23, blood samples for PK were collected 24 hours after dosing of the study drug on Day MD22.

On Day MD25, 3 days after the final dose on Day MD22, blood samples were collected for PK analysis.

Shown in Table 5 is a summary of the dosing schedule for the multiple dose period. The 50 mg and 200 mg groups each had one less subject than during the single dose period. The subjects in the placebo group receive the same injection volume as in the Cohort to which they were assigned.

TABLE 5

Multiple Dose Treatment Period

| Dose | # Subjects | Loading Week—All 2 hour I.V. infusions | | | Once a Week Dosing—SQ Injections at 250 mg/mL | | |
|---|---|---|---|---|---|---|---|
| | | MD1 | MD3 | MD5 | MD8 | MD15 | MD22 |
| Placebo | 7 | N/A | N/A | N/A | According to cohort | | |
| 50 mg | 7 | 50 mg | 50 mg | 50 mg | 1 inj, 0.2 mL | 1 inj, 0.2 mL | 1 inj, 0.2 mL |
| 100 mg | 8 | 100 mg | 100 mg | 100 mg | 1 inj, 0.4 mL | 1 inj, 0.4 mL | 1 inj, 0.4 mL |
| 200 mg | 8 | 200 mg | 200 mg | 200 mg | 1 inj, 0.8 mL | 1 inj, 0.8 mL | 1 inj, 0.8 mL |
| 400 mg | 2 | 400 mg | 400 mg | 400 mg | 2 inj, 0.8 mL | 2 inj, 0.8 mL | 2 inj, 0.8 mL |

During the post-treatment evaluation period, on Days PD14 (or PD39, 39 days since MD1), and PD30 (or PD55, 55 days since MD1) blood samples were collected for lipid panel and PK analysis. All subjects who had fasting total serum cholesterol levels less than or equal to 90% of their baseline values on PD30 continued in an extended follow-up period. Fasting lipid panel measurements were made every 2 weeks until PD86 (or PD111, 111 days past MD1) or until total serum cholesterol levels returned to greater than 90% of baseline. On Days PD44, PD58, PD72, and PD 86 (or PD69, PD83, PD97 and PD111, respectively), blood samples were collected for lipid panel and PK analysis.

Pharmacodynamic Analysis

The pharmacodynamic effects of ISIS 301012 were assessed by comparing parameter levels at the start of treatment to those following multiple doses of ISIS 301012; these data are shown in the following tables. Data are presented as mean percent change from baseline, where the baseline is either the respective parameter measurement made on the first day of the first dose of study drug administered, which was either the first day of the single dose treatment period (SD1) or the first day of the multiple dose treatment period (MD1). The baseline value to which the data were normalized is indicated for each Table. The baseline values were set at 100%, and values above or below 100% indicate an increase or decrease, respectively, in the parameter measured. Data are presented for parameter measurements made during the multiple dose periods, for example, MD8 indicates a measurement made 8 days following administration of the first dose during the multiple dose periods. Also shown are data from parameter measurements made during the post-treatment evaluation period, for example, a measurement on day PD39 was made on the 14$^{th}$ day of the post-treatment evaluation period, which is equivalent to 39 days following the first administration of the first dose during the multiple dose period. Where present, "ND" indicates that the particular measurement is "not determined". Analyses of other serum biomarkers revealed no clinical adverse event trends, including no changes in white blood cell count, platelet count or renal function. Furthermore, no toxicities were observed following administration of ISIS 301012.

Non-compartmental pharmacokinetic analysis of ISIS 301012 was carried out on each individual subject data set. Plasma concentrations of ISIS 301012 were measured by hybridization-based ELISA at PPD Development (Richmond, Va.). The maximum observed drug concentration ($C_{max}$) and the time taken to reach $C_{max}$ ($T_{max}$) were obtained directly from the concentration-time data. The plasma disposition half-life ($t_{1/2\lambda z}$) associated with the apparent terminal elimination phase was calculated from the equation, $t_{1/2\lambda z}=0.693/\lambda_z$, where $\lambda_z$ is the terminal rate constant associated with the apparent terminal elimination phase. The terminal elimination rate constant is calculated using log-linear regression of the last 3 or more concentration time points. The apparent distribution half-life was calculated from a similar equation, using the apparent distribution rate constant in place of the terminal elimination rate constant. The apparent distribution rate constant is calculated using log-linear regression of distribution phase time points. Following single dosing, an area under the plasma concentration-time curve from zero time (pre-dose) to infinite time (AUC∞) was calculated using the linear trapezoidal rule and extrapolation to infinity by dividing the final measurable concentration ($C_{last}$) by $\lambda_z$. Following multiple dosing, the area under the plasma concentration-time curve during the time of each dosing interval (tau, τc) at steady-state ($AUC_\tau$) was calculated using the linear trapezoidal rule. Further, partial areas under the plasma concentration-time curve from zero time (pre-dose) to selected times (t) after the start of the intravenous infusion or subcutaneous administration ($AUC_\tau$) was calculated using the linear trapezoidal rule. Plasma clearance (CL) was calculated from CL=Actual Dose/$AUC_{iv}$. Steady-state volume of distribution [$V_{ss}$=($AUMC_{iv}$*Actual Dose)/($AUC_{iv}$)$^2$; where $AUMC_{iv}$ is the area under the first moment curve following intravenous infusion] was also calculated. Mean absorption time following subcutaneous injection was calculated by subtracting the plasma $AUMC_{sc}$ (first moment curve for subcutaneous injection) from $AUMC_{iv}$ (first moment curve for intravenous infusion) estimated for each subject, and refers to the extent to which ISIS 301012 was distributed throughout the body at steady state concentrations. In addition, ratios of subcutaneous over intravenous plasma AUC were used to estimate subcutaneous plasma bioavailability (F) for each subject.

The amount of ISIS 301012 and total oligonucleotide excreted in the urine was determined from the following expression:

$$Ae_t = C_{urine} \times V_{urine}$$

where $Ae_t$ is the amount excreted up to some fixed time t (i.e., 24 hours), $C_{urine}$ is the urine concentration of the analyte, and $V_{urine}$ is the total urine volume. The percentage of the administered dose excreted in urine (intact or as total oligonucleotide) was then calculated from the following expression:

$$\% \text{ Dose Excreted} = (Ae_t/\text{Administered dose}) \times 100\%$$

Pharmacokinetic Summary

The plasma pharmacokinetic profile of ISIS 301012 was determined from blood sampling following the first 2-hr intravenous infusion (MD1), and is summarized in Table 6. Data are presented as mean±standard deviation for each dose group. $C_{max}$=maximal plasma concentration; $T_{max}$=time to reach $C_{max}$; $AUC_{0-48hr}$=area under the plasma concentration-time curve from time 0 to 48 hours after the start of dose administration; CL=plasma clearance; $V_{ss}$=steady-state volume of distribution. Bioavailability following an intravenous administration is assumed to be 100%.

TABLE 6

ISIS 301012 Dosed Intravenously: Plasma Pharmacokinetics

| | Dose Group | | | |
|---|---|---|---|---|
| | 50 mg | 100 mg | 200 mg | 400 mg |
| Dose, mg/kg for 70 kg | 0.7 ± 0.1 | 1 ± 0.1 | 2.7 ± 0.5 | 5.9 ± 1.2 |
| N | 8 | 8 | 8 | 3 |

TABLE 6-continued

ISIS 301012 Dosed Intravenously: Plasma Pharmacokinetics

| | Dose Group | | | |
|---|---|---|---|---|
| | 50 mg | 100 mg | 200 mg | 400 mg |
| $C_{max}$ (ug/ml) | 5 ± 1 | 9 ± 1 | 22 ± 4 | 38 ± 5 |
| $T_{max}$ (hr) | 2 ± 0.1 | 2 ± 0.1 | 2 ± 0.2 | 2 ± 0.2 |
| $AUC_{0-48\,hr}$ (ug * hr/mL) | 11 ± 3 | 24 ± 3 | 68 ± 14 | 148 ± 14 |
| CL (L/hr) | 5 ± 1 | 4 ± 0.6 | 3 ± 0.7 | 3 ± 0.3 |
| $V_{ss}$ (L) | 6 ± 3 | 7 ± 1 | 7 ± 1 | 8 ± 0.8 |
| Apparent Distribution $t_{1/2}$ (hr) | 0.7 ± 0.1 | 0.8 ± 0.1 | 1 ± 0.2 | 1.7 ± 0.4 |

Dose-dependent maximum plasma concentrations ($C_{max}$) following 2-hour intravenous infusions were seen at the end of infusion followed by a biphasic decline. An initial, relatively fast distribution phase (mean apparent distribution half-life ranged 0.7 to 1.7 hours) dominated the plasma clearance and was followed by a slower apparent elimination phase.

Plasma pharmacokinetics determined from blood sampling following the final subcutaneous injection (MD22) are summarized in Table 7. Data are presented as mean±standard deviation. $C_{max}$=maximal plasma concentration; $T_{max}$=time to reach $C_{max}$; $AUC_{0-48hr}$=area under the plasma concentration-time curve from time 0 to 48 hours after the start of dose administration; $AUC_{0-\infty\,at\,ss}$=area under the plasma concentration-time curve from time 0 to infinity at steady-state; % BAV=plasma bioavailability (%) following subcutaneous administration.

TABLE 7

ISIS 301012 Dosed Subcutaneously: Plasma Pharmacokinetics

| | Dose Group | | | |
|---|---|---|---|---|
| | 50 mg | 100 mg | 200 mg | 400 mg |
| Dose, mg/kg for 70 kg | 0.7 ± 0.1 | 1.3 ± 0.1 | 2.7 ± 0.5 | 5.9 ± 1.2 |
| N | 7 | 8 | 8 | 2 |
| $C_{max}$ (ug/ml) | 1 ± 0.3 | 2 ± 1 | 3 ± 1 | 7 |
| $T_{max}$ (hr) | 4 ± 2 | 4 ± 2 | 3 ± 2 | 7 |
| $AUC_{0-48\,hr}$ (ug * hr/mL) | 8 ± 2 | 18 ± 4 | 35 ± 7 | 109 |
| $AUC_{0-\infty\,at\,ss}$ (ug * hr/mL) | 19 ± 9 | 28 ± 5 | 63 ± 13 | 160 |
| Apparent Distribution $t_{1/2}$ (hr) | 4 ± 1 | 5 ± 3 | 7 ± 3 | 8 |
| Elimination $t_{1/2}$ (hr) | 23 ± 1 | 27 ± 12 | 31 ± 11 | 47 |
| % BAV | 69 ± 9 | 76 ± 18 | 54 ± 11 | 78 |

The mean time to maximum plasma concentrations ($T_{max}$) following the final subcutaneous injection (MD22) of ISIS 301012 was approximately 4 hours following administration of the 50 and 100 mg doses, and approximately 3 hours following administration of the 200 mg dose. Plasma concentrations decreased more slowly from the maximum plasma concentration ($C_{max}$) following subcutaneous injection, when compared to intravenous infusion, indicating continued absorption of ISIS 301012 after achievement of $C_{max}$. Maximum plasma concentrations ($C_{max}$) ranged from approximately 1 to 3 ug/mL (50 mg to 200 mg) and were dose-dependent over the studied subcutaneous dose range, but were much lower in comparison to equivalent intravenous infusion doses. $C_{max}$, $T_{max}$, plasma AUC following the first subcutaneous dose of ISIS 301012 were similar to those shown in Table 7, following the final subcutaneous dose. Plasma drug concentration was decreased by at least 10 fold by 24 hours. The terminal elimination phase observed in plasma provided a measure of tissue elimination rate, thus the elimination half-life represents the time at which approximately 50% of ISIS 301012 was cleared from tissues. Characterization of the terminal elimination phase yielded an elimination half-life of approximately 23 (±1) to 31 (±11) days (see Table 7). This result is consistent with the slow elimination of ISIS 301012 observed from monkey tissues, and thus appears to reflect an equilibrium of oligonucleotide between plasma and tissue. Absolute plasma bioavailability (BAV) of ISIS 301012 following subcutaneous administration ranged from 54% to 78%, in comparison to intravenous infusion, and was independent of dose. Plasma BAV may underestimate the ultimate complete absorption of ISIS 301012, as nonhuman primate studies have shown that the entire dose is ultimately distributed to tissues such that there is no difference between intravenous and subcutaneous administration with regard to end organ drug concentrations.

Mean urinary excretion of total oligonucleotide was less than 8% within the first 24 hours. Excretion of chain shortened metabolites was evident. Urine excretion data indicate that ISIS 301012 is primarily distributed to tissues. Ultimate elimination is a combination of nuclease metabolism and excretion in urine.

Exposure-Response Relationships

The correlation between ISIS 301012 plasma concentrations, serum Apolipoprotein B protein and LDL-cholesterol is shown in Table 8. Serum Apolipoprotein B, LDL-cholesterol and total cholesterol are presented as percentage of baseline. The numbers in parentheses following Apolipoprotein B percent baseline indicates the number of samples used to calculate the mean; all other means were calculated using the number of samples in the "N" column.

TABLE 8

Exposure-Response Relationship: ISIS 301012 Plasma Level, Apolipoprotein B protein and LDL-cholesterol in 200 mg treatment group

| Study Day | N | ISIS 301012 ng/mL | Apolipoprotein B % Baseline | LDL-Cholesterol % Baseline | Total Cholesterol % Baseline |
|---|---|---|---|---|---|
| MD1 | 9 | 0.5 | 96 | 93 | 99 |
| MD8 | 8 | 18 | 92 | 86 | 90 |
| MD15 | 8 | 16 | 68 | 71 | 77 |
| MD22 | 8 | 21 | 66 | 68 | 76 |
| MD25 | 8 | 30 | 50 | 69 | 76 |
| PD39 | 8 | 15 | 61 | 65 | 74 |
| PD55 | 8 | 8.7 | 58 | 66 | 76 |
| PD69 | 6 | 6.1 | 64 | 73 | 76 |
| PD83 | 7 | 5.2 | 70 | 79 | 83 |
| PD97 | 5 | 4.7 | 76 (7) | 82 | 87 |
| PD111 | 4 | 5.1 | 77 (6) | 80 | 81 |

As shown in Table 8, total tissue exposure, represented by ISIS 301012 plasma concentrations (measured at least 72 hr after dosing during and following the multiple dose treatment period) was highly correlated with serum Apolipoprotein B protein levels and LDL-cholesterol levels, both of which responded in similar dose-response manners. Increases in plasma AUC were slightly greater than dose-proportional. Significant reduction in Apolipoprotein B protein (p<0.02) from baseline for the 200 mg treatment group was achieved from Day 15 (MD 15) to Day 97 (PD 72, or 75 days after last dose), consistent with the slow elimination of ISIS 301012 in plasma (terminal elimination $t_{1/2}$ of approximately 31 days).

A comparison of serum reductions versus plasma trough AUC for 26 ISIS 301012-treated subjects at the end of the multiple dosing period (MD25) revealed a direct correlation between trough AUC and the observed reductions in serum Apolipoprotein B protein levels, LDL-cholesterol and total cholesterol (r≥0.67, p≤0.0002). Such a correlation is consistent with the fact that trough AUC is a representation of liver concentrations, as result of the equilibrium reached between drug concentration in plasma and in liver. A correlation was also observed between plasma trough concentrations and serum reductions, when plasma trough concentrations ($C_{trough}$; mean trough concentration determined from plasma levels just prior to dosing on days MD15 and MD22) were compared to reductions in serum Apolipoprotein B, serum LDL-cholesterol, and serum total cholesterol. $C_{trough}$ and trough AUC correlate with reductions in lipid parameters, demonstrating that as exposure to ISIS 301012 increased, serum Apolipoprotein B, LDL-cholesterol and total cholesterol decreased.

The relationship between serum Apolipoprotein B protein levels and plasma trough concentrations of ISIS 301012 is described with a sigmoidal inhibitory effect $E_{max}$ model using the data collected 3 days post dosing. The estimated plasma $EC_{50}$ and predicted liver concentrations based on prior non-human primate studies were 18 (±2) ng/mL and 60 ug/g, respectively. Plasma trough concentration increases following multiple doses of ISIS 301012, reflecting accumulation of ISIS 301012 in the liver; were 2-fold following the loading dose of ISIS 301012, and 5-fold following the final dose of ISIS 301012. Monkey and human plasma pharmacokinetics for ISIS 301012 are essentially superimposable at mg/kg equivalent doses. Utilizing these known PK similarities, measurement of drug concentrations in the terminal elimination phase in human clinical studies can be used to assess accumulation in liver. Such estimates are shown in Table 9. ISIS 301012 liver concentrations are estimated based on monkey data. Monkey average plasma concentrations represent an average from 6 animals and were measured 48 to 72 hours after the last dose in a 13 week repeat dose toxicology study (e.g. the study described in Example 2, above). Human plasma trough concentration data was obtained 72 hours after the last intravenous loading dose; the number of study subjects is indicated in parentheses. Monkey liver concentrations represent an average of 4-6 animals and were measured in tissues collected 48 hours after the last dose in a 13 week repeat dose toxicology study.

TABLE 9

ISIS 301012: Monkey and Human Plasma Pharmacokinetics

| Dose/Route Monkey | Plasma $C_{trough}$ (ng/mL) | Actual Liver Conc. (µg/g) |
|---|---|---|
| 3.5 mg/kg/week/i.v. | 28 | 100 ± 59 |
| 7 mg/kg/week/i.v. | 107 | 293 ± 105 |
| 21 mg/kg/week/i.v. | 292 | 584 ± 129 |
| 35 mg/kg/week/s.c. | 570 | 1129 ± 242 |

| Human | Plasma $C_{trough}$ (ng/mL) | Estimated Liver Conc. (µg/g) |
|---|---|---|
| 50 mg/week/i.v./s.c. | 24 (n = 5) | 10 |
| 100 mg/week/i.v./s.c. | 8 (n = 3) | 28 |
| 200 mg/week/i.v./s.c. | 18 (n = 6) | 60 |
| 400 mg/week/i.v./s.c. | 40 (n = 2) | 150 |

Plasma trough AUC for the 50 mg, 100 mg, 200 mg and 400 mg dose groups was found to be 3, 5, 12 and 18 µg · hr/mL, respectively, on MD25 (three days following the final dose during the multiple dosing period).

Example 4

Antisense Inhibition of ApoB Reduces Plasma ApoC-III and Apo-CIII-Containing Lipoproteins A randomized, double-blind, placebo controlled, parallel group clinical trial was performed to evaluate the effect of ISIS 301012 (Mipomersen) on hypercholesterolemic subjects.

Subjects were chosen to comply with the following eligibility criteria: age between 18-65 years; fasting levels of LDL-C≥130 mg/dl; fasting levels of TG<400 mg/dl; Body Mass Index (BMI) between 25-32.

ISIS 301012 or control placebo was administered to subjects as shown in Table 10.

TABLE 10

Summary of Cohorts

| Cohort | N (No. of Subjects) | ISIS 301012 Doses |
|---|---|---|
| A | 8 | 200 mg × 4 load during 11 days, followed by 200 mg every other week × 11 weeks |
| B | 8 | 200 mg × 4 load during 11 days, followed by 100 mg every other week × 11 weeks |
| C | 8 | 200 mg every week × 13 weeks |
| D | 8 | 300 mg every week × 13 weeks |
| Placebo | 8 | Placebo was administered to 2 subjects from each of Cohorts A-D |

Group A received a slow loading phase, during which 4 doses of 200 mg ISIS 301012 are administered over 11 days. This slow loading phase is followed by an 11 week maintenance phase, during which a 200 mg dose of ISIS 301012 is administered every other week.
Group B received a slow loading phase, during which 4 doses of 200 mg ISIS 301012 are administered over 11 days. This slow loading phase is followed by an 11 week maintenance phase, during which a 100 mg dose of ISIS 301012 is administered every other week.
Group C receives a maintenance phase only, during which a 200 mg dose of ISIS 301012 is administered once weekly for 13 weeks.
Group D receives a maintenance phase only, during which a 300 mg dose of ISIS 301012 is administered once weekly for 13 weeks.

After administration of ISIS 301012 to the subjects, plasma samples from the subjects in Cohorts A, C and D were tested (samples from Cohort B were not tested). ApoB, ApoC-III, ApoE, TG, and cholesterol levels were measured in plasma and plasma-derived lipoproteins from the subjects.

Pharmacokinetic Parameters

After administration of ISIS 301012 to the subjects, plasma levels and pharmacokinetic (PK) parameters of ISIS 301012 were determined in the subjects in Cohorts A, C and D as shown in Tables 11-15.

Pharmacokinetic parameters were obtained from plasma drug concentration-time profiles. Serial blood samples were collected prior to, during and following the last s.c. dose on Day 85 to determine PK parameters. Subjects also had blood drawn for the determination of ISIS 301012 concentrations at various time points during the 13-week treatment period. Two subjects stopped treatment early (Subject 104 in Cohort A and Subject 403 in Cohort D), and plasma concentration-time profiling samples on Day 85 were not collected for these two subjects.

Blood was collected in tubes containing EDTA as the anti-coagulant for plasma drug concentration analysis. Plasma samples were stored frozen at −70° C. until plasma samples shipped to PPD (Richmond, Va.) via overnight freight on dry ice. Samples were stored frozen at −60 to −90° C. at the bioanalytical lab until analysis for oligonucleotide concentration using a validated hybridization ELISA. Analysis was performed based on the principles and requirements described in 21 CFR part 58 of United States Food and Drug Administration Good Laboratory Practice guidelines (PPD Project KMP; Isis Study No. 301012-CS3BA01, herein incorporated by reference).

Briefly, the hybridization ELISA/cutting procedure is a non-competitive immunoassay. In this assay, hybridization of the complementary sequence to ISIS 301012 containing biotin at the 5' end and digoxigenin at the 3' end (i.e., the detection probe) to ISIS 301012 in plasma occurs, with the hybridized complex subsequently immobilized onto a neutravidin coated plate. This detection probe contained five LNA nucleotides on the 5'-end of the sequence to improve hybridization with ISIS 301012. S1 nuclease is then added to the plate and incubated at 37° C. for 1 hour to cleave any remaining unhybridized detection probe. The measurement of hybridized complex (which is digoxigenin-labeled) attached to the plate is then performed following the addition of anti-digoxigenin conjugated to alkaline phosphatase, which catalyzes the formation of fluorescent AttoPhos®. The reaction is stopped by adding EDTA sodium (20%) and the fluorescence intensity is measured using a fluorescent plate reader.

The calibration range of the assay was 0.228 to 30.4 ng/mL for ISIS 301012 in plasma, with the low end of this range defining the lower limit of quantitation (LLOQ). The precision at the lower limit of quantification was within 25%, and the accuracy at lower limit of quantification was within 25% of the nominal concentration. The precision at the low, mid, high, and upper limit of quantification levels was within 20%, and the accuracy at low, mid, high, and upper limit of quantification levels was within 20% of the nominal concentration. Samples with concentrations previously observed or expected to be above the upper level of quantitation (ULOQ) were diluted within the range using a suitable volume of blank human plasma prior to analysis. All study samples were analyzed within the established stability timeframe, which was established by analyzing stability samples stored under the same conditions as study samples of approximately 365 days at −80° C.

Plasma pharmacokinetics for ISIS 301012 were analyzed using non-compartment methods with WinNonLin Professional Version 5.2 software (Pharsight Corp., Mountain View, Calif.). $C_{max}$ was the maximum concentration observed in plasma. $T_{max}$ was the time at which $C_{max}$ occurred. Area under the plasma concentration-time curve (AUC) was calculated using the linear trapezoidal rule from 0 to 48 hours and from 0 to 168 hours (weekly dosing interval, t) following dose administration (partial area, $AUC_{0-48hr}$ and $AUC_{0-\tau}$). When calculating partial areas, linear interpolation was done to estimate the corresponding concentration if the ending times did not coincide with an observed data point. Plasma elimination half-life for ISIS 301012 was calculated from the equation, $t_{1/2\lambda_z}=0.693/\lambda_z$, where $\lambda_z$ is the rate constant associated with the terminal elimination phase. A minimum of three data points were used to define $\lambda_z$ and the correlation of determination values (rsq) had to be at or greater than 0.8 for the estimate to be accepted.

Trough plasma concentrations ($C_{trough}$) at 168 hr from previous dose were determined throughout the 13-week treatment period.

BLQ values (below the limit of quantitation) (a total of 2 observations) were treated as "missing" in the pharmacokinetic analyses.

Ideal body weight (IBW) was calculated based on the following equations:

Males: IBW(kg)=1.1×($HT$−152)+48

Females: IBW(kg)=0.9×($HT$−152)+45

Where, HT is subject height in centimeters.

Body mass index (BMI) was calculated based on the following equation:

BMI(kg/m$^2$)=10000×($WT/HT^2$)

Where, HT is subject height in centimeters, WT is subject weight in kilograms.

Plasma concentrations and pharmacokinetic parameters were summarized using descriptive statistics (WinNonlin Professional, Version 5.2). Nominal time was used when summarizing plasma concentration-time profiles by descriptive statistics. BLQ values (below the limit of quantitation) (a total of 2 observations) were treated as "missing" in the calculation of descriptive statistics.

TABLE 11

Summary of ISIS 301012 Concentrations (μg/mL) in Plasma during and following Weekly Doses of 100 mg Administered Subcutaneously in Hypercholesterolemic Subjects

| Co-hort | Weekly Dose | Study Day | Time Point (hr) | N | ISIS 301012 Conc. (μg/mL) (Mean ± SD) | (SE) |
|---|---|---|---|---|---|---|
| A | 100 mg* | 4 | 72 | 7 | 0.00353 ± 0.00120 | 0.00045 |
| | | 8 | 96 | 7 | 0.00659 ± 0.00182 | 0.00069 |
| | | 14 | 72 | 7 | 0.0122 ± 0.0049 | 0.0018 |
| | | 15 | 96 | 7 | 0.0112 ± 0.0041 | 0.0015 |
| | | 22 | 168 | 7 | 0.0106 ± 0.0027 | 0.0010 |
| | | 36 | 168 | 7 | 0.0107 ± 0.0036 | 0.0014 |
| | | 50 | 168 | 7 | 0.0102 ± 0.0046 | 0.0017 |
| | | 64 | 168 | 7 | 0.0105 ± 0.0036 | 0.0014 |
| | | 78 | 168 | 7 | 0.0108 ± 0.0036 | 0.0013 |
| | | 85 | 0 | 7 | 0.00795 ± 0.00296 | 0.00112 |
| | | 85 | 0.5 | 7 | 0.823 ± 0.388 | 0.147 |
| | | 85 | 1 | 7 | 1.41 ± 0.45 | 0.17 |
| | | 85 | 1.5 | 7 | 1.55 ± 0.44 | 0.17 |
| | | 85 | 2 | 7 | 1.81 ± 0.54 | 0.20 |
| | | 85 | 3 | 7 | 2.22 ± 0.55 | 0.21 |
| | | 85 | 4 | 7 | 2.16 ± 0.43 | 0.16 |
| | | 85 | 6 | 7 | 1.55 ± 0.29 | 0.11 |
| | | 85 | 8 | 7 | 1.28 ± 0.31 | 0.12 |
| | | 85 | 12 | 7 | 0.919 ± 0.244 | 0.092 |
| | | 86 | 24 | 7 | 0.0731 ± 0.0445 | 0.0168 |
| | | 87 | 48 | 7 | 0.0147 ± 0.0033 | 0.0012 |
| | | 88 | 72 | 7 | 0.0132 ± 0.0023 | 0.0009 |
| | | 92 | 168 | 7 | 0.0116 ± 0.0041 | 0.0015 |
| | | 99 | 336 | 7 | 0.0127 ± 0.0080 | 0.0030 |
| | | 115 | 720 | 7 | 0.0107 ± 0.0071 | 0.0027 |
| | | 145 | 1440 | 7 | 0.00910 ± 0.01034 | 0.00391 |
| | | 175 | 2160 | 7 | 0.00803 ± 0.01048 | 0.00396 |
| | | 205 | 2880 | 7 | 0.00489 ± 0.00689 | 0.00261 |
| | | 235 | 3600 | 7 | 0.00314 ± 0.00338 | 0.00128 |
| | | 265 | 4320 | 6 | 0.00264 ± 0.00262 | 0.00107 |

*200 mg administered every other week.

TABLE 12

Summary of ISIS 301012 Concentrations (μg/mL) in Plasma during and following Weekly Doses of 200 mg Administered Subcutaneously in Hypercholesterolemic Subjects

| Co-hort | Weekly Dose | Study Day | Time Point (hr) | N | ISIS 301012 Conc. (μg/mL) (Mean ± SD) | (SE) |
|---|---|---|---|---|---|---|
| C | 200 mg | 8 | 168 | 8 | 0.00330 ± 0.00105 | 0.00037 |
| | | 15 | 168 | 8 | 0.00573 ± 0.00205 | 0.00072 |
| | | 22 | 168 | 8 | 0.00815 ± 0.00287 | 0.00101 |
| | | 36 | 168 | 8 | 0.0125 ± 0.0060 | 0.0021 |
| | | 50 | 168 | 8 | 0.0178 ± 0.0086 | 0.0030 |
| | | 64 | 168 | 8 | 0.0240 ± 0.0138 | 0.0049 |
| | | 78 | 168 | 8 | 0.0325 ± 0.0223 | 0.0079 |
| | | 85 | 0 | 8 | 0.0365 ± 0.0257 | 0.0091 |
| | | 85 | 0.5 | 8 | 0.806 ± 0.316 | 0.112 |
| | | 85 | 1 | 8 | 1.56 ± 0.44 | 0.15 |

TABLE 12-continued

Summary of ISIS 301012 Concentrations (μg/mL) in Plasma during and following Weekly Doses of 200 mg Administered Subcutaneously in Hypercholesterolemic Subjects

| Co-hort | Weekly Dose | Study Day | Time Point (hr) | N | ISIS 301012 Conc. (μg/mL) (Mean ± SD) | (SE) |
|---|---|---|---|---|---|---|
| | | 85 | 1.5 | 8 | 1.87 ± 0.55 | 0.19 |
| | | 85 | 2 | 8 | 2.32 ± 0.77 | 0.27 |
| | | 85 | 3 | 8 | 2.64 ± 0.95 | 0.33 |
| | | 85 | 4 | 8 | 2.68 ± 0.96 | 0.34 |
| | | 85 | 6 | 8 | 2.09 ± 0.67 | 0.24 |
| | | 85 | 8 | 8 | 1.90 ± 0.56 | 0.20 |
| | | 85 | 12 | 8 | 1.07 ± 0.13 | 0.05 |
| | | 86 | 24 | 8 | 0.138 ± 0.063 | 0.022 |
| | | 87 | 48 | 8 | 0.0498 ± 0.0333 | 0.0118 |
| | | 88 | 72 | 8 | 0.0474 ± 0.0358 | 0.0127 |
| | | 92 | 168 | 8 | 0.0468 ± 0.0374 | 0.0132 |
| | | 99 | 336 | 7 | 0.0284 ± 0.0210 | 0.0079 |
| | | 115 | 720 | 8 | 0.0407 ± 0.0386 | 0.0136 |
| | | 145 | 1440 | 8 | 0.0244 ± 0.0255 | 0.0090 |
| | | 175 | 2160 | 8 | 0.0222 ± 0.0258 | 0.0091 |
| | | 205 | 2880 | 8 | 0.0121 ± 0.0106 | 0.0038 |
| | | 235 | 3600 | 8 | 0.00699 ± 0.00522 | 0.00184 |
| | | 265 | 4320 | 8 | 0.00395 ± 0.00276 | 0.00098 |

TABLE 13

Summary of ISIS 301012 Concentrations (μg/mL) in Plasma during and following Weekly Doses of 300 mg Administered Subcutaneously in Hypercholesterolemic Subjects

| Co-hort | Weekly Dose | Study Day | Time Point (hr) | N | ISIS 301012 Conc. (μg/mL) (Mean ± SD) | (SE) |
|---|---|---|---|---|---|---|
| D | 300 mg | 8 | 168 | 7 | 0.00475 ± 0.00099 | 0.00037 |
| | | 15 | 168 | 7 | 0.00711 ± 0.00176 | 0.00067 |
| | | 22 | 168 | 7 | 0.0112 ± 0.0026 | 0.0010 |
| | | 36 | 168 | 7 | 0.0154 ± 0.0029 | 0.0011 |
| | | 50 | 168 | 7 | 0.0208 ± 0.0028 | 0.0011 |
| | | 64 | 168 | 7 | 0.0233 ± 0.0079 | 0.0030 |
| | | 78 | 168 | 7 | 0.0260 ± 0.0078 | 0.0029 |
| | | 85 | 0 | 7 | 0.0261 ± 0.0048 | 0.0018 |
| | | 85 | 0.5 | 7 | 1.44 ± 0.44 | 0.17 |
| | | 85 | 1 | 7 | 2.82 ± 1.64 | 0.62 |
| | | 85 | 1.5 | 7 | 3.16 ± 1.95 | 0.74 |
| | | 85 | 2 | 7 | 3.31 ± 1.51 | 0.57 |
| | | 85 | 3 | 7 | 4.21 ± 2.51 | 0.95 |
| | | 85 | 4 | 7 | 3.96 ± 1.99 | 0.75 |
| | | 85 | 6 | 7 | 3.03 ± 1.25 | 0.47 |
| | | 85 | 8 | 7 | 2.93 ± 0.94 | 0.35 |
| | | 85 | 12 | 7 | 1.97 ± 0.45 | 0.17 |
| | | 86 | 24 | 7 | 0.193 ± 0.126 | 0.048 |
| | | 87 | 48 | 7 | 0.0449 ± 0.0171 | 0.0065 |
| | | 88 | 72 | 7 | 0.0348 ± 0.0094 | 0.0036 |
| | | 92 | 168 | 7 | 0.0338 ± 0.0077 | 0.0029 |
| | | 99 | 336 | 7 | 0.0230 ± 0.0077 | 0.0029 |
| | | 115 | 720 | 7 | 0.0176 ± 0.0087 | 0.0033 |
| | | 145 | 1440 | 6 | 0.0112 ± 0.0060 | 0.0025 |
| | | 175 | 2160 | 6 | 0.00873 ± 0.00522 | 0.00213 |
| | | 205 | 2880 | 6 | 0.00647 ± 0.00359 | 0.00146 |
| | | 235 | 3600 | 6 | 0.00296 ± 0.00168 | 0.00069 |
| | | 265 | 4320 | 7 | 0.00367 ± 0.00418 | 0.00158 |

N Number of observations
SD Standard deviation of the mean
SE Standard error of the mean
Note:
Subject 104 (Cohort A) and 403 (Cohort D) were not included in the descriptive summary due to their early termination.

TABLE 14

Descriptive Statistical Summary of Pharmacokinetic Parameter Estimates for ISIS 301012 in Hypercholesterolemic Subjects following the last Subcutaneous Injection

| Cohort | Dose (mg/dose) | N | Weekly Dose (mg/week) | $C_{max}$ (μg/ml) | $T_{max}$ (hr) | $AUC_{0-48\,hr}$ (μg*hr/mL) | $AUC_{0-\tau}$ (μg*hr/mL) | $t_{1/2\lambda z}$ (day) |
|---|---|---|---|---|---|---|---|---|
| A | 200 | 7 | 100 | 2.27 ± 0.50 | 3.43 ± 0.54 3 (3 to 4) | 24.6 ± 2.2 | 26.1 ± 2.3 | 45.7 ± 10.9 |
| C | 200 | 8 | 200 | 2.81 ± 0.95 | 3.50 ± 0.53 4 (3 to 4) | 32.1 ± 6.5 | 37.7 ± 10.2 | 46.2 ± 11.2 |
| D | 300 | 7 | 300 | 4.32 ± 2.46 | 4.00 ± 1.82 3 (3 to 8) | 51.0 ± 15.1 | 55.2 ± 15.0 | 47.0 ± 11.7 |

Data are presented as Mean ± Standard Deviation (median (range) is also included for $T_{max}$).

N Number of subjects $C_{max}$ Maximum plasma concentration $T_{max}$ Time $C_{max}$ observed $AUC_{0-48\,hr}$ Partial area under the plasma concentration-time curve from time 0 to 48 hours after dose administration $AUC_{0-\tau}$ Partial area under the plasma concentration-time curve from time 0 to 168 hours (weekly dosing interval) after dose administration $AUC_{0-\infty}$ Area under the plasma concentration-time curve from time 0 to infinity ND Not determined due to PK profiling samples were not collected.

Note:

The PK parameters for Subject 104 (Cohort A) and 403 (Cohort D) were not included in the descriptive summary due to their early termination.

TABLE 15

Descriptive Statistical Summary of Plasma Trough Concentrations (ng/mL) During Treatment

| Cohort | Weekly Dose | Study Day | N | $C_{trough}$ at 168 hr from Previous Dose (ng/mL) Mean ± SD | SE |
|---|---|---|---|---|---|
| A | 100 mg | 22 | 7 | 10.6 ± 2.7 | 1.0 |
|   |        | 36 | 7 | 10.7 ± 3.6 | 1.4 |
|   |        | 50 | 7 | 10.2 ± 4.6 | 1.7 |
|   |        | 64 | 7 | 10.5 ± 3.6 | 1.4 |
|   |        | 78 | 7 | 10.8 ± 3.6 | 1.3 |
|   |        | 92 | 7 | 11.6 ± 4.1 | 1.5 |
| C | 200 mg | 8  | 8 | 3.30 ± 1.05 | 0.37 |
|   |        | 15 | 8 | 5.73 ± 2.05 | 0.72 |
|   |        | 22 | 8 | 8.15 ± 2.87 | 1.01 |
|   |        | 36 | 8 | 12.5 ± 6.0 | 2.1 |
|   |        | 50 | 8 | 17.8 ± 8.6 | 3.0 |
|   |        | 64 | 8 | 24.0 ± 13.8 | 4.9 |
|   |        | 78 | 8 | 32.5 ± 22.3 | 7.9 |
|   |        | 85 | 8 | 36.5 ± 25.7 | 9.1 |
|   |        | 92 | 8 | 46.8 ± 37.4 | 13.2 |
| D | 300 mg | 8  | 7 | 4.75 ± 0.99 | 0.37 |
|   |        | 15 | 7 | 7.11 ± 1.76 | 0.67 |
|   |        | 22 | 7 | 11.2 ± 2.6 | 1.0 |
|   |        | 36 | 7 | 15.4 ± 2.9 | 1.1 |
|   |        | 50 | 7 | 20.8 ± 2.8 | 1.1 |
|   |        | 64 | 7 | 23.3 ± 7.9 | 3.0 |
|   |        | 78 | 7 | 26.0 ± 7.8 | 2.9 |
|   |        | 85 | 7 | 26.1 ± 4.8 | 1.8 |
|   |        | 92 | 7 | 33.8 ± 7.7 | 2.9 |

N Number of subjects
SD Standard deviation of the mean
SE Standard error of the mean
Note:
Subject 104 (Cohort A) and 403 (Cohort D) were not included in the descriptive summary due to their early termination.

ApoC-III Analysis

ApoC-III-containing lipoproteins were separated from plasma by immunoaffinity chromatography (IAC) followed by ultracentrifugation. Immunoaffinity chromatography separation was performed as described by Campos et al. (Distinct patterns of lipoproteins with ApoB defined by presence of ApoE or ApoC-III in hypercholesterolemia and hypertriglyceridemia. J. Lipid Res., 2001, 42:1239-1249, herein incorporated by reference). Blood was drawn from the subjects after a 12-h fast and immediately centrifuged at 4° C. to isolate plasma. A mixture containing 2 µM benzamidine, aprotinin (0.01 mg/ml), PMSF (17.5 µg/ml), and gentamicin (0.05 mg/ml) was added to the plasma and the samples were immediately sealed under $N_2$ and frozen at 80° C. until they were analyzed.

Separation of lipoproteins by ApoE and ApoC-III content was carried out with affinity-purified polyclonal antibodies anti-ApoE (kindly provided by Genzyme, Cambridge, Mass.) and anti-ApoC-III (DMA, Arlington, Tex.), coupled to cyanogen bromide-activated Sephacryl S-1000 resins as previously described by Khoo et al. (Effects of estrogenic oral contraceptives on the lipoprotein B particle system defined by apolipoproteins E and C-III content. J. Lipid Res. 1999 40:202-212, herein incorporated by reference). For each subject 3 ml of plasma was first incubated with 1 ml of anti-ApoE resin for 1 h at room temperature with constant mixing. All incubations and rinses were carried out with disposable Econopac columns (Bio-Rad, Hercules, Calif.). The unbound fractions (E⁻) were collected by gravity flow from the Econopac columns and the resin was washed with PBS. The bound fraction (E⁺) was eluted by incubation with 3 M NaSCN, passed through a gel-filtration column using PBS, and then immediately dialyzed against PBS in microconcentrators (Amicon, Beverly, Mass.). The E⁻ fractions and the dialyzed E⁺ fractions were further incubated with 1.0 ml of anti-ApoC-III resin for 4 h at 4° C. The same elution protocol used for the anti-ApoE resin was carried out to yield four immunofractions, two with ApoE (E⁺C-III⁺, E⁺C-III⁻) and two without ApoE (E⁻C-III⁺, and E⁻C-III⁻).

Each of the four immunofractions was then separated into four density fractions by using a modification of the Lindgren, Jensen, and Hatch method (Lindgren, F. T., L. C. Jensen, and F. T. Hatch. 1972. The isolation and quantitative analysis of serum lipoproteins. In Blood Lipids and Lipoproteins: Quantitation, Composition, and Metabolism, G. J. Nelson, editor. John Wiley-Interscience, New York. 181-274, herein incorporated by reference). The IAC separation procedure was carried out before ultracentrifugation, so that any loss of ApoC-III and ApoE during ultracentrifugation could not affect the separation of particle types by IAC. To separate VLDL subfractions with Svedberg units of flotation ($S_f^o$) 60-400 (light VLDL) and $S_f$ 20-60 (dense VLDL), samples were spun in the outer row of a Beckman (Palo Alto, Calif.) type 25 rotor at 25,000 rpm in an L8-70M instrument (Beckman) for 1 h at 10° C. to collect light VLDL and for 6 h to collect dense VLDL. To separate IDL (d=1.006-1.025 g/ml) and LDL (d=1.025-1.050 g/ml), the density was raised with KBr, and centrifugation was carried out at 25,000 rpm for 24 h each at 10° C. For each subject, a sample was ultracentrifuged after IAC to separate light and dense VLDL, IDL, and LDL. Cholesterol, triglyceride, and ApoB were also measured in samples ultracentrifuged after IAC.

Results

Three dose cohorts, Cohort A, Cohort C, and Cohort D, were analyzed (n=8 each). The doses of ISIS 301012 administered to the subjects in Cohorts C and D, but not Cohort A, reduced plasma total ApoC-III from 14 mg/dL to 6.5 mg/dL (−54%) and 5.3 mg/dL (−62%), respectively (both p<0.01 vs placebo). These doses decreased ApoC-III significantly in VLDL (p<0.01) and trended toward promoting reductions in HDL ApoC-III. All ApoB lipoprotein types studied were reduced relative to placebo. The dose administered to Cohort C produced statistically significant reductions in VLDL and LDL without ApoC-III (p<0.05) and dose administered to Cohort D reduced LDL both with and without ApoC-III. ApoE was decreased slightly in whole plasma (12-14%) both Cohorts C and D, with decreases mainly in HDL, while the ApoE to ApoB ratio in VLDL and LDL (p<0.03) were increased. The doses of ISIS 301012 administered to subject in Cohorts C and D also reduced plasma TG by about 60% (p<0.04) and LDL-C by 66-87% (p<0.01).

Surprisingly, antisense inhibition of ApoB is shown to reduce plasma concentrations of ApoC-III and ApoC-III-containing lipoproteins in a dose-dependent manner. Without being bound to a particular theory, it is hypothesized that either reduced ApoB in hepatocytes limits the amount of VLDL to which ApoC-III can attach before secretion into the circulation or that ApoB inhibition directly reduces ApoC-III synthesis.

The new finding that antisense reduction of ApoB decreases ApoC-III concentration in total plasma, VLDL and suggestively in HDL is relevant to treatment because ApoC-III in VLDL has been associated with coronary heart disease (CHD). Additionally, studies have found that ApoC-III in HDL (or the cholesterol concentration of HDL that has apoC-III) is associated with risk of CHD. Also, ApoC-III has a direct pro-atherogenic, pro-inflammatory effect on monocytes and vascular endothelial cells. ApoC-III in HDL does not have a protective action against monocyte adhesion to vascular endothelial cells. Thus, the findings in the present study suggest an anti-atherogenic action of mipomersen, mediated through reduction in ApoC-III in ApoB lipoproteins and in HDL. Also, the ApoB concentration in LDL containing ApoC-III strongly predicts recurrent cardiovascular disease in type 2 diabetics. As shown in the example below, antisense reduction of ApoC-III results in reduced fat and plasma glucose along with a reduction in lipids.

In conclusion, lowering ApoC-III by antisense inhibition of ApoB renders such ApoB targeting compounds useful for diabetic and/or obese subjects or subjects suffering from diabetic dyslipidemia, mixed dyslipidemia or steatosis.

Example 5

Effects of Apolipoprotein C-III Antisense Inhibition

As provided in U.S. application Ser. No. 10/553,722, modified oligonucleotides were designed to target different regions of the mouse Apolipoprotein C-III RNA, using published sequences (GenBank accession number L04150.1, incorporated herein as SEQ ID NO: 11). Examples of modified oligonucleotides are shown in Table 16. "Target site" indicates the first (5'-most) nucleotide number on the particular target nucleic acid to which the compound binds. All compounds in the table are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

TABLE 16

Chimeric phosphorothioate oligonucleotides having 2'-MOE wings and a deoxy gap

| ISIS # | REGION | TARGET SITE | SEQUENCE | SEQ ID NO |
|---|---|---|---|---|
| 167875 | stop codon | 334 | TCACGACTCAATAGCTGGAG | 12 |
| 167878 | 3'UTR | 441 | AGACATGAGAACATACTTTC | 13 |
| 167879 | 3'UTR | 471 | CATGTTTAGGTGAGATCTAG | 14 |
| 167880 | 3'UTR | 496 | TCTTATCCAGCTTTATTAGG | 15 |

The effects of oligonucleotides targeting Apolipoprotein C-III were tested in vivo. Antisense oligonucleotides were administered to mice to determine the effect of antisence inhibition on various parameters.

Effects of Antisense Inhibition of Apolipoprotein C-III (ISIS 167880) on Serum Cholesterol and Triglyceride Levels C57BL/6 mice, a strain reported to be susceptible to hyperlipidemia-induced atherosclerotic plaque formation were used in the following studies to evaluate Apolipoprotein C-III antisense oligonucleotides as potential agents to lower cholesterol and triglyceride levels.

Male C57BL/6 mice (n=8) receiving a high fat diet (60% kcal fat) were evaluated over the course of 6 weeks for the effects of ISIS 167880 on serum cholesterol and triglyceride levels. Control animals received saline treatment. Mice were dosed intraperitoneally every three days (twice a week), after fasting overnight, with 50 mg/kg ISIS 167880 or saline for six weeks.

Male C57BL/6 mice fed a normal rodent diet were fasted overnight then dosed intraperitoneally every three days with saline (control), 50 mg/kg ISIS 167880 or 50 mg/kg ISIS 167879 for two weeks.

At study termination, forty eight hours after the final injections, the animals were sacrificed and evaluated for serum cholesterol and triglyceride levels and compared to the saline control. Measurements of serum cholesterol and triglyceride levels were obtained through routine clinical analysis.

High fat fed mice treated with ISIS 167880 showed a reduction in both serum cholesterol (196 mg/dL for control animals and 137 mg/dL for ISIS 167880) and triglycerides (151 mg/dL for control animals and 58 mg/dL for ISIS 167880) by study end.

No effect was seen on serum cholesterol levels for lean mice treated with ISIS 167880 (91 mg/dL for control animals and 91 mg/dL for ISIS 167880), however triglycerides were lowered (91 mg/dL for control animals and 59 mg/dL for ISIS 167880) by study end.

Lean mice treated with ISIS 167879 showed an increase in serum cholesterol (91 mg/dL for control animals and 116 mg/dL for ISIS 167879) but a reduction in triglycerides (91 mg/dL for control animals and 65 mg/dL for ISIS 167879) by study end.

These results indicate that, in mice fed a high fat diet, ISIS 167880 reduces cholesterol and triglyceride to levels that are comparable to lean littermates while having no deleterious effects on the lean animals (see Table 17 for summary of in vivo data).

Effects of Antisense Inhibition of Apolipoprotein C-III (ISIS 167880) on Serum AST and ALT Levels C57BL/6 mice were used in the following studies to evaluate the liver toxicity of Apolipoprotein C-III antisense oligonucleotides.

Male C57BL/6 mice (n=8) receiving a high fat diet (60% kcal fat) were evaluated over the course of 6 weeks for the effects of ISIS 167880 on liver enzyme (AST and ALT) levels. Control animals received saline treatment. Mice were dosed intraperitoneally every three days (twice a week), after fasting overnight, with 50 mg/kg ISIS 167880 or saline for six weeks.

Male C57BL/6 mice fed a normal rodent diet were fasted overnight then dosed intraperitoneally every three days with saline (control), 50 mg/kg ISIS 167880 or 50 mg/kg ISIS 167879 for two weeks.

At study termination and forty-eight hours after the final injections, animals were sacrificed and evaluated for serum AST and ALT levels, which were measured by routine clinical methods. Increased levels of the liver enzymes ALT and AST can indicate toxicity and liver damage.

High fat fed mice treated with ISIS 167880 showed an increase in AST levels over the duration of the study compared to saline controls (157 IU/L for ISIS 167880, compared to 92 IU/L for saline control).

ALT levels in high fat fed mice were increased by treatments with ISIS 167880 over the duration of the study compared to saline controls (64 IU/L for ISIS 167880, compared to 40 IU/L for saline control).

Lean mice treated with ISIS 167880 showed no significant increase in AST and ALT levels over the duration of the study compared to saline controls (AST levels of 51 IU/L for control compared to 58 IU/L for ISIS 167880; ALT levels of 26 IU/L for control compared to 27 IU/L for ISIS 167880).

Lean mice treated with ISIS 167879 showed no change in AST levels and a decrease in ALT levels over the duration of the study compared to saline controls (AST levels of 51 IU/L for control compared to 51 IU/L for ISIS 167879; ALT levels of 26 IU/L for control compared to 21 IU/L for ISIS 167879).

These results suggest a minor liver toxicity effect from ISIS 167880 in mice fed a high fat diet but no liver toxicity from ISIS 167880 or 167879 in mice fed a normal rodent diet (see Table 17 for summary of in vivo data).

Effects of Antisense Inhibition of Apolipoprotein C-III (ISIS 167880) on Serum Glucose Levels Male C57BL/6 mice (n=8) receiving a high fat diet (60% kcal fat) were evaluated over the course of 6 weeks for the effects of ISIS 167880 on serum glucose levels. Control animals received saline treatment. Mice were dosed intraperitoneally every three days (twice a week), after fasting overnight, with 50 mg/kg ISIS 167880 or saline for six weeks.

Male C57BL/6 mice fed a normal rodent diet were fasted overnight then dosed intraperitoneally every three days with saline (control), 50 mg/kg ISIS 167880 or 50 mg/kg ISIS 167879 for two weeks.

At study termination and forty-eight hours after the final injections, animals were sacrificed and evaluated for serum glucose levels, which was measured by routine clinical methods.

In the high fat fed mice, ISIS 167880 reduced serum glucose levels to 183 mg/dL, compared to the saline control of 213 mg/dL. In lean mice, ISIS 167880 had no significant effect on serum glucose levels with measurements of 203 mg/dL, compared to the saline control of 204 mg/dL; while ISIS 167879 only slightly increased serum glucose levels to 216 mg/dL.

These results indicate that, in mice fed a high fat diet, ISIS 167880 is able to reduce serum glucose to levels comparable to lean littermates, while having no deleterious effects on the lean animals (see Table 17 for summary of in vivo data).

Effects of Antisense Inhibition of Apolipoprotein C-III (ISIS 167880) on Apolipoprotein C-III mRNA Levels in C57BL/6 Mice Male C57BL/6 mice received a high fat diet (60% kcal fat) fasted overnight, and dosed intraperitoneally every three days with saline or 50 mg/kg ISIS 167880 for six weeks.

Male C57BL/6 mice fed a normal rodent diet were fasted overnight then dosed intraperitoneally every three days with saline (control) or 50 mg/kg ISIS 167880 or 50 mg/kg ISIS 167879 for two weeks.

At study termination, forty-eight hours after the final injections, animals were sacrificed and evaluated for Apolipoprotein C-III mRNA levels in liver. The high fat fed mice dosed with ISIS 167880 had Apolipoprotein C-III mRNA levels 8% that of the saline treated mice. The lean mice showed decreased Apolipoprotein C-III mRNA after treatment with either ISIS 167880 or ISIS 167879. The lean mice dosed with ISIS 167880 had Apolipoprotein C-III mRNA levels 21% that of the saline treated mice and those dosed with ISIS 167879 had Apolipoprotein C-III mRNA levels 27% that of the saline treated mice.

These results indicate that in both high fat fed mice and lean mice, antisense oligonucleotides directed against Apolipoprotein C-III are able to decrease Apolipoprotein C-III mRNA levels in vivo to a similar extent (see Table 17 for summary of in vivo data).

TABLE 17

Effects of ISIS 167880 or 167879 Treatment on Cholesterol, Triglyceride, Glucose, Liver Enzyme, and Apolipoprotein C-III mRNA in Liver, in Lean and High Fat Fed C57BL/6 Mice.

|  | Biological Marker Measured units | ISIS # | Diet, Experiment duration | |
|---|---|---|---|---|
|  |  |  | High Fat, 6 week | Lean, 2 week |
|  | Cholesterol | control | 196 | 91 |
|  | mg/dL | 167880 | 137 | 91 |
|  |  | 167879 | N.D. | 116 |
|  | Triglycerides | control | 151 | 91 |
|  | mg/dL | 167880 | 58 | 59 |
|  |  | 167879 | N.D. | 65 |
|  | Glucose | control | 213 | 204 |
|  | mg/dL | 167880 | 183 | 203 |
|  |  | 167879 | N.D. | 216 |
| Liver Enzymes | AST IU/L | control | 92 | 51 |
|  |  | 167880 | 157 | 58 |
|  |  | 167879 | N.D. | 51 |
|  | ALT IU/L | control | 40 | 26 |
|  |  | 167880 | 64 | 27 |
|  |  | 167879 | N.D. | 21 |
|  | Apolipoprotein C-III mRNA % of control | 167880 | 8% | 21% |
|  |  | 167879 | N.D. | 27% |

In summary, these results indicate that, in mice fed a high fat diet, ISIS 167880 is able to reduce serum glucose, cholesterol and triglyceride to levels comparable to lean littermates, while having no deleterious effects on the lean animals. Furthermore, antisense oligonucleotides directed against Apolipoprotein C-III are able to decrease Apolipoprotein C-III mRNA levels in vivo to a similar extent in both high fat fed mice and lean mice. These results suggest a minor liver toxicity effect from ISIS 167880 in mice fed a high fat diet but no liver toxicity from ISIS 167880 or 167879 in mice fed a normal rodent diet.

Effects of Antisense Inhibition of Apolipoprotein C-III mRNA In Vivo

C57BL/6 mice, a strain reported to be susceptible to hyperlipidemia-induced atherosclerotic plaque formation, were used in the following studies to evaluate Apolipoprotein C-III antisense oligonucleotides as potential agents to lower cholesterol and triglyceride levels. Accordingly, in a further embodiment, C57BL/6 mice on a high-fat diet were treated with antisense oligonucleotides targeted to Apolipoprotein C-III.

Male C57BL/6 mice (n=8; 7 to 8 weeks of age) receiving a high fat diet (60% kcal fat) were evaluated for Apolipoprotein C-III mRNA expression in liver after 6 weeks of treatment with antisense oligonucleotides targeted to Apolipoprotein C-III. Mice received twice weekly intraperitoneal injections at a dose of 25 mg/kg of ISIS 167880, ISIS 167875, ISIS 167878 or ISIS 167879. Control animals received saline treatment twice weekly for a period of 6 weeks.

At study termination, forty-eight hours after the final injections, the animals were sacrificed and evaluated for Apolipoprotein C-III mRNA expression in liver. RNA was isolated from liver and mRNA was quantitated as described herein. Apolipoprotein C-III mRNA levels from each treatment group (n=8) were averaged. Relative to saline-treated animals, treatment with ISIS 167875, ISIS 167878, ISIS 167879 and ISIS 167880 resulted in a 24%, 56%, 50% and 77% reduction in Apolipoprotein C-III mRNA levels, respectively, demonstrating that these compounds significantly reduced Apolipoprotein C-III mRNA expression in liver.

Effects of Antisense Inhibition of Apolipoprotein C-III on Serum Cholesterol, Triglyceride, Glucose and Serum Transaminases In a further embodiment, the mice treated with saline or a 25 mg/kg dose of ISIS 167880 ISIS 167875, ISIS 167878 or ISIS 167879 as described above were evaluated for serum cholesterol and triglyceride levels following 6 weeks of treatment.

At study termination, forty-eight hours after the dose of saline or antisense compound, the animals were sacrificed and evaluated for serum cholesterol, triglyceride and glucose levels by routine analysis using an Olympus Clinical Analyzer (Olympus America Inc., Melville, N.Y.). The serum transaminases ALT and AST, increases in which can indicate hepatotoxicity, were also measured using an Olympus Clinical Analyzer (Olympus America Inc., Melville, N.Y.). The levels of serum cholesterol, triglycerides and glucose are presented in Table 18 as the average result from each treatment group (n=8), in mg/dL. ALT and AST, also shown in the table, are also shown as the average result from each treatment group (n=8), in international units/L (IU/L).

TABLE 18

Effects of antisense inhibition of apolipoprotein C-III on serum cholesterol, triglyceride, glucose and transaminases

| Serum marker | Treatment | | | | |
|---|---|---|---|---|---|
| | Saline | ISIS 167875 | ISIS 167878 | ISIS 167879 | ISIS 167880 |
| Total Cholesterol mg/dL | 172 | 197 | 180 | 132 | 155 |
| HDL Cholesterol mg/dL | 149 | 162 | 157 | 117 | 137 |
| LDL Cholesterol mg/dL | 25 | 37 | 28 | 24 | 21 |
| Serum Triglyerides mg/dL | 126 | 99 | 75 | 60 | 52 |
| ALT IU/L | 24 | 555 | 32 | 45 | 66 |
| AST IU/L | 56 | 489 | 76 | 117 | 132 |
| Glucose mg/dL | 273 | 234 | 251 | 189 | 255 |

A significant reduction in serum triglyceride levels was observed following treatment with ISIS 167875, ISIS 167878, ISIS 167879 and ISIS 167880, which reduced triglyceride levels 22%, 40%, 52% and 58%, respectively. This reduction in serum triglycerides correlated with the reduction in Apolipoprotein C-III liver mRNA expression. Moreover, reductions in target and serum triglycerides following treatment with ISIS 167878, ISIS 167879 and ISIS 167880 were not accompanied by hepatotoxicity, as indicated by the lack of significant increases in ALT and AST levels. Glucose levels were significantly lowered following treatment with ISIS 167879.

Effects of Antisense Inhibition of Apolipoprotein C-III on Body Weight and Organ Weight In a further embodiment, the animals treated with saline or a 25 mg/kg dose of ISIS 167880, ISIS 167875, ISIS 167878 or ISIS 167879 as described above were evaluated for changes in body weight, fat pad, liver and spleen weights. At study termination, forty-eight hours following the final dose of saline or antisense compound, the animals were sacrificed and body and organ weights were measured. The data shown in Table 19 represent average weights from all animals in each treatment group (n=8). Body weight is presented in grams (g), while spleen, liver and fat pad weights are presented in milligrams (mg).

TABLE 19

Effects of Antisense Inhibition of Apolipoprotein C-III on Body and Organ Weights

| | Treatment | | | | |
|---|---|---|---|---|---|
| | Saline | ISIS 167875 | ISIS 167878 | ISIS 167879 | ISIS 167880 |
| Body weight (g) | 33 | 30 | 32 | 28 | 30 |
| Liver weight (mg) | 126 | 190 | 141 | 133 | 146 |
| Fat pad weight (mg) | 182 | 125 | 125 | 61 | 62 |
| Spleen weight (mg) | 8 | 12 | 12 | 12 | 14 |

As is evident in Table 19, treatment with antisense compounds targeted to mouse Apolipoprotein C-III resulted in significant reductions in fat pad weight. ISIS 167875 and ISIS 167878 both led to a 31% reduction in fat pad weight, while ISIS 167879 and ISIS 167880 both resulted in a 66% lowering of fat pad weight. Body weights were not significantly changed and spleen weights were slightly increased following antisense compound treatment. With the exception livers from animals treated with ISIS 167875, liver weights were not significantly changed.

Effects of Antisense Inhibition of Apolipoprotein C-III on Liver Triglyceride Levels Hepatic steatosis refers to the accumulation of lipids in the liver, or "fatty liver", which is frequently caused by alcohol consumption, diabetes and hyperlipidemia and can progress to end-stage liver damage. Given the deleterious consequences of a fatty liver condition, it is of use to identify compounds that prevent or ameliorate hepatic steatosis. Hepatic steatosis is evaluated both by measurement of tissue triglyceride content and by histologic examination of liver tissue.

Liver tissue triglyceride content was assessed in the animals treated with saline or a 25 mg/kg dose of ISIS 167880, ISIS 167875, ISIS 167878 or ISIS 167879 as described above. Liver tissue triglyceride content was measured using the Triglyceride GPO assay (Roche Diagnostics, Indianapolis, Ind.). Histological analysis was conducted by routine procedures, whereby liver tissue was fixed in neutral-buffered formalin, embedded in paraffin, sectioned and subsequently stained with hematoxylin and eosin, to visualize nuclei and cytoplasm, respectively. Alternatively, liver tissue was procured then immediately frozen, sectioned, and subsequently stained with oil red O stain to visualize lipid deposits and counterstained with eosin to mark cytoplasm. The prepared samples were evaluated by light microscopy.

Relative to saline treated mice, liver tissue triglyceride levels were significantly lowered, by 25%, 35%, 40% and 64% following treatment with ISIS 167875, ISIS 167878, ISIS 167879 and ISIS 167880, respectively. Histological analysis of stained liver sections similarly revealed a reduction in liver tissue triglycerides. Thus, as demonstrated by measurement of tissue triglycerides and histological analyses of liver tissue sections, treatment with antisense compounds targeted to Apolipoprotein C-III reduced liver triglyceride content. As such, antisense compounds targeted to Apolipoprotein C-III are candidate therapeutic agents for the prevention or amelioration of hepatic steatosis.

What is claimed is:

1. A method of lowering plasma apolipoprotein C-III levels in a human subject, comprising:
    selecting a human subject with elevated apolipoprotein C-III levels or a condition associated with apolipoprotein C-III; and
    administering to said human subject a therapeutically effective amount of a compound comprising a modified oligonucleotide having 12-30 linked nucleosides, or a salt thereof,
    wherein said modified oligonucleotide is 100% complementary to a nucleic acid encoding human apolipoprotein B, and whereby plasma apolipoprotein C-III levels in said human subject are lowered.

2. A method for treating, reducing the incidence of, or ameliorating a symptom of diabetes in a human subject, comprising administering to said human subject a therapeutically effective amount of a compound comprising a modified oligonucleotide having 12-30 linked nucleosides, or a salt thereof, wherein said modified oligonucleotide is 100% complementary to a nucleic acid encoding human apolipoprotein B, and wherein plasma apolipoprotein C-III levels in said human subject are lowered, whereby the diabetes is treated, the incidence reduced or the symptom ameliorated.

3. The method of claim 2, wherein said subject is selected based on a determination of elevated plasma apolipoprotein C-III concentrations, elevated plasma total cholesterol concentrations, elevated plasma LDL cholesterol, elevated plasma triglyceride concentrations, reduced plasma HDL cholesterol concentrations, elevated liver triglyceride concentrations, elevated apolipoprotein C-III concentrations in HDL cholesterol particles, elevated apolipoprotein C-III concentrations in VLDL cholesterol particles or elevated apolipoprotein C-III concentrations in cholesterol particles comprising apolipoprotein B.

4. The method of claim 3, wherein said subject has or is at risk of having diabetic dyslipidemia or mixed dyslipidemia.

5. A method for treating, reducing the incidence of, or ameliorating a symptom of coronary heart disease in a human subject, comprising administering to said human subject a therapeutically effective amount of a compound comprising a modified oligonucleotide having 12-30 linked nucleosides, or a salt thereof, wherein said modified oligonucleotide is 100% complementary to a nucleic acid encoding human apolipoprotein B, and wherein plasma apolipoprotein C-III levels in said human subject are lowered, whereby the coronary heart disease is treated, the incidence reduced or the symptom ameliorated.

6. The method of claim 5, wherein said subject is selected based on a determination of elevated plasma apolipoprotein C-III concentrations, elevated plasma total cholesterol concentrations, elevated plasma LDL cholesterol, elevated plasma triglyceride concentrations, reduced plasma HDL cholesterol concentrations, elevated liver triglyceride concentrations, elevated apolipoprotein C-III concentrations in HDL cholesterol particles, elevated apolipoprotein C-III concentrations in VLDL cholesterol particles or elevated apolipoprotein C-III concentrations in cholesterol particles comprising apolipoprotein B.

7. The method of claim 6, wherein said subject has or is at risk of having diabetic dislipidemia or mixed dyslipidemia.

8. The method of claim 3, wherein the human subject is obese.

9. The method of claim 6, wherein the human subject is obese.

10. The method of claim 6, wherein the human subject is diabetic.

11. The method of claim 1, wherein selection of the subject is based on a determination of elevated apolipoprotein C-III levels or a condition associated with apolipoprotein C-III.

12. The method of claim 11, wherein the selected subject is determined to have elevated plasma total cholesterol concentrations, elevated plasma LDL cholesterol, elevated plasma triglyceride concentrations, reduced plasma HDL cholesterol concentrations, elevated liver triglyceride concentrations, elevated apolipoprotein C-III concentrations in HDL cholesterol particles, elevated apolipoprotein C-III concentrations in VLDL cholesterol particles or elevated apolipoprotein C-III concentrations in cholesterol particles comprising apolipoprotein B.

13. The method of claim 11, wherein the modified oligonucleotide has a nucleobase sequence comprising at least an 8 nucleobase portion or at least a 12 nucleobase portion of SEQ ID NO:10.

14. The method of claim 11, wherein the modified oligonucleotide has a nucleobase sequence comprising SEQ ID NO:10.

15. The method of claim 11, wherein the modified oligonucleotide has a nucleobase sequence consisting of SEQ ID NO:10.

16. The method of claim 11, wherein the modified oligonucleotide comprises at least one modified internucleoside linkage, at least one modified sugar moiety, and/or at least one modified nucleobase.

17. The method of claim 16, wherein the modified internucleoside linkage is a phosphorothioate internucleoside linkage.

18. The method of claim 16, wherein the modified sugar moiety is a bicyclic sugar moiety or a 2'-substituted sugar moiety.

19. The method of claim 18, wherein the bicyclic sugar moiety comprises a 4'-CH$_2$—O-2' bridge.

20. The method of claim 18, wherein the 2'-substituted sugar moiety comprises a 2'-O-methoxyethyl.

21. The method of claim 16, wherein the modified nucleobase is a 5-methylcytosine.

22. The method of claim 11, wherein the modified oligonucleotide comprises:
a gap segment consisting of linked deoxynucleosides;
a 5' wing segment consisting of linked nucleosides; and
a 3' wing segment consisting of linked nucleosides;
wherein the gap segment is positioned between the 5' wing segment and the 3' wing segment and wherein each nucleoside of each wing segment comprises a modified sugar moiety, wherein the modified oligonucleotide comprises at least one modified nucleobase, and wherein at least one internucleoside linkage is a phosphorothioate linkage.

23. The method of claim 22, wherein each modified sugar moiety is a 2'-O-methoxyethyl sugar moiety or a bicyclic sugar moiety.

24. The method of claim 22, wherein the modified nucleobase is a 5-methylcytosine.

25. The method of claim 22, wherein the modified oligonucleotide comprises:
a gap segment consisting of ten deoxynucleosides;
a 5' wing segment consisting of five linked nucleosides; and
a 3' wing segment consisting of five linked nucleosides;
wherein the gap segment is positioned between the 5' wing segment and the 3' wing segment, wherein each nucleoside of each wing segment comprises a 2'-O-methoxyethyl sugar moiety, wherein each cytosine is a 5'-methylcytosine, and wherein each internucleoside linkage is a phosphorothioate internucleoside linkage.

26. The method of claim 11, wherein the compound comprises a salt of the modified oligonucleotide.

27. The method of claim 11, wherein the compound is formulated as a composition comprising a pharmaceutically acceptable excipient, vehicle, carrier or diluent.

28. The method of claim 11, wherein the therapeutically effective amount is delivered in a plurality of doses of the compound.

29. The method of claim 28, wherein the plurality of doses results in a plasma trough concentration of the compound from about 12 ng/mL to about 40 ng/mL in the plasma of the human subject or a plasma trough AUC of the compound from about 12 µg·hr/mL to about 60 µg·hr/mL in the plasma of the human subject.

30. The method of claim 29, wherein the compound is mipomersen.

31. The method of claim 30, wherein each of the plurality of doses is 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, at least about 100 mg, at least about 200 mg, about 200 mg to about 400 mg, about 100 mg, about 200 mg, about 300 mg, or about 400 mg of mipomersen.

32. The method of claim 28, wherein at least one dose of said plurality of doses is administered daily, about twice a week, about once a week, about once every other week or about once a month.

33. The method of claim 11, wherein the plasma apolipoprotein C-III levels are reduced at least about 10%, at least about 20%, at least about 30%, at least about 40%, at least about 50%, at least about 54%, at least about 60% or at least about 62% relative to the amount of plasma apolipoprotein C-III observed in the subject prior to administration of the compound.

34. The method of claim 1, wherein the selected subject is determined to have elevated plasma total cholesterol concentrations, elevated plasma LDL cholesterol, elevated plasma triglyceride concentrations, reduced plasma HDL cholesterol concentrations, elevated liver triglyceride concentrations, elevated apolipoprotein C-III concentrations in HDL cholesterol particles, elevated apolipoprotein C-III concentrations in VLDL cholesterol particles or elevated apolipoprotein C-III concentrations in cholesterol particles comprising apolipoprotein B.

* * * * *

SEQUENCE LISTING

<160> NUMBER OF SEQ ID NOS: 15

<210> SEQ ID NO 1
<211> LENGTH: 14121
<212> TYPE: DNA
<213> ORGANISM: H. sapiens

<400> SEQUENCE: 1

| | | | | | |
|---|---|---|---|---|---|
| attcccaccg | ggacctgcgg | ggctgagtgc | ccttctcggt | tgctgccgct | gaggagcccg | 60 |
| cccagccagc | cagggccgcg | aggccgaggc | caggccgcag | cccaggagcc | gccccaccgc | 120 |
| agctggcgat | ggacccgccg | aggcccgcgc | tgctggcgct | gctggcgctg | cctgcgctgc | 180 |
| tgctgctgct | gctggcgggc | gccagggccg | aagaggaaat | gctggaaaat | gtcagcctgg | 240 |
| tctgtccaaa | agatgcgacc | cgattcaagc | acctccggaa | gtacacatac | aactatgagg | 300 |
| ctgagagttc | cagtgagtcc | cctgggactg | ctgattcaag | aagtgccacc | aggatcaact | 360 |
| gcaaggttga | gctggaggtt | ccccagctct | gcagcttcat | cctgaagacc | agccagtgca | 420 |
| ccctgaaaga | ggtgtatggc | ttcaaccctg | agggcaaagc | cttgctgaag | aaaaccaaga | 480 |
| actctgagga | gtttgctgca | gccatgtcca | ggtatgagct | caagctggcc | attccagaag | 540 |
| ggaagcaggt | tttcctttac | ccggagaaag | atgaacctac | ttacatcctg | aacatcaaga | 600 |
| ggggcatcat | ttctgccctc | ctggttcccc | cagagacaga | agaagccaag | caagtgttgt | 660 |
| ttctggatac | cgtgtatgga | aactgctcca | ctcactttac | cgtcaagacg | aggaagggca | 720 |
| atgtggcaac | agaaatatcc | actgaaagag | acctggggca | gtgtgatcgc | ttcaagccca | 780 |
| tccgcacagg | catcagccca | cttgctctca | tcaaaggcat | gacccgcccc | ttgtcaactc | 840 |
| tgatcagcag | cagccagtcc | tgtcagtaca | cactggacgc | taagaggaag | catgtggcag | 900 |
| aagccatctg | caaggagcaa | cacctcttcc | tgccttttct | ctacaacaat | aagtatggga | 960 |
| tggtagcaca | agtgacacag | actttgaaac | ttgaagacac | accaaagatc | aacagccgct | 1020 |
| tctttggtga | aggtactaag | aagatgggcc | tcgcatttga | gagcaccaaa | tccacatcac | 1080 |
| ctccaaagca | ggccgaagct | gttttgaaga | ctctccagga | actgaaaaaa | ctaaccatct | 1140 |
| ctgagcaaaa | tatccagaga | gctaatctct | tcaataagct | ggttactgag | ctgagaggcc | 1200 |
| tcagtgatga | agcagtcaca | tctctcttgc | cacagctgat | tgaggtgtcc | agccccatca | 1260 |
| cttttacaagc | cttggttcag | tgtggacagc | ctcagtgctc | cactcacatc | ctccagtggc | 1320 |
| tgaaacgtgt | gcatgccaac | cccctttctga | tagatgtggt | cacctacctg | gtggccctga | 1380 |
| tccccgagcc | ctcagcacag | cagctgcgag | agatcttcaa | catggcgagg | gatcagcgca | 1440 |
| gccgagccac | cttgtatgcg | ctgagccacg | cggtcaacaa | ctatcataag | acaaacccta | 1500 |
| cagggaccca | ggagctgctg | acattgctaa | attacctgat | ggaacagatt | caagatgact | 1560 |
| gcactgggga | tgaagattac | acctatttga | ttctgcgggt | cattggaaat | atgggccaaa | 1620 |
| ccatggagca | gttaactcca | gaactcaagt | cttcaatcct | caaatgtgtc | caaagtacaa | 1680 |
| agccatcact | gatgatccag | aaagctgcca | tccaggctct | gcggaaaatg | gagcctaaag | 1740 |
| acaaggacca | ggaggttctt | cttcagactt | tccttgatga | tgcttctccg | ggagataagc | 1800 |
| gactggctgc | ctatcttatg | ttgatgagga | gtccttcaca | ggcagatatt | aacaaaattg | 1860 |
| tccaaattct | accatgggaa | cagaatgagc | aagtgaagaa | ctttgtggct | tcccatattg | 1920 |
| ccaatatctt | gaactcagaa | gaattggata | tccaagatct | gaaaagtta | gtgaaagaag | 1980 |
| ctctgaaaga | atctcaactt | ccaactgtca | tggacttcag | aaaattctct | cggaactatc | 2040 |
| aactctacaa | atctgtttct | cttccatcac | ttgacccagc | ctcagccaaa | atagaaggga | 2100 |

```
atcttatatt tgatccaaat aactaccttc ctaaagaaag catgctgaaa actaccctca     2160
ctgcctttgg atttgcttca gctgacctca tcgagattgg cttggaagga aaaggctttg     2220
agccaacatt ggaagctctt tttgggaagc aaggattttt cccagacagt gtcaacaaag     2280
ctttgtactg ggttaatggt caagttcctg atggtgtctc taaggtctta gtggaccact     2340
ttggctatac caaagatgat aaacatgagc aggatatggt aaatggaata atgctcagtg     2400
ttgagaagct gattaaagat ttgaaatcca agaagtccc ggaagccaga gcctacctcc      2460
gcatcttggg agaggagctt ggttttgcca gtctccatga cctccagctc ctgggaaagc     2520
tgcttctgat gggtgcccgc actctgcagg ggatccccca tgattggag gaggtcatca      2580 ggaagggctc aaagaatgac ttttttcttc actacatctt catggagaat gcctttgaac     2640
tccccactgg agctggatta cagttgcaaa tatcttcatc tggagtcatt gctcccggag     2700
ccaaggctgg agtaaaactg gaagtagcca acatgcaggc tgaactggtg caaaaccct      2760 ccgtgtctgt ggagtttgtg acaaatatgg gcatcatcat tccggacttc gctaggagtg     2820
gggtccagat gaacaccaac ttcttccacg agtcgggtct ggaggctcat gttgccctaa     2880
aagctgggaa gctgaagttt atcattcctt ccccaaagag accagtcaag ctgctcagtg     2940
gaggcaacac attacatttg gtctctacca ccaaaacgga ggtgatccca cctctcattg     3000
agaacaggca gtcctggtca gtttgcaagc aagtctttcc tggcctgaat tactgcacct     3060
caggcgctta ctccaacgcc agctccacag actccgcctc ctactatccg ctgaccgggg     3120
acaccagatt agagctggaa ctgaggccta caggagagat tgagcagtat tctgtcagcg     3180
caacctatga gctccagaga gaggacagag ccttggtgga taccctgaag tttgtaactc     3240
aagcagaagg tgcgaagcag actgaggcta ccatgacatt caaatataat cggcagagta     3300
tgaccttgtc cagtgaagtc caaattccgg attttgatgt tgacctcgga acaatcctca     3360
gagttaatga tgaatctact gagggcaaaa cgtcttacag actcacctg gacattcaga      3420 acaagaaaat tactgaggtc gccctcatgg gccacctaag ttgtgacaca aaggaagaaa     3480
gaaaaatcaa gggtgttatt tccatacccc gtttgcaagc agaagccaga agtgagatcc     3540
tcgcccactg gtcgcctgcc aaactgcttc tccaaatgga ctcatctgct acagcttatg     3600
gctccacagt ttccaagagg gtggcatggc attatgatga agagaagatt gaatttgaat     3660
ggaacacagg caccaatgta gataccaaaa aaatgacttc caatttccct gtggatctct     3720
ccgattatcc taagagcttg catatgtatg ctaatagact cctggatcac agagtccctg     3780
aaacagacat gactttccgg cacgtgggtt ccaaattaat agttgcaatg agctcatggc     3840
ttcagaaggc atctgggagt cttccttata cccagacttt gcaagaccac ctcaatagcc     3900
tgaaggagtt caacctccag aacatgggat tgccagactt ccacatccca gaaacctct       3960 tcttaaaaag cgatggccgg gtcaaatata ccttgaacaa gaacagtttg aaaattgaga     4020
ttcctttgcc ttttggtggc aaatcctcca gagatctaaa gatgttagag actgttagga     4080
caccagccct ccacttcaag tctgtgggat tccatctgcc atctcgagag ttccaagtcc     4140 ctactttac cattcccaag ttgtatcaac tgcaagtgcc tctcctgggt gttctagacc      4200
tctccacgaa tgtctacagc aacttgtaca actggtccgc ctcctacagt ggtggcaaca     4260
ccagcacaga ccatttcagc cttcgggctc gttaccacat gaaggctgac tctgtggttg     4320
acctgctttc ctacaatgtg caaggatctg gagaaacaac atatgaccac aagaatacgt     4380
tcacactatc atgtgatggg tctctacgcc acaaatttct agattcgaat atcaaattca     4440
```

```
gtcatgtaga aaaacttgga aacaacccag tctcaaaagg tttactaata ttcgatgcat    4500
ctagttcctg gggaccacag atgtctgctt cagttcattt ggactccaaa agaaacagc    4560
atttgtttgt caaagaagtc aagattgatg ggcagttcag agtctcttcg ttctatgcta    4620
aaggcacata tggcctgtct tgtcagaggg atcctaacac tggccggctc aatggagagt    4680
ccaacctgag gtttaactcc tcctacctcc aaggcaccaa ccagataaca ggaagatatg    4740
aagatggaac cctctccctc acctccacct ctgatctgca aagtggcatc attaaaaata    4800
ctgcttccct aaagtatgag aactacgagc tgactttaaa atctgacacc aatgggaagt    4860
ataagaactt tgccacttct aacaagatgg atatgacctt ctctaagcaa aatgcactgc    4920
tgcgttctga atatcaggct gattacgagt cattgaggtt cttcagcctg ctttctggat    4980
cactaaattc ccatggtctt gagttaaatg ctgacatctt aggcactgac aaaattaata    5040
gtggtgctca caaggcgaca ctaaggattg gccaagatgg aatatctacc agtgcaacga    5100
ccaacttgaa gtgtagtctc ctggtgctgg agaatgagct gaatgcagag cttggcctct    5160
ctggggcatc tatgaaatta acaacaaatg gccgcttcag ggaacacaat gcaaaattca    5220
gtctggatgg gaaagccgcc ctcacagagc tatcactggg aagtgcttat caggccatga    5280
ttctgggtgt cgacagcaaa acatttttca acttcaaggt cagtcaagaa ggacttaagc    5340
tctcaaatga catgatgggc tcatatgctg aaatgaaatt tgaccacaca aacagtctga    5400
acattgcagg cttatcactg gacttctctt caaaacttga caacatttac agctctgaca    5460
agttttataa gcaaactgtt aatttacagc tacagcccta ttctctggta actactttaa    5520
acagtgacct gaaatacaat gctctggatc tcaccaacaa tgggaaacta cggctagaac    5580
ccctgaagct gcatgtggct ggtaacctaa aaggagccta ccaaaataat gaaataaaac    5640
acatctatgc catctcttct gctgccttat cagcaagcta taaagcagac actgttgcta    5700
aggttcaggg tgtggagttt agccatcggc tcaacacaga catcgctggg ctggcttcag    5760
ccattgacat gagcacaaac tataattcag actcactgca tttcagcaat gtcttccgtt    5820
ctgtaatggc cccgtttacc atgaccatcg atgcacatac aaatggcaat gggaaactcg    5880
ctctctgggg agaacatact gggcagctgt atagcaaatt cctgttgaaa gcagaacctc    5940
tggcatttac tttctctcat gattacaaag ctccacaag tcatcatctc gtgtctagga    6000
aaagcatcag tgcagctctt gaacacaaag tcagtgccct gcttactcca gctgagcaga    6060
caggcacctg gaaactcaag acccaattta caacaatga atacagccag gacttggatg    6120
cttacaacac taaagataaa attggcgtgg agcttactgg acgaactctg ctgacctaa    6180
ctctactaga ctccccaatt aaagtgccac ttttactcag tgagcccatc aatatcattg    6240
atgctttaga gatgagagat gccgttgaga agccccaaga atttacaatt gttgcttttg    6300
taaagtatga taaaaaccaa gatgttcact ccattaacct cccatttttt gagaccttgc    6360
aagaatattt tgagaggaat cgacaaacca ttatagttgt agtggaaaac gtacagagaa    6420
acctgaagca catcaatatt gatcaatttg taagaaaata cagagcagcc ctgggaaaac    6480
tcccacagca agctaatgat tatctgaatt cattcaattg ggagagacaa gtttcacatg    6540
ccaaggagaa actgactgct ctcacaaaaa agtatagaat tacagaaaat gatatacaaa    6600
ttgcattaga tgatgccaaa atcaacttta tgaaaaact atctcaactg cagacatata    6660
tgatacaatt tgatcagtat attaaagata gttatgattt acatgatttg aaaatagcta    6720
ttgctaatat tattgatgaa atcattgaaa attaaaaag tcttgatgag cactatcata    6780
tccgtgtaaa tttagtaaaa acaatccatg atctacattt gtttattgaa aatattgatt    6840
```

```
ttaacaaaag tggaagtagt actgcatcct ggattcaaaa tgtggatact aagtaccaaa    6900
tcagaatcca gatacaagaa aaactgcagc agcttaagag acacatacag aatatagaca    6960
tccagcacct agctggaaag ttaaaacaac acattgaggc tattgatgtt agagtgcttt    7020
tagatcaatt gggaactaca atttcatttg aaagaataaa tgatgttctt gagcatgtca    7080
aacactttgt tataaatctt attggggatt ttgaagtagc tgagaaaatc aatgccttca    7140
gagccaaagt ccatgagtta atcgagaggt atgaagtaga ccaacaaatc caggttttaa    7200
tggataaatt agtagagttg acccaccaat acaagttgaa ggagactatt cagaagctaa    7260
gcaatgtcct acaacaagtt aagataaaag attactttga gaaattggtt ggatttattg    7320
atgatgctgt gaagaagctt aatgaattat cttttaaaac attcattgaa gatgttaaca    7380
aattccttga catgttgata aagaaattaa agtcatttga ttaccaccag tttgtagatg    7440
aaaccaatga caaaatccgt gaggtgactc agagactcaa tggtgaaatt caggctctgg    7500
aactaccaca aaaagctgaa gcattaaaac tgttttttaga ggaaaccaag gccacagttg    7560
cagtgtatct ggaaagccta caggacacca aaataacctt aatcatcaat tggttacagg    7620
aggctttaag ttcagcatct ttggctcaca tgaaggccaa attccgagag actctagaag    7680
atacacgaga ccgaatgtat caaatggaca ttcagcagga acttcaacga tacctgtctc    7740
tggtaggcca ggtttatagc acacttgtca cctacatttc tgattggtgg actcttgctg    7800
ctaagaacct tactgacttt gcagagcaat attctatcca agattgggct aaacgtatga    7860
aagcattggt agagcaaggg ttcactgttc ctgaaatcaa gaccatcctt gggaccatgc    7920
ctgcctttga agtcagtctt caggctcttc agaaagctac cttccagaca cctgatttta    7980
tagtccccct aacagatttg aggattccat cagttcagat aaacttcaaa gacttaaaaa    8040
atataaaaat cccatccagg ttttccacac cagaatttac catccttaac accttccaca    8100
ttccttcctt tacaattgac tttgtcgaaa tgaaagtaaa gatcatcaga accattgacc    8160
agatgcagaa cagtgagctg cagtggcccg ttccagatat atatctcagg gatctgaagg    8220
tggaggacat tcctctagcg agaatcaccc tgccagactt ccgtttacca gaaatcgcaa    8280
ttccagaatt cataatccca actctcaacc ttaatgattt tcaagttcct gaccttcaca    8340
taccagaatt ccagcttccc cacatctcac acacaattga agtacctact tttggcaagc    8400
tatacagtat tctgaaaatc caatctcctc ttttcacatt agatgcaaat gctgacatag    8460
ggaatggaac cacctcagca aacgaagcag gtatcgcagc ttccatcact gccaaggag    8520 agtccaaatt agaagttctc aattttgatt ttcaagcaaa tgcacaactc tcaaacccta    8580
agattaatcc gctggctctg aaggagtcag tgaagttctc cagcaagtac ctgagaacgg    8640
agcatgggag tgaaatgctg ttttttggaa atgctattga gggaaaatca acacagtgg    8700 caagtttaca cacagaaaaa aatacactgg agcttagtaa tggagtgatt gtcaagataa    8760
acaatcagct taccctggat agcaacacta aatacttcca caattgaac atccccaaac    8820 tggacttctc tagtcaggct gacctgcgca acgagatcaa gacactgttg aaagctggcc    8880
acatagcatg gacttcttct ggaaaagggt catggaaatg ggcctgcccc agattctcag    8940
atgagggaac acatgaatca caaattagtt tcaccataga aggaccctc acttcctttg    9000 gactgtccaa taagatcaat agcaaacacc taagagtaaa ccaaaacttg gtttatgaat    9060
ctggctccct caacttttct aaacttgaaa ttcaatcaca agtcgattcc cagcatgtgg    9120
gccacagtgt tctaactgct aaaggcatgg cactgtttgg agaagggaag gcagagttta    9180
```

-continued

```
ctgggaggca tgatgctcat ttaaatggaa aggttattgg aactttgaaa aattctcttt   9240
tcttttcagc ccagccattt gagatcacgg catccacaaa caatgaaggg aatttgaaag   9300
ttcgttttcc attaaggtta acagggaaga tagacttcct gaataactat gcactgtttc   9360
tgagtcccag tgcccagcaa gcaagttggc aagtaagtgc taggttcaat cagtataagt   9420
acaaccaaaa tttctctgct ggaaacaacg agaacattat ggaggcccat gtaggaataa   9480
atggagaagc aaatctggat ttcttaaaca ttcctttaac aattcctgaa atgcgtctac   9540
cttacacaat aatcacaact cctccactga agatttctc tctatgggaa aaaacaggct    9600
tgaaggaatt cttgaaaacg acaaagcaat catttgattt aagtgtaaaa gctcagtata   9660
agaaaaacaa acacaggcat tccatcacaa atcctttggc tgtgctttgt gagtttatca   9720
gtcagagcat caaatccttt gacaggcatt ttgaaaaaaa cagaaacaat gcattagatt   9780
ttgtcaccaa atcctataat gaaacaaaaa ttaagtttga taagtacaaa gctgaaaaat   9840
ctcacgacga gctccccagg acctttcaaa ttcctggata cactgttcca gttgtcaatg   9900
ttgaagtgtc tccattcacc atagagatgt cggcattcgg ctatgtgttc ccaaaagcag   9960
tcagcatgcc tagtttctcc atcctaggtt ctgacgtccg tgtgccttca tacacattaa   10020
tcctgccatc attagagctg ccagtccttc atgtccctag aaatctcaag ctttctcttc   10080
cacatttcaa ggaattgtgt accataagcc atattttat tcctgccatg gcaatatta    10140 cctatgattt ctcctttaaa tcaagtgtca tcacactgaa taccaatgct gaacttttta   10200
accagtcaga tattgttgct catctccttt cttcatcttc atctgtcatt gatgcactgc   10260
agtacaaatt agagggcacc acaagattga caagaaaaag gggattgaag ttagccacag   10320
ctctgtctct gagcaacaaa tttgtggagg gtagtcataa cagtactgtg agcttaacca   10380
cgaaaaatat ggaagtgtca gtggcaaaaa ccacaaaagc cgaaattcca attttgagaa   10440
tgaatttcaa gcaagaactt aatggaaata ccaagtcaaa acctactgtc tcttcctcca   10500
tggaatttaa gtatgatttc aattcttcaa tgctgtactc taccgctaaa ggagcagttg   10560
accacaagct tagcttggaa agcctcacct cttactttc cattgagtca tctaccaaag    10620
gagatgtcaa gggttcggtt ctttctcggg aatattcagg aactattgct agtgaggcca   10680
acacttactt gaattccaag agcacacggt cttcagtgaa gctgcagggc acttccaaaa   10740
ttgatgatat ctggaacctt gaagtaaaag aaaattttgc tggagaagcc acactccaac   10800
gcatatattc cctctgggag cacagtacga aaaaccactt acagctagag ggcctctttt   10860
tcaccaacgg agaacataca agcaaagcca ccctggaact ctctccatgg caaatgtcag   10920
ctcttgttca ggtccatgca agtcagccca gttccttcca tgatttccct gaccttggcc   10980
aggaagtggc cctgaatgct aacactaaga accagaagat cagatggaaa aatgaagtcc   11040
ggattcattc tgggtctttc cagagccagg tcgagctttc caatgaccaa gaaaaggcac   11100
accttgacat tgcaggatcc ttagaaggac acctaaggtt cctcaaaaat atcatcctac   11160
cagtctatga caagagctta tgggatttcc taaagctgga tgtaaccacc agcattggta   11220
ggagacagca tcttcgtgtt tcaactgcct ttgtgtacac caaaaacccc aatggctatt   11280
cattctccat ccctgtaaaa gttttggctg ataaattcat tactcctggg ctgaaactaa   11340
atgatctaaa ttcagttctt gtcatgccta cgttccatgt cccatttaca gatcttcagg   11400
ttccatcgtg caaacttgac ttcagagaaa tacaaatcta taagaagctg agaacttcat   11460
catttgccct caacctacca acactccccg aggtaaaatt ccctgaagtt gatgtgttaa   11520
caaaatattc tcaaccagaa gactccttga ttccctttt tgagataacc gtgcctgaat   11580
```

```
ctcagttaac tgtgtcccag ttcacgcttc caaaaagtgt ttcagatggc attgctgctt    11640
tggatctaaa tgcagtagcc aacaagatcg cagactttga gttgcccacc atcatcgtgc    11700
ctgagcagac cattgagatt ccctccatta agttctctgt acctgctgga attgtcattc    11760
cttcctttca agcactgact gcacgctttg aggtagactc tcccgtgtat aatgccactt    11820
ggagtgccag tttgaaaaac aaagcagatt atgttgaaac agtcctggat tccacatgca    11880
gctcaaccgt acagttccta gaatatgaac taaatgtttt gggaacacac aaaatcgaag    11940
atggtacgtt agcctctaag actaaaggaa cacttgcaca ccgtgacttc agtgcagaat    12000
atgaagaaga tggcaaattt gaaggacttc aggaatggga aggaaaagcg caccttcaata   12060 tcaaaagccc agcgttcacc gatctccatc tgcgctacca gaaagacaag aaaggcatct    12120
ccacctcagc agcctcccca gccgtaggca ccgtgggcat ggatatggat gaagatgacg    12180
acttttctaa atggaacttc tactacagcc ctcagtcctc tccagataaa aaactcacca    12240
tattcaaaac tgagttgagg gtccgggaat ctgatgagga aactcagatc aaagttaatt    12300
gggaagaaga ggcagcttct ggcttgctaa cctctctgaa agacaacgtg cccaaggcca    12360
caggggtcct ttatgattat gtcaacaagt accactggga acacacaggg ctcaccctga    12420
gagaagtgtc ttcaaagctg agaagaaatc tgcagaacaa tgctgagtgg gtttatcaag    12480
gggccattag gcaaattgat gatatcgacg tgaggttcca gaaagcagcc agtggcacca    12540
ctgggaccta ccaagagtgg aaggacaagg cccagaatct gtaccaggaa ctgttgactc    12600
aggaaggcca agccagtttc cagggactca aggataacgt gtttgatggc ttggtacgag    12660
ttactcaaaa attccatatg aaagtcaagc atctgattga ctcactcatt gattttctga    12720
acttccccag attccagttt ccggggaaac ctgggatata cactagggag gaactttgca    12780
ctatgttcat aagggaggta gggacggtac tgtcccaggt atattcgaaa gtccataatg    12840
gttcagaaat actgttttcc tatttccaag acctagtgat tacacttcct ttcgagttaa    12900
ggaaacataa actaatagat gtaatctcga tgtatagggga actgttgaaa gatttatcaa    12960
aagaagccca agaggtattt aaagccattc agtctctcaa gaccacagag gtgctacgta    13020
atcttcagga cctttttacaa ttcattttcc aactaataga agataacatt aaacagctga    13080
aagagatgaa atttacttat cttattaatt atatccaaga tgagatcaac acaatcttca    13140
atgattatat cccatatgtt tttaaattgt tgaaagaaaa cctatgcctt aatcttcata    13200
agttcaatga atttattcaa aacgagcttc aggaagcttc tcaagagtta cagcagatcc    13260
atcaatacat tatggccctt cgtgaagaat attttgatcc aagtatagtt ggctggacag    13320
tgaaatatta tgaacttgaa gaaaagatag tcagtctgat caagaacctg ttagttgctc    13380
ttaaggactt ccattctgaa tatattgtca gtgcctctaa ctttacttcc caactctcaa    13440
gtcaagttga gcaatttctg cacagaaata ttcaggaata tcttagcatc cttaccgatc    13500
cagatggaaa agggaaagag aagattgcag agctttctgc cactgctcag gaaataatta    13560
aaagccaggc cattgcgacg aagaaaataa tttctgatta ccaccagcag tttagatata    13620
aactgcaaga ttttttcagac caactctctg attactatga aaaatttatt gctgaatcca    13680
aaagattgat tgacctgtcc attcaaaact accacacatt tctgatatac atcacggagt    13740 tactgaaaaaa gctgcaatca accacagtca tgaacccccta catgaagctt gctccaggag    13800
aacttactat catcctctaa ttttttaaaa gaaatcttca tttattcttc ttttccaatt    13860
gaactttcac atagcacaga aaaaattcaa actgcctata ttgataaaac catacagtga    13920
```

```
gccagccttg cagtaggcag tagactataa gcagaagcac atatgaactg gacctgcacc    13980
aaagctggca ccagggctcg gaaggtctct gaactcagaa ggatggcatt ttttgcaagt    14040
taaagaaaat caggatctga gttattttgc taaacttggg ggaggaggaa caaataaatg    14100
gagtctttat tgtgtatcat a                                              14121
```

<210> SEQ ID NO 2
<211> LENGTH: 14121
<212> TYPE: DNA
<213> ORGANISM: H. sapiens

<400> SEQUENCE: 2

```
attcccaccg ggacctgcgg ggctgagtgc ccttctcggt tgctgccgct gaggagcccg      60
cccagccagc cagggccgcg aggccgaggc caggccgcag cccaggagcc gccccaccgc     120
agctggcgat ggacccgccg aggcccgcgc tgctggcgct gctggcgctg cctgcgctgc     180
tgctgctgct gctggcgggc gccagggccg aagaggaaat gctggaaaat gtcagcctgg     240
tctgtccaaa agatgcgacc cgattcaagc acctccggaa gtacacatac aactatgagg     300
ctgagagttc cagtggagtc cctgggactg ctgattcaag aagtgccacc aggatcaact     360
gcaaggttga gctggaggtt ccccagctct gcagcttcat cctgaagacc agccagtgca     420
ccctgaaaga ggtgtatggc ttcaaccctg agggcaaagc cttgctgaag aaaaccaaga     480
actctgagga gtttgctgca gccatgtcca ggtatgagct caagctggcc attccagaag     540
ggaagcaggt tttcctttac ccggagaaag atgaacctac ttacatcctg aacatcaaga     600
ggggcatcat ttctgccctc ctggttcccc cagagacaga agaagccaag caagtgttgt     660
ttctggatac cgtgtatgga aactgctcca ctcactttac cgtcaagacg aggaagggca     720
atgtggcaac agaaatatcc actgaaagag acctggggca gtgtgatcgc ttcaagccca     780
tccgcacagg catcagccca cttgctctca tcaaaggcat gacccgcccc ttgtcaactc     840
tgatcagcag cagccagtcc tgtcagtaca cactggacgc taagaggaag catgtggcag     900
aagccatctg caaggagcaa caccctcttc ctgcctttctc ctacaagaat aagtatggga     960
tggtagcaca agtgacacag actttgaaac ttgaagacac accaaagatc aacagccgct    1020
tctttggtga aggtactaag aagatgggcc tcgcatttga gagcaccaaa tccacatcac    1080 ctcccaaagca ggccgaagct gttttgaaga ctctccagga actgaaaaaa ctaaccatct    1140
ctgagcaaaa tatccagaga gctaatctct tcaataagct ggttactgag ctgagaggcc    1200
tcagtgatga agcagtcaca tctctcttgc cacagctgat tgaggtgtcc agccccatca    1260
ctttacaagc cttggttcag tgtggacagc tcagtgctc cactcacatc ctccagtggc    1320
tgaaacgtgt gcatgccaac cccttctga tagatgtggt cacctacctg gtggccctga    1380
tccccgagcc ctcagcacag cagctgcgag agatcttcaa catggcgagg gatcagcgca    1440
gccgagccac cttgtatgcg ctgagccacg cggtcaacaa ctatcataag acaaacccta    1500
cagggaccca ggagctgctg acattgcta attacctgat ggaacagatt caagatgact    1560
gcactgggga tgaagattac acctatttga ttctgcgggt cattggaaat atgggccaaa    1620
ccatggcagc gttaactcca gaactcaagt cttcaatcct gaaatgtgtc caaagtacaa    1680
agccatcact gatgatccag aaagctgcca tccaggctct gcggaaaatg gagcctaaag    1740
acaaggacca ggaggttctt cttcagactt ccttgatga tgcttctccg ggagataagc    1800
gactggctgc ctatcttatg ttgatgagga gtccttcaca ggcagatatt aacaaaattg    1860
tccaaattct accatgggaa cagaatgagc aagtgaagaa cttttgtggct tcccatattg    1920
```

```
ccaatatctt gaactcagaa gaattggata tccaagatct gaaaaagtta gtgaaagaag    1980
ctctgaaaga atctcaactt ccaactgtca tggacttcag aaaattctct cggaactatc    2040
aactctacaa atctgtttct cttccatcac ttgacccagc tcagccaaa atagaaggga     2100
atcttatatt tgatccaaat aactaccttc ctaaagaaag catgctgaaa actaccctca    2160
ctgcctttgg atttgcttca gctgacctca tcgagattgg cttggaagga aaaggctttg    2220
agccaacatt ggaagctctt tttgggaagc aaggattttt cccagacagt gtcaacaaag    2280
ctttgtactg ggttaatggt caagttcctg atggtgtctc taaggtctta gtggaccact    2340
ttggctatac caaagatgat aaacatgagc aggatatggt aaatggaata atgctcagtg    2400
ttgagaagct gattaaagat ttgaaatcca agaagtccc ggaagccaga gcctacctcc     2460
gcatcttggg agaggagctt ggttttgcca gtctccatga cctccagctc ctgggaaagc    2520
tgcttctgat gggtgcccgc actctgcagg ggatccccca tgattggag aggtcatca     2580
ggaagggctc aaagaatgac ttttttcttc actacatctt catggagaat gcctttgaac    2640
tccccactgg agctggatta cagttgcaaa tatcttcatc tggagtcatt gctcccggag    2700
ccaaggctga gtaaaactg gaagtagcca acatgcaggc tgaactggtg caaaaccct      2760
ccgtgtctgt ggagtttgtg acaaatatgg gcatcatcat tccggacttc gctaggagtg    2820
gggtccagat gaacaccaac ttcttccacg agtcgggtct ggaggctcat gttgccctaa    2880
aagctgggaa gctgaagttt atcattcctt cccaaagag accagtcaag ctgctcagtg     2940
gaggcaacac attacatttg gtctctacca ccaaaacgga ggtgatccca cctctcattg    3000
agaacaggca gtcctggtca gtttgcaagc aagtctttcc tggcctgaat tactgcacct    3060
caggcgctta ctccaacgcc agctccacag actccgcctc ctactatccg ctgaccgggg    3120
acaccagatt agagctggaa ctgaggccta caggagagat tgagcagtat tctgtcagcg    3180
caacctatga gctccagaga gaggacagag ccttggtgga taccctgaag tttgtaactc    3240
aagcagaagg tgcgaagcag actgaggcta ccatgacatt caaatataat cggcagagta    3300
tgaccttgtc cagtgaagtc caaattccgg attttgatgt tgacctcgga acaatcctca    3360
gagttaatga tgaatctact gagggcaaaa cgtcttacag actcaccctg acattcaga    3420
acaagaaaat tactgaggtc gccctcatgg ccacctaag ttgtgacaca aaggaagaaa     3480
gaaaaatcaa gggtgttatt tccatacccc gtttgcaagc agaagccaga agtgagatcc    3540
tcgcccactg gtcgcctgcc aaactgcttc tccaaatgga ctcatctgct acagcttatg    3600
gctccacagt ttccaagagg gtggcatggc attatgatga agaagatt gaatttgaat      3660
ggaacacagg caccaatgta gataccaaaa aaatgacttc caatttccct gtggatctct    3720
ccgattatcc taagagcttg catatgtatg ctaatagact cctggatcac agagtccctc    3780
aaacagacat gactttccgg cacgtgggtt ccaaattaat agttgcaatg agctcatggc    3840
ttcagaaggc atctggagt cttccttata cccagacttt gcaagaccac ctcaatagcc     3900
tgaaggagtt caacctccag aacatgggat tgccagactt ccacatccca gaaaacctct    3960
tcttaaaaag cgatggccgg gtcaaatata ccttgaacaa gaacagtttg aaaattgaga    4020
ttccttttgcc ttttggtggc aaatcctcca gagatctaaa gatgttagag actgttagga    4080
caccagccct ccacttcaag tctgtgggat tccatctgcc atctcgagag ttccaagtcc    4140
ctacttttac cattcccaag ttgtatcaac tgcaagtgcc ctcctgggt gttctagacc     4200
tctccacgaa tgtctacagc aacttgtaca actggtccgc ctcctacagt ggtggcaaca    4260
```

```
ccagcacaga ccatttcagc cttcgggctc gttaccacat gaaggctgac tctgtggttg    4320
acctgctttc ctacaatgtg caaggatctg gagaaacaac atatgaccac aagaatacgt    4380
tcacactatc atgtgatggg tctctacgcc acaaatttct agattcgaat atcaaattca    4440
gtcatgtaga aaaacttgga aacaacccag tctcaaaagg tttactaata ttcgatgcat    4500
ctagttcctg gggaccacag atgtctgctt cagttcattt ggactccaaa agaaacagc     4560 atttgtttgt caagaagtc aagattgatg ggcagttcag agtctcttcg ttctatgcta     4620
aaggcacata tggcctgtct tgtcagaggg atcctaacac tggccggctc aatggagagt    4680
ccaacctgag gtttaactcc tcctacctcc aaggcaccaa ccagataaca ggaagatatg    4740
aagatggaac cctctccctc acctccacct ctgatctgca aagtggcatc attaaaaata    4800
ctgcttccct aaagtatgag aactacgagc tgactttaaa atctgacacc aatgggaagt    4860
ataagaactt tgccacttct aacaagatgg atatgacctt ctctaagcaa aatgcactgc    4920
tgcgttctga atatcaggct gattacgagt cattgaggtt cttcagcctg ctttctggat    4980
cactaaattc ccatggtctt gagttaaatg ctgcatctt aggcactgac aaaattaata    5040
gtggtgctca caaggcgaca ctaaggattg gccaagatgg aatatctacc agtgcaacga    5100
ccaacttgaa gtgtagtctc ctggtgctgg agaatgagct gaatgcagag cttggcctct    5160
ctggggcatc tatgaaatta acaacaaatg gccgcttcag ggaacacaat gcaaaattca    5220
gtctggatgg gaaagccgcc ctcacagagc tatcactggg aagtgcttat caggccatga    5280
ttctgggtgt cgacagcaaa acatttttca acttcaaggt cagtcaagaa ggacttaagc    5340
tctcaaatga catgatgggc tcatatgctg aaatgaaatt tgaccacaca aacagtctga    5400
acattgcagg cttatcactg gacttctctt caaaacttga caacatttac agctctgaca    5460
agttttataa gcaaactgtt aatttacagc tacagcccta ttctctggta actactttaa    5520
acagtgacct gaaatacaat gctctggatc tcaccaacaa tgggaaacta cggctagaac    5580
ccctgaagct gcatgtggct ggtaacctaa aaggagccta ccaaaataat gaaataaaac    5640
acatctatgc catctcttct gctgccttat cagcaagcta taaagcagac actgttgcta    5700
aggttcaggg tgtggagttt agccatcggc tcaacacaga catcgctggg ctggcttcag    5760
ccattgacat gagcacaaac tataattcag actcactgca tttcagcaat gtcttccgtt    5820
ctgtaatggc cccgtttacc atgaccatcg atgcacatac aaatggcaat gggaaactcg    5880
ctctctgggg agaacatact gggcagctgt atagcaaatt cctgttgaaa gcagaacctc    5940
tggcatttac tttctctcat gattacaaag gctccacaag tcatcatctc gtgtctagga    6000
aaagcatcag tgcagctctt gaacacaaag tcagtgccct gcttactcca gctgagcaga    6060
caggcacctg gaaactcaag acccaattta caacaatga atacagccag gacttggatg     6120
cttacaacac taaagataaa attggcgtgg agcttactgg acgaactctg ctgacctaa     6180 ctctactaga ctccccaatt aaagtgccac ttttactcag tgagcccatc aatatcattg    6240
atgctttaga gatgagagat gccgttgaga agccccaaga atttacaatt gttgcttttg    6300
taaagtatga taaaaccaa gatgttcact ccattaacct cccatttttt gagaccttgc     6360
aagaatattt tgagaggaat cgacaaacca ttatagttgt actggaaaac gtacagagaa    6420
acctgaagca catcaatatt gatcaatttg taagaaaata cagagcagcc ctgggaaaac    6480
tcccacagca agctaatgat tatctgaatt cattcaattg ggagagacaa gtttcacatg    6540
ccaaggagaa actgactgct ctcacaaaaa agtatagaat tacagaaaat gatatacaaa    6600
ttgcattaga tgatgccaaa atcaacttta atgaaaaact atctcaactg cagacatata    6660
```

```
tgatacaatt tgatcagtat attaaagata gttatgattt acatgatttg aaaatagcta   6720
ttgctaatat tattgatgaa atcattgaaa aattaaaaag tcttgatgag cactatcata   6780
tccgtgtaaa tttagtaaaa acaatccatg atctacattt gtttattgaa atattgatt    6840
ttaacaaaag tggaagtagt actgcatcct ggattcaaaa tgtggatact aagtaccaaa   6900
tcagaatcca gatacaagaa aaactgcagc agcttaagag acacatacag aatatagaca   6960
tccagcacct agctggaaag ttaaaacaac acattgaggc tattgatgtt agagtgcttt   7020
tagatcaatt gggaactaca atttcatttg aaagaataaa tgacgttctt gagcatgtca   7080
aacactttgt tataaatctt attggggatt ttgaagtagc tgagaaaatc aatgccttca   7140
gagccaaagt ccatgagtta atcgagaggt atgaagtaga ccaacaaatc caggttttaa   7200
tggataaatt agtagagttg gcccaccaat acaagttgaa ggagactatt cagaagctaa   7260
gcaatgtcct acaacaagtt aagataaaag attactttga gaaattggtt ggatttattg   7320
atgatgctgt caagaagctt aatgaattat cttttaaaac attcattgaa gatgttaaca   7380
aattccttga catgttgata aagaaattaa agtcatttga ttaccaccag tttgtagatg   7440
aaaccaatga caaaatccgt gaggtgactc agagactcaa tggtgaaatt caggctctgg   7500
aactaccaca aaaagctgaa gcattaaaac tgttttaga ggaaaccaag gccacagttg    7560
cagtgtatct ggaaagccta caggacacca aaataacctt aatcatcaat tggttacagg   7620
aggctttaag ttcagcatct ttggctcaca tgaaggccaa attccgagag accctagaag   7680
atacacgaga ccgaatgtat caaatggaca ttcagcagga acttcaacga tacctgtctc   7740
tggtaggcca ggtttatagc acacttgtca cctacatttc tgattggtgg actcttgctg   7800
ctaagaacct tactgacttt gcagagcaat attctatcca agattgggct aaacgtatga   7860
aagcattggt agagcaaggg ttcactgttc ctgaaatcaa gaccatcctt gggaccatgc   7920
ctgcctttga agtcagtctt caggctcttc agaaagctac cttccagaca cctgattta    7980
tagtccccct aacagatttg aggattccat cagttcagat aaacttcaaa gacttaaaaa   8040
atataaaaat cccatccagg ttttccacac cagaatttac catccttaac accttccaca   8100
ttccttcctt tacaattgac tttgtagaaa tgaaagtaaa gatcatcaga accattgacc   8160
agatgctgaa cagtgagctg cagtggcccg ttccagatat atatctcagg gatctgaagg   8220
tggaggacat tcctctagcg agaatcaccc tgccagactt ccgtttacca gaaatcgcaa   8280
ttccagaatt cataatccca actctcaacc ttaatgattt tcaagttcct gaccttcaca   8340
taccagaatt ccagcttccc cacatctcac acacaattga agtacctact tttggcaagc   8400
tatacagtat tctgaaaatc caatctcctc ttttcacatt agatgcaaat gctgacatag   8460
ggaatggaac cacctcagca aacgaagcag gtatcgcagc ttccatcact gccaaaggag   8520
agtccaaatt agaagttctc aattttgatt ttcaagcaaa tgcacaactc tcaaacccta   8580
agattaatcc gctggctctg aaggagtcag tgaagttctc cagcaagtac ctgagaacgg   8640
agcatgggag tgaaatgctg ttttttggaa atgctattga gggaaaatca acacacagtgg  8700
caagtttaca cacagaaaaa aatacactgg agcttagtaa tggagtgatt gtcaagataa   8760
acaatcagct taccctggat agcaacacta aatacttcca caaattgaac atccccaaac   8820
tggacttctc tagtcaggct gacctgcgca acgagatcaa gacactgttg aaagctggcc   8880
acatagcatg gacttcttct ggaaaagggt catggaaatg gcctgcccc agattctcag    8940
atgagggaac acatgaatca caaattagtt tcaccataga aggacccctc acttcctttg   9000
```

```
gactgtccaa taagatcaat agcaaacacc taagagtaaa ccaaaacttg gtttatgaat    9060
ctggctccct caacttttct aaacttgaaa ttcaatcaca agtcgattcc cagcatgtgg    9120
gccacagtgt tctaactgct aaaggcatgg cactgtttgg agaagggaag gcagagttta    9180 ctggaggca tgatgctcat ttaaatggaa aggttattgg aactttgaaa aattctcttt    9240
tcttttcagc ccagccattt gagatcacgg catccacaaa caatgaaggg aatttgaaag    9300
ttcgttttcc attaaggtta acagggaaga tagacttcct gaataactat gcactgtttc    9360
tgagtcccag tgcccagcaa gcaagttggc aagtaagtgc taggttcaat cagtataagt    9420
acaaccaaaa tttctctgct ggaaacaacg agaacattat ggaggcccat gtaggaataa    9480
atggagaagc aaatctggat ttcttaaaca ttcctttaac aattcctgaa atgcgtctac    9540
cttacacaat aatcacaact cctccactga agatttctc tctatgggaa aaaacaggct    9600
tgaaggaatt cttgaaaacg acaaagcaat catttgattt aagtgtaaaa gctcagtata    9660
agaaaaacaa acacaggcat tccatcacaa atcctttggc tgtgctttgt gagtttatca    9720
gtcagagcat caaatccttt gacaggcatt ttgaaaaaaa cagaaacaat gcattagatt    9780
ttgtcaccaa atcctataat gaaacaaaaa ttaagtttga taagtacaaa gctgaaaaat    9840
ctcacgacga gctccccagg acctttcaaa ttcctggata cactgttcca gttgtcaatg    9900
ttgaagtgtc tccattcacc atagagatgt cggcattcgg ctatgtgttc ccaaaagcag    9960
tcagcatgcc tagtttctcc atcctaggtt ctgacgtccg tgtgccttca tacacattaa   10020
tcctgccatc attagagctg ccagtccttc atgtccctag aaatctcaag ctttctcttc   10080
cagatttcaa ggaattgtgt accataagcc atattttat tcctgccatg ggcaatatta   10140
cctatgattt ctccttaaa tcaagtgtca tcacactgaa taccaatgct gaactttta   10200 accagtcaga tattgttgct catctccttt cttcatcttc atctgtcatt gatgcactgc   10260
agtacaaatt agagggcacc acaagattga caagaaaaag gggattgaag ttagccacag   10320
ctctgtctct gagcaacaaa tttgtggagg gtagtcataa cagtactgtg agcttaacca   10380
cgaaaaatat ggaagtgtca gtggcaacaa ccacaaaagc ccaaattcca attttgagaa   10440
tgaatttcaa gcaagaactt aatggaaata ccaagtcaaa acctactgtc tcttcctcca   10500
tggaatttaa gtatgatttc aattcttcaa tgctgtactc taccgctaaa ggagcagttg   10560
accacaagct tagcttggaa agcctcacct cttacttttc cattgagtca tctaccaaag   10620
gagatgtcaa gggttcggtt cttctctggg aatattcagg aactattgct agtgaggcca   10680
acacttactt gaattccaag agcacacggt cttcagtgaa gctgcagggc acttccaaaa   10740
ttgatgatat ctggaacctt gaagtaaaag aaaattttgc tggagaagcc acactccaac   10800
gcatatattc cctctgggag cacagtacga aaaaccactt acagctagag ggcctctttt   10860
tcaccaacgg agaacataca agcaaagcca ccctggaact ctctccatgg caaatgtcag   10920
ctcttgttca ggtccatgca agtcagccca gttccttcca tgatttccct gaccttggcc   10980
aggaagtggc cctgaatgct aacactaaga accagaagat cagatggaaa aatgaagtcc   11040
ggattcattc tgggtctttc cagagccagg tcgagctttc caatgaccaa gaaaaggcac   11100
accttgacat tgcaggatcc ttagaaggac acctaaggtt cctcaaaaat atcatcctac   11160
cagtctatga caagagctta tgggatttcc taaagctgga tgtaaccacc agcattggta   11220
ggagacagca tctcgtgtt tcaactgcct ttgtgtacac caaaaacccc aatggctatt   11280
cattctccat ccctgtaaaa gttttggctg ataaattcat tattcctggg ctgaaactaa   11340
atgatctaaa ttcagttctt gtcatgccta cgttccatgt cccatttaca gatcttcagg   11400
```

```
ttccatcgtg caaacttgac ttcagagaaa tacaaatcta taagaagctg agaacttcat    11460
catttgccct caacctacca acactccccg aggtaaaatt ccctgaagtt gatgtgttaa    11520
caaaatattc tcaaccagaa gactccttga ttccctttt tgagataacc gtgcctgaat    11580
ctcagttaac tgtgtcccag ttcacgcttc caaaaagtgt ttcagatggc attgctgctt    11640
tggatctaaa tgcagtagcc aacaagatcg cagactttga gttgcccacc atcatcgtgc    11700
ctgagcagac cattgagatt ccctccatta agttctctgt acctgctgga attgtcattc    11760
cttcctttca agcactgact gcacgctttg aggtagactc tcccgtgtat aatgccactt    11820
ggagtgccag tttgaaaaac aaagcagatt atgttgaaac agtcctggat tccacatgca    11880
gctcaaccgt acagttccta gaatatgaac taaatgtttt gggaacacac aaaatcgaag    11940
atggtacgtt agcctctaag actaaaggaa catttgcaca ccgtgacttc agtgcagaat    12000
atgaagaaga tggcaaatat gaaggacttc aggaatggga aggaaaagcg cacctcaata    12060
tcaaaagccc agcgttcacc gatctccatc tgcgctacca gaaagacaag aaaggcatct    12120
ccacctcagc agcctcccca gccgtaggca ccgtgggcat ggatatggat gaagatgacg    12180
acttttctaa atggaacttc tactacagcc ctcagtcctc tccagataaa aaactcacca    12240
tattcaaaac tgagttgagg gtccgggaat ctgatgagga aactcagatc aaagttaatt    12300
gggaagaaga ggcagcttct ggcttgctaa cctctctgaa agacaacgtg cccaaggcca    12360 cagggtcct ttatgattat gtcaacaagt accactggga acacacaggg ctcaccctga    12420
gagaagtgtc ttcaaagctg agaagaaatc tgcagaacaa tgctgagtgg gtttatcaag    12480
gggccattag gcaaattgat gatatcgacg tgaggttcca gaaagcagcc agtggcacca    12540
ctgggaccta ccaagagtgg aaggacaagg cccagaatct gtaccaggaa ctgttgactc    12600
aggaaggcca agccagtttc cagggactca aggataacgt gtttgatggc ttggtacgag    12660
ttactcaaga attccatatg aaagtcaagc atctgattga ctcactcatt gattttctga    12720
acttccccag attccagttt ccggggaaac ctgggatata cactagggag gaactttgca    12780
ctatgttcat aagggaggta gggacggtac tgtcccaggt atattcgaaa gtccataatg    12840
gttcagaaat actgttttcc tatttccaag acctagtgat tacacttcct ttcgagttaa    12900
ggaaacataa actaatagat gtaatctcga tgtataggga actgttgaaa gatttatcaa    12960
aagaagccca agaggtattt aaagccattc agtctctcaa gaccacagag gtgctacgta    13020
atcttcagga cctttacaa ttcatttttc aactaataga agataacatt aaacagctga    13080
aagagatgaa atttacttat cttattaatt atatccaaga tgagatcaac acaatcttca    13140
gtgattatat cccatatgtt tttaaattgt tgaaagaaaa cctatgcctt aatcttcata    13200
agttcaatga atttattcaa aacgagcttc aggaagcttc tcaagagtta cagcagatcc    13260
atcaatacat tatggccctt cgtgaagaat attttgatcc aagtatagtt ggctggacag    13320
tgaaatatta tgaacttgaa gaaaagatag tcagtctgat caagaacctg ttagttgctc    13380
ttaaggactt ccattctgaa tatattgtca gtgcctctaa ctttacttcc caactctcaa    13440
gtcaagttga gcaatttctg cacagaaata ttcaggaata tcttagcatc cttaccgatc    13500
cagatggaaa agggaaagag aagattgcag agctttctgc cactgctcag gaaataatta    13560
aaagccaggc cattgcgacg aagaaaataa tttctgatta ccaccagcag tttagatata    13620
aactgcaaga tttttcagac caactctctg attactatga aaaatttatt gctgaatcca    13680
aaagattgat tgacctgtcc attcaaaact accacacatt tctgatatac atcacggagt    13740
```

```
tactgaaaaa gctgcaatca accacagtca tgaaccccta catgaagctt gctccaggag   13800
aacttactat catcctctaa ttttttaaaa gaaatcttca tttattcttc ttttccaatt   13860
gaactttcac atagcacaga aaaaattcaa actgcctata ttgataaaac catacagtga   13920
gccagccttg cagtaggcag tagactataa gcagaagcac atatgaactg gacctgcacc   13980
aaagctggca ccagggctcg gaaggtctct gaactcagaa ggatggcatt ttttgcaagt   14040
taaagaaaat caggatctga gttatttttgc taaacttggg ggaggaggaa caaataaatg   14100
gagtctttat tgtgtatcat a                                             14121

<210> SEQ ID NO 3
<211> LENGTH: 600
<212> TYPE: DNA
<213> ORGANISM: H. sapiens

<400> SEQUENCE: 3
aattcattca attgggagag acaagtttca catgccaagg agaaactgac tgctctcaca     60
aaaaagtata gaattacaga aaatgatata caaattgcat tagatgatgc caaaatcaac    120
tttaatgaaa aactatctca actgcagaca tatatgatat aatttgatca gtatattaaa    180
gatagttatg atttacatga tttgaaaata gctattgcta atattattga tgaaatcatt    240
gaaaaattaa aaagtcttga tgagcactat catatccgtg taaatttagt aaaaacaatc    300
catgatctac atttgtttat tgaaaatatt gattttaaca aaagtggaag tagtactgca    360
tcctggattc aaaatgtgga tactaagtac caaatcagaa tccagataca agaaaaactg    420
cagcagctta agagacacat acagaatata gacatccagc acctagctgg aaagttaaaa    480
caacacattg aggctattga tgttagagtg cttttagatc aattgggaac tacaatttca    540
tttgaaagaa taaatgatgt tcttgagcat gtcaaacact tgttataaa tcttattggg    600

<210> SEQ ID NO 4
<211> LENGTH: 321
<212> TYPE: DNA
<213> ORGANISM: H. sapiens

<400> SEQUENCE: 4
ttcaattggg agagacaagt ttcacatgcc aaggagaaac tgactgctct cacaaaaaag     60
tatagaatta cagaaaatga tatacaaatt gcattagatg atgccaaaat caactttaat    120
gaaaaactat ctcaactgca gacatatatg atataatttg atcagtatat aaagatagt    180 tatgatttac atgatttgaa aatagctatt gctaatatta ttgatgaaat cattgaaaaa    240
ttaaaaagtc ttgatgagca ctatcatatc cgtgtaaatt tagtaaaaac aatccatgat    300
ctacatttgt ttattgaaaa t                                             321

<210> SEQ ID NO 5
<211> LENGTH: 660
<212> TYPE: DNA
<213> ORGANISM: H. sapiens

<400> SEQUENCE: 5
ctgggaaaac tcccacagca agctaatgat tatctgaatt cattcaattg ggagagacaa     60
gtttcacatg ccaaggagaa actgactgct ctcacaaaaa agtatagaat tacagaaaat    120
gatatacaaa ttgcattaga tgatgccaaa atcaacttta tgaaaaact atctcaactg    180 cagacatata tgatataatt tgatcagtat attaaagata gttatgattt acatgatttg    240
aaaatagcta ttgctaatat tattgatgaa atcattgaaa aattaaaaag tcttgatgag    300
```

| | | |
|---|---|---|
| cactatcata tccgtgtaaa tttagtaaaa acaatccatg atctacattt gtttattgaa | 360 |
| aatattgatt ttaacaaaag tggaagtagt actgcatcct ggattcaaaa tgtggatact | 420 |
| aagtaccaaa tcagaatcca gatacaagaa aaactgcagc agcttaagag acacatacag | 480 |
| aatatagaca tccagcacct agctggaaag ttaaaacaac acattgaggc tattgatgtt | 540 |
| agagtgcttt tagatcaatt gggaactaca atttcatttg aaagaataaa tgatgttctt | 600 |
| gagcatgtca acactttgt tataaatctt attggggatt ttgaagtagc tgagaaaatc | 660 |

<210> SEQ ID NO 6
<211> LENGTH: 14112
<212> TYPE: DNA
<213> ORGANISM: H. sapiens

<400> SEQUENCE: 6

| | | |
|---|---|---|
| attcccaccg ggacctgcgg ggctgagtgc ccttctcggt tgctgccgct gaggagcccg | 60 |
| cccagccagc cagggccgcg aggccgaggc caggccgcag cccaggagcc gccccaccgc | 120 |
| agctggcgat ggacccgccg aggcccgcgc tgctggcgct gcctgcgctg ctgctgctgc | 180 |
| tgctggcggg cgccagggcc gaagaggaaa tgctggaaaa tgtcagcctg gtctgtccaa | 240 |
| aagatgcgac ccgattcaag cacctccgga agtacacata caactatgag gctgagagtt | 300 |
| ccagtgggagt ccctgggact gctgattcaa gaagtgccac caggatcaac tgcaaggttg | 360 |
| agctggaggt tccccagctc tgcagcttca tcctgaagac cagccagtgc accctgaaag | 420 |
| aggtgtatgg cttcaaccct gagggcaaag ccttgctgaa gaaaaccaag aactctgagg | 480 |
| agtttgctgc agccatgtcc aggtatgagc tcaagctggc cattccagaa gggaagcagg | 540 |
| ttttcctta cccggagaaa gatgaaccta cttacatcct gaacatcaag aggggcatca | 600 |
| tttctgccct cctggttccc ccagagacag aagaagccaa gcaagtgttg tttctggata | 660 |
| ccgtgtatgg aaactgctcc actcacttta ccgtcaagac gagggaagggc aatgtggcaa | 720 |
| cagaaatatc cactgaaaga gacctgggcc agtgtgatcg cttcaagccc atccgcacag | 780 |
| gcatcagccc acttgctctc atcaaaggca tgacccgccc cttgtcaact ctgatcagca | 840 |
| gcagccagtc ctgtcagtac acactggacg ctaagaggaa gcatgtggca gaagccatct | 900 |
| gcaaggagca acacctcttc ctgccttct cctacaagaa taagtatggg atggtagcac | 960 |
| aagtgacaca gactttgaaa cttgaagaca caccaaagat caacagccgc ttctttggtg | 1020 |
| aaggtactaa gaagatgggc ctcgcatttg agagcaccaa atccacatca cctccaaagc | 1080 |
| aggccgaagc tgttttgaag actctccagg aactgaaaaa actaaccatc tctgagcaaa | 1140 |
| atatccagag agctaatctc ttcaataagc tggttactga gctgagaggc ctcagtgatg | 1200 |
| aagcagtcac atctctcttg ccacagctga ttgaggtgtc cagccccatc actttacaag | 1260 |
| ccttggttca gtgtggacag cctcagtgct ccactcacat cctccagtgg ctgaaacgtg | 1320 |
| tgcatgccaa ccccctctg atagatgtgg tcacctacct ggtggccctg atccccgagc | 1380 |
| cctcagcaca gcagctgcga gagatcttca acatggcgag ggatcagcgc agccgagcca | 1440 |
| ccttgtatgc gctgagccac gcggtcaaca ctatcataa gacaaaccct acagggaccc | 1500 |
| aggagctgct ggacattgct aattacctga tggaacagat tcaagatgac tgcactgggg | 1560 |
| atgaagatta cacctatttg attctgcggg tcattggaaa tatgggccaa accatggagc | 1620 |
| agttaactcc agaactcaag tcttcaatcc tgaaatgtgt ccaaagtaca aagccatcac | 1680 |
| tgatgatcca gaaagctgcc atccaggctc tgcggaaaat ggagcctaaa gacaaggacc | 1740 |

```
aggaggttct tcttcagact ttccttgatg atgcttctcc gggagataag cgactggctg    1800
cctatcttat gttgatgagg agtccttcac aggcagatat taacaaaatt gtccaaattc    1860
taccatggga acagaatgag caagtgaaga actttgtggc ttcccatatt gccaatatct    1920
tgaactcaga agaattggat atccaagatc tgaaaaagtt agtgaaagaa gttctgaaag    1980
aatctcaact tccaactgtc atggacttca gaaaattctc tcggaactat caactctaca    2040
aatctgtttc tcttccatca cttgacccag cctcagccaa aatagaaggg aatcttatat    2100
ttgatccaaa taactacctt cctaaagaaa gcatgctgaa aactaccctc actgcctttg    2160
gatttgcttc agctgacctc atcgagattg gcttggaagg aaaaggcttt gagccaacat    2220
tggaagctct ttttgggaag caaggatttt tcccagacag tgtcaacaaa gctttgtact    2280
gggttaatgg tcaagttcct gatggtgtct ctaaggtctt agtggaccac tttggctata    2340
ccaaagatga taaacatgag caggatatgg taaatggaat aatgctcagt gttgagaagc    2400
tgattaaaga tttgaaatcc aaagaagtcc cggaagccag agcctacctc cgcatcttgg    2460
gagaggagct tggttttgcc agtctccatg acctccagct cctgggaaag ctgcttctga    2520
tgggtgcccg cactctgcag gggatccccc agatgattgg agaggtcatc aggaagggct    2580
caaagaatga cttttttctt cactacatct tcatggagaa tgcctttgaa ctccccactg    2640
gagctggatt acagttgcaa atatcttcat ctggagtcat tgctcccgga gccaaggctg    2700
gagtaaaact ggaagtagcc aacatgcagg ctgaactggt ggcaaaaccc tccgtgtctg    2760
tggagtttgt gacaaatatg ggcatcatca ttccggactt cgctaggagt ggggtccaga    2820
tgaacaccaa cttcttccac gagtcgggtc tggaggctca tgttgcccta aaagctggga    2880
agctgaagtt tatcattcct tccccaaaga gaccagtcaa gctgctcagt ggaggcaaca    2940
cattacattt ggtctctacc accaaaacgg aggtgatccc acctctcatt gagaacaggc    3000
agtcctggtc agtttgcaag caagtctttc ctggcctgaa ttactgcacc tcaggcgctt    3060
actccaacgc cagctccaca gactccgcct cctactatcc gctgaccggg gacaccagat    3120
tagagctgga actgaggcct acaggagaga ttgagcagta ttctgtcagc gcaacctatg    3180
agctccagag agaggacaga gccttggtgg atacccctgaa gtttgtaact caagcagaag    3240
gtgcgaagca gactgaggct accatgacat caaatataa tcggcagagt atgaccttgt    3300
ccagtgaagt ccaaattccg gattttgatg ttgacctcgg aacaatcctc agagttaatg    3360
atgaatctac tgagggcaaa acgtcttaca gactcaccct ggacattcag aacaagaaaa    3420
ttactgaggt cgccctcatg ggcgacctaa gttgtgacac aaaggaagaa agaaaaatca    3480
agggtgttat ttccataccc cgtttgcaag cagaagccag aagtgagatc ctcgcccact    3540
ggtcgcctgc caaactgctt ctccaaatgg actcatctgc tacagcttat ggctccacag    3600
tttccaagag ggtggcatgg cattatgatg aagagaagat tgaatttgaa tggaacacag    3660
gcaccaatgt agataccaaa aaaatgactt ccaatttccc tgtggatctc tccgattatc    3720
ctaagagctt gcatatgtat gctaatagac tcctggatca cagagtccct caaacagaca    3780
tgactttccg gcacgtgggt tccaaattaa tagttgcaat gagctcatgg cttcagaagg    3840
catctgggag tcttccttat acccagactt tgcaagacca cctcaatagc ctgaaggagt    3900
tcaacctcca gaacatggga ttgccagact tccacatccc agaaaacctc ttcttaaaaa    3960
gcgatgccgg ggtcaaatat accttgaaca agaacagttt gaaaattgag attcctttgc    4020
cttttggtgg caaatcctcc agagatctaa agatgttaga gactgttagg acaccagccc    4080
tccacttcaa gtctgtggga ttccatctgc catctcgaga gttccaagtc cctacttta    4140
```

```
ccattcccaa gttgtatcaa ctgcaagtgc ctctcctggg tgttctagac ctctccacga   4200
atgtctacag caacttgtac aactggtccg cctcctacag tggtggcaac accagcacag   4260
accatttcag ccttcgggct cgttaccaca tgaaggctga ctctgtggtt gacctgcttt   4320
cctacaatgt gcaaggatct ggagaaacaa catatgacca caagaatacg tctacactat   4380
catgtgatgg gtctctacgc cacaaatttc tagattcgaa tatcaaattc agtcatgtag   4440
aaaaacttgg aaacaaccca gtctcaaaag gtttactaat attcgatgca tctagttcct   4500
ggggaccaca gatgtctgct tcagttcatt tggactccaa aaagaaacag catttgtttg   4560
tcaaagaagt caagattgat gggcagttca gagtctcttc gttctatgct aaaggcacat   4620
atggcctgtc ttgtcagagg gatcctaaca ctggccggct caatggagag tccaacctga   4680
ggtttaactc ctcctacctc caaggcacca accagataac aggaagatat gaagatggaa   4740
ccctctccct cacctccacc tctgatctgc aaagtggcat cattaaaaat actgcttccc   4800
taaagtatga gaactacgag ctgactttaa aatctgacac caatgggaag tataagaact   4860
ttgccacttc taacaagatg gatatgacct tctctaagca aaatgcactg ctgcgttctg   4920
aatatcaggc tgattacgag tcattgaggt tcttcagcct gctttctgga tcactaaatt   4980
cccatggtct tgagttaaat gctgacatct taggcactga caaaattaat agtggtgctc   5040
acaaggcgac actaaggatt ggccaagatg gaatatctac cagtgcaacg accaacttga   5100
agtgtagtct cctggtgctg gagaatgagc tgaatgcaga gcttggcctc tctggggcat   5160
ctatgaaatt aacaacaaat ggccgcttca gggaacacaa tgcaaaattc agtctggatg   5220
ggaaagccgc cctcacagag ctatcactgg gaagtgctta tcaggccatg attctgggtg   5280
tcgacagcaa aaacattttc aacttcaagg tcagtcaaga aggacttaag ctctcaaatg   5340
acatgatggg ctcatatgct gaaatgaaat tgaccacac aaacagtctg aacattgcag   5400
gcttatcact ggacttctct tcaaaacttg acaacattta cagctctgac aagtttttata  5460 agcaaactgt taatttacag ctacagccct attctctggt aactactta aacagtgacc   5520 tgaaatacaa tgctctggat ctcaccaaca atgggaaact acggctagaa ccctgaagc   5580 tgcatgtggc tggtaaccta aaaggagcct accaaaataa tgaaataaaa cacatctatg   5640
ccatctcttc tgctgcctta tcagcaagct ataaagcaga cactgttgct aaggttcagg   5700
gtgtggagtt tagccatcgg ctcaacacag acatcgctgg gctggcttca gccattgaca   5760
tgagcacaaa ctataattca gactcactgc atttcagcaa tgtcttccgt tctgtaatgg   5820
ccccgtttac catgaccatc gatgcacata caaatgcaa tgggaaactc gctctctggg   5880
gagaacatac tgggcagctg tatagcaaat tcctgttgaa agcagaacct ctggcattta   5940 cttttctctca tgattacaaa ggctccacaa gtcatcatct cgtgtctagg aaaagcatca   6000
gtgcagctct tgaacacaaa gtcagtgccc tgcttactcc agctgagcag acaggcacct   6060
ggaaactcaa gacccaattt aacaacaatg aatacagcca ggacttggat gcttacaaca   6120
ctaaagataa aattggcgtg gagcttactg gacgaactct ggctgaccta actctactag   6180 actcccaat taaagtgcca cttttactca gtgagcccat caatatcatt gatgctttag   6240
agatgagaga tgccgttgag aagccccaag aatttacaat tgttgctttt gtaaagtatg   6300
ataaaaacca agatgttcac tccattaacc tcccattttt tgagaccttg caagaatatt   6360
ttgagaggaa tcgacaaacc attatagttg tactggaaaa cgtacagaga aagctgaagc   6420
acatcaatat tgatcaattt gtaagaaaat acagagcagc cctgggaaaa ctcccacagc   6480
```

```
aagctaatga ttatctgaat tcattcaatt gggagagaca agtttcacat gccaaggaga    6540
aactgactgc tctcacaaaa aagtatagaa ttacagaaaa tgatatacaa attgcattag    6600
atgatgccaa aatcaacttt aatgaaaaac tatctcaact gcagacatat atgatacaat    6660
ttgatcagta tattaaagat agttatgatt tacatgattt gaaaatagct attgctaata    6720
ttattgatga aatcattgaa aaattaaaaa gtcttgatga gcactatcat atccgtgtaa    6780
ttttagtaaa aacaatccat gatctacatt tgtttattga aaatattgat tttaacaaaa    6840
gtggaagtag tactgcatct tggattcaaa atgtggatac taagtaccaa atcagaatcc    6900
agatacaaga aaaactgcag cagcttaaga gacacataca gaatatagac atccagcacc    6960
tagctggaaa gttaaaacaa cacattgagg ctattgatgt tagagtgctt ttagatcaat    7020
tgggaactac aatttcattt gaagaataaa atgacgttct tgagcatgtc aaacactttg    7080
ttataaatct tattggggat tttgaagtag ctgagaaaat caatgccttc agagccaaag    7140
tccatgagtt aatcgagagg tatgaagtag accaacaaat ccaggtttta atggataaat    7200
tagtagagtt ggcccaccaa tacaagttga aggagactat tcagaagcta agcaatgtcc    7260
tacaacaagt taagataaaa gattactttg agaaattagt tggatttatt gatgatgctg    7320
tcaagaagct taatgaatta tcttttaaaa cattcattga agatgttaac aaattccttg    7380
acatgttgat aaagaaatta aagtcatttg attaccacca gtttgtagat gaaaccaatg    7440
acaaaatccg tgaggtgact cagagactca atggtgaaat tcaggctctg gaactaccac    7500
aaaaagctga agcattaaaa ctgtttttag aggaaaccaa ggccacagtt gcagtgtatc    7560
tggaaagcct acaggacacc aaaataacct taatcatcaa ttggttacag gaggctttaa    7620
gttcagcatc tttggctcac atgaaggcca aattccgaga gaccctagaa gatacacgag    7680
accgaatgta tcaaatggac attcagcagg aacttcaacg atacctgtct ctggtcagcc    7740
aggtttatag cacacttgtc acctacattt ctgattggtg gactcttgct gctaagaacc    7800
ttactgactt tgcagagcaa tattctatcc aagattgggc taaacgtatg aaagcattgg    7860
tagagcaagg gttcactgtt cctgaaatca agaccatcct tgggaccatg cctgcctttg    7920
aagtcagtct tcaggctctt cagaaagcta ccttccagac acctgatttt atagtccccc    7980
taacagattt gaggattcca tcagttcaga taaacttcaa agacttaaaa aatataaaaa    8040
tcccatccag gttttccaca ccagaattta ccatccttaa caccttccac attccttcct    8100
ttacaattga ctttgtagaa atgaaagtaa agatcatcag aaccattgac cagatgctga    8160
acagtgagct gcagtggccc gttccagata tatatctcag ggatctgaag gtggaggaca    8220
ttcctctagc gagaatcacc ctgccagact tccgtttacc agaaatcgca ataccagaat    8280
tcataatccc aactctcaac cttaatgatt ttcaagttcc tgaccttcac ataccagaat    8340
tccagcttcc ccacatctca cacacaattg aagtacctac ttttggcaag ctatacagta    8400
ttctgaaaat ccaatctcct cttttcacat tagatgcaaa tgctgacata gggaatggaa    8460
ccacctcagc aaacgaagca ggtatcgcag cttccatcac tgccaaagga gagtccaaat    8520
tagaagttct caatttttgat tttcaagcaa atgcacaact ctcaaaccct aagattaatc    8580
cgctggctct gaaggagtca gtgaagttct ccagcaagta cctgagaacg gagcatggga    8640
gtgaaatgct gttttttgga aatgccattg agggaaaatc aaacacagtg gcaagtttac    8700
acacagaaaa aaatacactg gagcttagta atggagtgat tgtcaagata aacaatcagc    8760
ttaccctgga tagcaacact aaatacttcc acaaattgaa catccccaaa ctggacttct    8820
ctagtcaggc tgacctgcgc aacgagatca agacactgtt gaaagctggc cacatagcat    8880
```

```
ggacttcttc tggaaaaggg tcatggaaat gggcctgccc cagattctca gatgagggaa    8940
cacatgaatc acaaattagt ttcaccatag aaggacccct cacttccttt ggactgtcca    9000
ataagatcaa tagcaaacac ctaagagtaa accaaaactt ggtttatgaa tctggctccc    9060 tcaactttc taaacttgaa attcaatcac aagtcgattc ccagcatgtg ggccacagtg    9120
ttctaactgc taaaggcatg gcactgtttg gagaagggaa ggcagagttt actgggaggc    9180
atgatgctca tttaaatgga aaggttattg aactttgaa aaattctctt ttcttttcag    9240
cccagccatt tgagatcacg gcatccacaa acaatgaagg gaatttgaaa gttcgttttc    9300
cattaaggtt aacagggaag atagacttcc tgaataacta tgcactgttt ctgagtccca    9360
gtgcccagca agcaagttgg caagtaagtg ctaggttcaa tcagtataag tacaaccaaa    9420
atttctctgc tggaaacaac gagaacatta tggaggccca tgtaggaata aatggagaag    9480
caaatctgga tttcttaaac attcctttaa caattcctga aatgcgtcta ccttacacaa    9540
taatcacaac tcctccactg aaagatttct ctctatggga aaaaacaggc ttgaaggaat    9600
tcttgaaaac gacaaagcaa tcatttgatt taagtgtaaa agctcagtat aagaaaaaca    9660
aacacaggca ttccatcaca aatcctttgg ctgtgctttg tgagtttatc agtcagagca    9720
tcaaatcctt tgacaggcat tttgaaaaaa acagaaacaa tgcattagat tttgtcacca    9780
aatcctataa tgaaacaaaa attaagtttg ataagtacaa agctgaaaaa tctcaggacg    9840
agctccccag gacctttcaa attcctggat acactgttcc agttgtcaat gttgaagtgt    9900
ctccattcac catagagatg tcggcattcg gctatgtgtt cccaaaagca gtcagcatgc    9960
ctagtttctc catcctaggt tctgacgtcc gtgtgccttc atacacatta atcctgccat   10020
cattagagct gccagtcctt catgtcccta gaaatctcaa gctttctctt ccacatttca   10080
aggaattgtg taccataagc catatttta ttcctgccat gggcaatatt acctatgatt   10140
tctcctttaa atcaagtgtc atcacactga ataccaatgc tgaacttttt aaccagtcag   10200
atattgttgc tcatctcctt tcttcatctt catctgtcat tgatgcactg cagtacaaat   10260
tagagggcac cacaagattg acaagaaaaa ggggattgaa gttagccaca gctctgtctc   10320
tgagcaacaa atttgtggag ggtagtcata acagtactgt gagcttaacc acgaaaaata   10380
tggaagtgtc agtggcaaaa accacaaaag ccgaaattcc aattttgaga atgaatttca   10440
agcaagaact taatgaaaat accaagtcaa aacctactgt ctcttcctcc atggaattta   10500
agtatgattt caattcttca atgctgtact ctaccgctaa aggagcagtt gaccacaagc   10560
ttagcttgga aagcctcacc tcttactttt ccattgagtc atctaccaaa ggagatgtca   10620
agggttcggt tctttctcgg gaatattcag gaactattgc tagtgaggcc aacacttact   10680
tgaattccaa gagcacacgg tcttcagtga agctgcaggg cacttccaaa attgatgata   10740
tctggaacct tgaagtaaaa gaaaattttg ctggagaagc cacactccaa cgcatatatt   10800
ccctctggga gcacagtacg aaaaaccact tacagctaga gggcctcttt ttcaccaacg   10860
gagaacatac aagcaaagcc accctggaac tctctccatg gcaaatgtca gctcttgttc   10920
aggtccatgc aagtcagccc agttccttcc atgatttccc tgaccttggc caggaagtgg   10980
ccctgaatgc taacactaag aaccagaaga tcagatggaa aaatgaagtc cggattcatt   11040
ctgggtcttt ccagagccag gtcgagcttt ccaatgacca agaaaaggca caccttgaca   11100
ttgcaggatc cttagaagga cacctaaggt tcctcaaaaa tatcatccta ccagtctatg   11160
acaagagctt atgggatttc ctaaagctgg atgtaaccac cagcattggt aggagacagc   11220
```

-continued

```
atcttcgtgt ttcaactgcc tttgtgtaca ccaaaaaccc caatggctat tcattctcca    11280
tccctgtaaa agttttggct gataaattca ttactcctgg gctgaaacta atgatctaa    11340 attcagttct tgtcatgcct acgttccatg tcccatttac agatcttcag gttccatcgt    11400
gcaaacttga cttcagagaa atacaaatct ataagaagct gagaacttca tcatttgccc    11460
tcaacctacc aacactcccc gaggtaaaat tccctgaagt tgatgtgtta acaaaatatt    11520
ctcaaccaga agactccttg attccctttt ttgagataac cgtgcctgaa tctcagttaa    11580
ctgtgtcccg attcacgctt ccaaaaagtg tttcagatgg cattgctgct ttggatctaa    11640
atgcagtagc caacaagatc gcagactttg agttgcccac catcatcgtg cctgagcaga    11700
ccattgagat tccctccatt aagttctctg tacctgctgg aattgtcatt ccttcctttc    11760
aagcactgac tgcacgcttt gaggtagact ctcccgtgta taatgccact tggagtgcca    11820
gtttgaaaaa caaagcagat tatgttgaaa cagtcctgga ttccacatgc agctcaaccg    11880
tacagttcct agaatatgaa ctaaatgttt tgggaacaca caaaatcgaa gatggtacgt    11940
tagcctctaa gactaaagga acacttgcac accgtgactt cagtgcagaa tatgaagaag    12000
atggcaaatt tgaaggactt caggaatggg aaggaaaagc gcacctcaat atcaaaagcc    12060
cagcgttcac cgatctccat ctgcgctacc agaaagacaa gaaaggcatc tccacctcag    12120
cagcctcccc agccgtaggc accgtgggca tggatatgga tgaagatgac gacttttcta    12180
aatgaacttc ctactacagc cctcagtcct ctccagataa aaaactcacc atattcaaaa    12240
ctgagttgag ggtccgggaa tctgatgagg aaactcagat caaagttaat tgggaagaag    12300
aggcagcttc tggcttgcta acctctctga agacaacgt gcccaaggcc acagggtcc     12360 tttatgatta tgtcaacaag taccactggg aacacacagg gctcaccctg agagaagtgt    12420
cttcaaagct gagaagaaat ctgcagaaca atgctgagtg ggtttatcaa ggggccatta    12480
ggcaaattga tgatatcgac gtgaggttcc agaaagcagc cagtggcacc actgggacct    12540
accaagagtg gaaggacaag gcccagaatc tgtaccagga actgttgact caggaaggcc    12600
aagccagttt ccagggactc aaggataacg tgtttgatgg cttggtacga gttactcaaa    12660
aattccatat gaaagtcaag catctgattg actcactcat tgattttctg aacttccccca   12720 gattccagtt tccggggaaa cctgggatat acactaggga ggaactttgc actatgttca    12780
taagggaggt agggacggta ctgtcccagg tatattcgaa agtccataat ggttcagaaa    12840
tactgttttc ctatttccaa gacctagtga ttacacttcc tttcgagtta aggaaacata    12900
aactaataga tgtaatctcg atgtatagggaactgttgaa agatttatca aaagaagccc     12960
aagaggtatt taaagccatt cagtctctca agaccacaga ggtgctacgt aatcttcagg    13020
accttttaca attcattttc caactaatag aagataacat taaacagctg aaagagatga    13080
aatttactta tcttattaat tatatccaag atgagatcaa cacaatcttc aatgattata    13140
tcccatatgt ttttaaattg ttgaaagaaa acctatgcct taatcttcat aagttcaatg    13200
aatttattca aaacgagctt caggaagctt ctcaagagtt acagcagatc catcaataca    13260
ttatggccct tcgtgaagaa tattttgatc caagtatagt tggctggaca gtgaaatatt    13320
atgaacttga agaaaagata gtcagtctga tcaagaacct gttagttgct cttaaggact    13380
tccattctga atatattgtc agtgcctcta actttacttc ccaactctca gtcaagttg     13440 agcaatttct gcacagaaat attcaggaat atcttagcat ccttaccgat ccagatggaa    13500
aagggaaaga gaagattgca gagctttctg ccactgctca ggaataatt aaaagccagg      13560 ccattgcgac gaagaaaata atttctgatt accaccagca gtttagatat aaactgcaag    13620
```

-continued

```
atttttcaga ccaactctct gattactatg aaaaatttat tgctgaatcc aaaagattga    13680
ttgacctgtc cattcaaaac taccacacat ttctgatata catcacggag ttactgaaaa    13740
agctgcaatc aaccacagtc atgaacccct acatgaagct tgctccagga gaacttacta    13800
tcatcctcta attttttaaa agaaatcttc aatttattct tcttttccaa ttgaactttc    13860
acatagcaca gaaaaaattc aaactgccta tattgataaa accatacagt gagccagcct    13920
tgcagtaggc agtagactat aagcagaagc acatatgaac tggacctgca ccaaagctgg    13980
caccagggct cggaaggtct ctgaactcag aaggatggca ttttttgcaa gttaaagaaa    14040
atcaggatct gagttatttt gctaaacttg ggggaggagg aacaaataaa tggagtcttt    14100
attgtgtatc at                                                        14112

<210> SEQ ID NO 7
<211> LENGTH: 13993
<212> TYPE: DNA
<213> ORGANISM: H. sapiens

<400> SEQUENCE: 7
atggacccgc cgaggcccgc gctgctggcg ctgctggcgc tgcctgcgct gctgctgctg      60
ctgctggcgg gcgccagggc cgaagaggaa atgctggaaa atgtcagcct ggtctgtcca     120
aaagatgcga cccgattcaa gcacctccgg aagtacacat acaactatga ggctgagagt     180
tccagtggag tccctgggac tgctgattca agaagtgcca ccaggatcaa ctgcaaggtt     240
gagctggagg ttcccccagct ctgcagcttc atcctgaaga ccagccagtg caccctgaaa     300
gaggtgtatg cttcaaccc tgagggcaaa gccttgctga gaaaaccaa gaactctgag     360
gagtttgctg cagccatgtc caggtatgag ctcaagctgg ccattccaga agggaagcag     420
gttttccttt acccggagaa agatgaacct acttacatcc tgaacatcaa gaggggcatc     480
atttctgccc tcctggttcc cccagagaca gaagaagcca agcaagtgtt gtttctggat     540
accgtgtatg gaaactgctc cactcacttt accgtcaaga cgaggaaggg caatgtggca     600
acagaaatat ccactgaaag agacctgggg cagtgtgatc gcttcaagcc catccgcaca     660
ggcatcagcc cacttgctct catcaaaggc atgacccgcc ccttgtcaac tctgatcagc     720
agcagccagt cctgtcagta cactactggac gctaagagga agcatgtggc agaagccatc     780
tgcaaggagc aacacctctt cctgcctttc tcctacaaga taagtatgg gatggtagca     840
caagtgacac agactttgaa acttgaagac acaccaaaga tcaacagccg cttctttggt     900
gaaggtacta gaagatggg cctcgcattt gagagcacca atccacatc acctccaaag     960
caggccgaag ctgttttgaa gactctccag gaactgaaaa actaaccat ctctgagcaa    1020
aatatccaga gagctaatct cttcaataag ctggttactg agctgagagg cctcagtgat    1080
gaagcagtca catctctctt gccacagctg attgaggtgt ccagccccat cactttacaa    1140
gccttggttc agtgtggaca gcctcagtgc tccactcaca tcctccagtg gctgaaacgt    1200
gtgcatgcca acccccttct gatagatgtg gtcacctacc tggtggccct gatccccgag    1260
ccctcagcac agcagctgcg agagatcttc aacatggcga gggatcagcg cagccgagcc    1320
accttgtatg cgctgagcca cgcggtcaac aactatcata gacaaaaccc tacagggacc    1380
caggagctgc tggacattgc taattacctg atggaacaga ttcaagatga ctgcactggg    1440
gatgaagatt acacctattt gattctgcgg gtcattggaa atatgggcca aaccatggag    1500
cagttaactc cagaactcaa gtcttcaatc ctgaaatgtg tccaaagtac aaagccatca    1560
```

```
ctgatgatcc agaaagctgc catccaggct ctgcggaaaa tggagcctaa agacaaggac    1620
caggaggttc ttcttcagac tttccttgat gatgcttctc cgggagataa gcgactggct    1680
gcctatctta tgttgatgag gagtccttca caggcagata ttaacaaaat tgtccaaatt    1740
ctaccatggg aacagaatga gcaagtgaag aactttgtgg cttcccatat tgccaatatc    1800
ttgaactcag aagaattgga tatccaagat ctgaaaaagt tagtgaaaga agctctgaaa    1860
gaatctcaac ttccaactgt catggacttc agaaaattct ctcggaacta tcaactctac    1920
aaatctgttt ctcttccatc acttgaccca gcctcagcca aaatagaagg gaatcttata    1980
tttgatccaa ataactacct tcctaaagaa agcatgctga aaactaccct cactgccttt    2040
ggatttgctt cagctgacct catcgagatt ggcttggaag gaaaaggctt tgagccaaca    2100
ttggaggctc cttttgggaa gcaaggattt ttcccagaca gtgtcaacaa agctttgtac    2160
tgggttaatg gtcaagttcc tgatggtgtc tctaaggtct tagtggacca ctttggctat    2220
accaaagatg ataaacatga gcaggatatg gtaaatggaa taatgctcag tgttgagaag    2280
ctgattaaag atttgaaatc caagaagtc ccggaagcca gagcctaccc tccgcatcttg    2340 ggagaggagc ttggttttgc cagtctccat gacctccgac tcctgggaaa gctgcttctg    2400
atgggtgccc gcactctgca ggggatcccc cagatgattg gagaggtcat caggaagggc    2460
tcaaagaatg acttttttct tcactacatc ttcatggaga atgcctttga actccccact    2520
ggagctggat tacagttgca aatatcttca tctggagtca ttgctcccgg agccaaggct    2580
ggagtaaaac tggaagtagc caacatgcag gctgaactgg tggcaaaacc ctccgtgtct    2640
gtggagtttg tgacaaatat gggcatcatc attccggact tcgctaggag tggggtccag    2700
atgaacacca acttcttcca cgagtcgggt ctggaggctc atgttgccct aaaagctggg    2760
aagctgaagt ttatcattcc ttccccaaag agaccagtca agctgctcag tggaggcaac    2820
acattacatt tggtctctac caccaaaacg gaggtcatcc cacctctcat tgagaacagg    2880
cagtcctggt cagtttgcaa gcaagtcttt cctggcctga attactgcac ctcaggcgct    2940
tactccaacg ccagctccac agactccgcc tcctactatc cgctgaccgg ggacaccaga    3000
ttagagctgg aactgaggcc tacaggagag attgagcagt attctgtcag cgcaacctat    3060
gagctccaga gagaggacag agccttggtg gatacccctga agtttgtaac tcaagcagaa    3120
ggcgcgaagc agactgaggc taccatgaca ttcaaatata tcggcagag tatgaccttg    3180 tccagtgaag tccaaattcc ggattttgat gttgacctcg aacaatcct cagagttaat    3240 gatgaatcta ctgagggcaa aacgtcttac agactcaccc tggacattca gaacaagaaa    3300
attactgagg tcgccctcat gggccaccta agttgtgaca caaaggaaga aagaaaaatc    3360
aagggtgtta tttccatacc ccgtttgcaa gcagaagcca gaagtgagat cctcgcccac    3420
tggtcgcctg ccaaactgct tctccaaatg gactcatctg ctacagctta tggctccaca    3480
gtttccaaga gggtggcatg gcattatgat gaagagaaga ttgaatttga atggaacaca    3540
ggcaccaatg tagataccaa aaaaatgact tccaatttcc ctgtggatct ctccgattat    3600
cctaagagct tgcatatgta tgctaataga ctcctggatc acagagtccc tcaaacagac    3660
atgactttcc ggcacgtggg ttccaaatta atagttgcaa tgagctcatg gcttcagaag    3720
gcatctggga gtcttcctta tacccagact ttgcaagacc acctcaatag cctgaaggag    3780
ttcaacctcc agaacatggg attgccagac tcccacatcc cagaaaacct cttcttaaaa    3840
agcgatggcc gcgtcaaata taccttgaac aagaacagtt tgaaaattga gattcctttg    3900
ccttttggtg gcaaatcctc cagagatcta aagatgttag agactgttag gacaccagcc    3960
```

```
ctccacttca agtctgtggg attccatctg ccatctcgag agttccaagt ccctactttt    4020
accattccca agttgtatca actgcaagtg cctctcctgg gtgttctaga cctctccacg    4080
aatgtctaca gcaacttgta caactggtcc gcctcctaca gtggtggcaa caccagcaca    4140
gaccatttca gccttcgggc tcgttaccac atgaaggctg actctgtggt tgacctgctt    4200
tcctacaatg tgcaaggatc tggagaaaca acatatgacc acaagaatac gttcacacta    4260
tcatgtgatg ggtctctacg ccacaaattt ctagattcga atatcaaatt cagtcatgta    4320
gaaaaacttg gaaacaaccc agtctcaaaa ggtttactaa tattcgatgc atctagttcc    4380
tggggaccac agatgtctgc ttcagttcat ttggactcca aaaagaaaca gcatttgttt    4440
gtcaaagaag tcaagattga tgggcagttc agagtctctt cgttctatgc taaaggcaca    4500
tatggcctgt cttgtcagag ggatcctaac actggccggc tcaatggaga gtccaacctg    4560
aggtttaact cctcctacct ccaaggcacc aaccagataa caggaagata tgaagatgga    4620
accctctccc tcacctccac ctctgatctg caaagtggca tcattaaaaa tactgcttcc    4680
ctaaagtatg agaactacga gctgacttta aaatctgaca ccaatgggaa gtataagaac    4740
tttgccactt ctaacaagat ggatatgacc ttctctaagc aaaatgcact gctgcgttct    4800
gaatatcagg ctgattacga gtcattgagg ttcttcagcc tgctttctgg atcactaaat    4860
tcccatggtc ttgagttaaa tgctgacatc ttaggcactg acaaaattaa tagtggtgct    4920
cacaaggcga cactaaggat tggccaagat ggaatatcta ccagtgcaac gaccaacttg    4980
aagtgtagtc tcctggtgct ggagaatgag ctgaatgcag agcttggcct ctctggggca    5040
tctatgaaat taacaacaaa tggccgcttc agggaacaca atgcaaaatt cagtctggat    5100
gggaaagccg ccctcacaga gctatcactg ggaagtgctt atcaggccat gattctgggt    5160
gtcgacagca aaacattttt caacttcaag gtcagtcaag aaggacttaa gctctcaaat    5220
gacatgatgg gctcatatgc tgaaatgaaa tttgaccaca caaacagtct gaacattgca    5280
ggcttatcac tggacttctc ttcaaaactt gacaacattt acagctctga caagttttat    5340
aagcaaactg ttaatttaca gctacagccc tattctctgg taactacttt aaacagtgac    5400
ctgaaataca atgctctgga tctcaccaac aatgggaaac tacggctaga cccctgaag    5460 ctgcatgtgg ctggtaacct aaaaggagcc taccaaaata tgaaataaa acacatctat    5520 gccatctctt ctgctgcctt atcagcaagc tataaagcag acactgttgc taaggttcag    5580
ggtgtggagt ttagccatgg gctcaacaca gacatcgctg ggctggcttc agccattgac    5640
atgagcacaa actataattc agactcactg catttcagca atgtcttccg ttctgtaatg    5700
gccccgttta ccatgaccat cgatgcacat acaaatggca atgggaaact cgctctctgg    5760
ggagaacata ctgggcagct gtatagcaaa ttcctgttga agcagaaacc tctggcattt    5820
actttctctc atgattacaa aggctccaca agtcatcatc tcgtgtctag aaaagcatc     5880 agtgcagctc ttgaacacaa agtcagtgcc ctgcttactc cagctgagca gacaggcacc    5940
tggaaactca agacccaatt taacaacaat gaatacagcc aggacttgga tgcttacaac    6000
actaaagata aaattggcgt ggagcttact ggacgaactc tggctgacct aactctacta    6060
gactccccaa ttaaagtgcc acttttactc agtgagccca tcaatatcaa tgatgcttta    6120
gagatgagag atgccgttga gaagccccaa gaatttacaa ttgttgcttt tgtaaagtat    6180
gataaaaacc aagatgttca ctccattaac ctcccatttt ttgagacctt gcaagaatat    6240
tttgagagga atcgacaaac cattatagtt gtactggaaa acgtacagag aaacctgaag    6300
```

```
cacatcaata ttgatcaatt tgtaagaaaa tacagagcag ccctgggaaa actcccacag    6360
caagctaatg attatctgaa ttcattcaat tgggagagac aagtttcaca tgccaaggag    6420
aaactgactg ctctcacaaa aaagtataga attacagaaa atgatataca aattgcatta    6480
gatgatgcca aaatcaactt taatgaaaaa ctatctcaac tgcagacata tatgatacaa    6540
tttgatcagt atattaaaga tagttatgat ttacatgatt tgaaaatagc tattgctaat    6600
attattgatg aaatcattga aaattaaaa agtcttgatg agcactatca tacccgtgta    6660
aatttagtaa aaacaatcca tgatctacat ttgtttattg aaaatattga ttttaacaaa    6720
agtggaagta gtactgcatc ctggattcaa aatgtggata ctaagtacca aatcagaatc    6780
cagatacaag aaaaactgca gcagcttaag agacacatac agaatataga catccagcac    6840
ctagctggaa agttaaaaca acacattgag gctattgatg ttagagtgct tttagatcaa    6900
ttgggaacta caatttcatt tgaaagaata aatgatgttc ttgagcatgt caaacacttt    6960
gttataaatc ttattgggga ttttgaagta gctgagaaaa tcaatgcctt cagagccaaa    7020
gtccatgagt taatcgagag gtatgaagta gaccaacaaa tccaggtttt aatggataaa    7080
ttagtagagt tggcccacca atacaagttg aaggagacta ttcagaagct aagcaatgtc    7140
ctacaacaag ttaagataaa agattacttt gagaaattgg ttggatttat tgatgatgct    7200
gtcaagaagc ttaatgaatt atcttttaaa acattcattg aagatgttaa caaattcctt    7260
gacatgttga taaagaaatt aaagtcattt gattaccacc agtttgtaga tgaaaccaat    7320
gacaaaatcc gtgaggtgac tcagagactc aatggtgaaa ttcaggctct ggaactacca    7380
caaaaagctg aagcattaaa actgtttta gaggaaacca aggccacagt tgcagtgtat    7440
ctggaaagcc tacaggacac caaaataacc ttaatcatca attggttaca ggaggcttta    7500
agttcagcat ctttggctca catgaaggcc aaattccgag agactctaga agatacgaa    7560 gaccgaatgt atcaaatgga cattcagcag gaacttcaac gatacctgtc tctggtaggc    7620
caggtttata gcacacttgt cacctacatt tctgattggt ggactcttgc tgctaagaac    7680
cttactgact ttgcagagca atattctatc caagattggg ctaaacgtat gaaagcattg    7740
gtagagcaag ggttcactgt tcctgaaatc aagaccatcc ttgggaccat gcctgccttt    7800
gaagtcagtc ttcaggctct tcagaaagct accttccaga cacctgattt tatagtcccc    7860
ctaacagatt tgaggattcc atcagttcag ataaacttca aagacttaaa aaatataaaa    7920
atcccatcca ggttttccac accagaattt accatcctta acaccttcca cattccttcc    7980
tttacaattg actttgtaga aatgaaagta aagatcatca gaaccattga ccagatgctg    8040
aacagtgagc tgcagtggcc cgttccagat atatatctca gggatctgaa ggtggaggac    8100
attcctctag cgagaatcac cctgccagac ttccgtttac cagaaatcgc aattccagaa    8160
ttcataatcc caactctcaa ccttaatgat tttcaagttc ctgaccttca cataccagaa    8220
ttccagcttc cccacatctc acacacaatt gaagtaccta cttttggcaa gctatacagt    8280
attctgaaaa tccaatctcc tcttttcaca ttagatgcaa atgctgacat agggaatgga    8340
accacctcag caaacgaagc aggtatcgca gcttccatca ctgccaaagg agagtccaaa    8400
ttagaagttc tcaattttga ttttcaagca atgcacaac tctcaaaccc taagattaat    8460
ccgctggctc tgaaggagtc agtgaagttc tccagcaagt acctgagaac ggagcatggg    8520
agtgaaatgc tgttttttgg aaatgctatt gagggaaaat caaacacagt ggcaagttta    8580
cacacagaaa aaaatacact ggagcttagt aatggagtga ttgtcaagat aaacaatcag    8640 cttacccctgg atagcaacac taaatacttc cacaaattga acatccccaa actggacttc    8700
```

```
tctagtcagg ctgacctgcg caacgagatc aagacactgt tgaaagctgg ccacatagca    8760
tggacttctt ctggaaaagg gtcatggaaa tgggcctcgc ccagattctc agatgaggga    8820
acacatgaat cacaaattag tttcaccata gaaggacccc tcacttcctt tggactgtcc    8880
aataagatca atagcaaaca cctaagagta aaccaaaact tggtttatga atctggctcc    8940
ctcaactttt ctaaacttga aattcaatca caagtcgatt cccagcatgt gggccacagt    9000
gttctaactg ctaaaggcat ggcactgttt ggagaaggga aggcagagtt tactgggagg    9060
catgatgctc atttaaatgg aaaggttatt ggaactttga aaaattctct tttctttttca   9120 gcccagccat ttgagatcac ggcatccaca acaatgaag ggaatttgaa agttcgtttt     9180
ccattaaggt taacagggaa gatagacttc ctgaataact atgcactgtt tctgagtccc    9240
agtgcccagc aagcaagttg gcaagtaagt gctaggttca atcagtataa gtacaaccaa    9300
aatttctctg ctggaaacaa cgagaacatt atggaggccc atgtaggaat aaatggagaa    9360
gcaaatctgg atttcttaaa cattcccttta acaattcctg aaatgcgtct accttacaca    9420
ataatcacaa ctcctccact gaaagatttc tctctatggg aaaaaacagg cttgaaggaa    9480
ttcttgaaaa cgacaaagca atcatttgat ttaagtgtaa aagctcagta taagaaaaac    9540
aaacacaggc attccatcac aaatcctttg gctgtgcttt gtgagtttat cagtcagagc    9600
atcaaatcct ttgacaggca ttttgaaaaa aacagaaaca atgcattaga ttttgtcacc    9660
aaatcctata atgaaacaaa aattaagttt gataagtaca aagctgaaaa atctcacgac    9720
gagctcccca ggacctttca aattcctgga tacactgttc cagttgtcaa tgttgaagtg    9780
tctccattca ccatagagat gtcggcattc ggctatgtgt cccaaaagc agtcagcatg     9840 cctagtttct ccatcatagg ttctgacgtc cgtgtgcctt catacacatt aatcctgcca    9900
tcattagagc tgccagtcct tcatgtccct agaaatctca agctttctct tccagatttc    9960
aaggaattgt gtaccataag ccatattttt attcctgcca tggcaatat tacctatgat    10020 ttctccttta aatcaagtgt catcacactg aataccaatg ctgaacttttt taaccagtca   10080 gatattgttg ctcatctcct ttcttcatct tcatctgtca ttgatgcact gcagtacaaa    10140
ttagagggca ccacaagatt gacaagaaaa agggggattga agttagccac agctctgtct   10200
ctgagcaaca aatttgtgga gggtagtcat aacagtactg tgagcttaac cacgaaaaat    10260
atggaagtgt cagtggcaaa aaccacaaaa ccggaaattc aattttgag aatgaatttc     10320 aagcaagaac ttaatggaaa taccaagtca aaacctactg tctcttcctc catggaattt    10380
aagtatgatt tcaattcttc aatgctgtac tctaccgcta aaggagcagt tgaccacaag    10440
cttagcttgg aaagcctcac ctcttacttt tccattgagt catctaccaa aggagatgtc    10500
aagggttcgg ttctttctcg ggaatattca ggaactattg ctagtgaggc caacacttac    10560
ttgaattcca agagcacacg gtcttcagtg aagctgcagg gcacttccaa aattgatgat    10620
atctggaacc ttgaagtaaa agaaatttt gctggagaag ccacactcca acgcatatat     10680
tccctctggg agcacagtac gaaaaaccac ttacagctag agggcctctt tttcaccaac    10740
ggagaacata caagcaaagc caccctggaa ctctctccat ggcaaatgtc agctcttgtt    10800
caggtccatg caagtcagcc cagttccttc catgatttcc ctgaccttgg ccaggaagtg    10860
gccctgaatg ctaacactaa gaaccagaag atcagatgga aaaatgaagt ccggattcat    10920
tctgggtctt tccagagcca ggtcgagctt tccaatgacc aagaaaaggc acaccttgac    10980
attgcaggat ccttagaagg acacctaagg ttcctcaaaa atatcatcct accagtctat    11040
```

```
gacaagagct tatgggattt cctaaagctg gatgtcacca ccagcattgg taggagacag   11100
catcttcgtg tttcaactgc ctttgtgtac accaaaaacc ccaatggcta ttcattctcc   11160
atccctgtaa aagttttggc tgataaattc attattcctg ggctgaaact aaatgatcta   11220
aattcagttc ttgtcatgcc tacgttccat gtcccattta cagatcttca ggttccatcg   11280
tgcaaacttg acttcagaga aatacaaatc tataagaagc tgagaacttc atcatttgcc   11340
ctcaccctac caacactccc cgaggtaaaa ttccctgaag ttgatgtgtt aacaaaatat   11400
tctcaaccag aagactcctt gattcccttt tttgagataa ccgtgcctga atctcagtta   11460
actgtgtccc agttcacgct tccaaaaagt gtttcagatg gcattgctgc tttggatcta   11520
aatgcagtag ccaacaagat cgcagacttt gagttgccca ccatcatcgt gcctgagcag   11580
accattgaga ttccctccat taagttctct gtacctgctg gaattgtcat tccttccttt   11640
caagcactga ctgcacgctt tgaggtagac tctcccgtgt ataatgccac ttggagtgcc   11700
agtttgaaaa acaaagcaga ttatgttgaa acagtcctgg attccacatg cagctcaacc   11760
gtacagttcc tagaatatga actaaatgtt ttgggaacac acaaaatcga agatggtacg   11820
ttagcctcta agactaaagg aacacttgca caccgtgact tcagtgcaga atatgaagaa   11880
gatggcaaat atgaaggact tcaggaatgg aaggaaaaa cgcacctcaa tatcaaaagc   11940
ccagcgttca ccgatctcca tctgcgctac cagaaagaca agaaaggcat ctccacctca   12000
gcagcctccc cagccgtagg caccgtgggc atggatatgg atgaagatga cgactttct   12060 aaatggaact tctactacag ccctcagtcc tctccagata aaaaactcac catattcaaa   12120
actgagttga gggtccggga atctgatgag gaaaactcaga tcaaagttaa ttgggaagaa   12180
gaggcagctt ctggcttgct aacctctctg aaagacaacg tgcccaaggc cacaggggtc   12240
ctttatgatt atgtcaacaa gtaccactgg gaacacacag gctcaccct gagagaagtg   12300 tcttcaaagc tgagaagaaa tctgcagaac aatgctgagt gggtttatca agggccatt   12360 aggcaaattg atgatatcga cgtgaggttc cagaaagcag ccagtggcac cactgggacc   12420
taccaagagt ggaaggacaa ggcccagaat ctgtaccagg aactgttgac tcaggaaggc   12480
caagccagtt ccagggact caaggataac gtgtttgatg gcttggtacg agttactcaa   12540
aaattccata tgaaagtcaa gaagctgatt gactcactca ttgattttct gaacttcccc   12600
agattccagt ttccggggaa acctgggata tacactaggg aggaactttg cactatgttc   12660
atgagggagg tagggacggt actgtcccag gtatattcga aagtccataa tggttcagaa   12720
atactgtttt cctatttcca agacctagtg attacacttc ctttcgagtt aaggaaacat   12780
aaactaatag atgtaatctc gatgtatagg gaactgttga agatttatc aaaagaagcc   12840 caagaggtat ttaaagccat tcagtctctc aagaccacag aggtgctacg taatcttcag   12900
gaccttttac aattcatttt ccaactaata gaagataaca ttaaacagct gaaagagatg   12960
aaatttactt atcttattaa ttatatccaa gatgagatca acacaatctt caatgattat   13020
atcccatatg tttttaaatt gttgaaagaa acctatgcc ttaatcttca taagttcaat   13080
gaatttattc aaaacgagct tcaggaagct tctcaagagt tacagcagat ccatcaatac   13140 attatgccc ttcgtgaaga atattttgat ccaagtatag ttggctggac agtgaaatat   13200
tatgaacttg aagaaaagat agtcagtctg atcaagaacc tgttagttgc tcttaaggac   13260
ttccattctg aatatattgt cagtgcctct aactttactt cccaactctc aagtcaagtt   13320
gagcaatttc tgcacagaaa tattcaggaa tatcttagca tccttaccga tccagatgga   13380
aaagggaaag agaagattgc agagctttct gccactgctc aggaaataat taaaagccag   13440
```

```
gccattgcga cgaagaaaat aatttctgat taccaccagc agtttagata taaactgcaa    13500 gattttcag accaactctc tgattactat gaaaaattta ttgctgaatc caaaagattg     13560
attgacctgt ccattcaaaa ctaccacaca tttctgatat acatcacgga gttactgaaa    13620
aagctgcaat caaccacagt catgaacccc tacatgaagc ttgctccagg agaacttact    13680
atcatcctct aattttttta aaagaaatct tcatttattc ttcttttcca attgaacttt    13740
cacatagcac agaaaaaatt caaactgcct atattgataa aaccatacag tgagccagcc    13800
ttgcagtagg cagtagacta taagcagaag cacatatgaa ctggacctgc accaaagctg    13860 gcaccaggc tcggaaggtc tctgaactca aaggatggc attttttgca agttaaagaa     13920
aatcaggatc tgagttattt tgctaaactt gggggaggag gaacaaataa atggagtctt    13980
tattgtgtat cat                                                      13993
```

<210> SEQ ID NO 8
<211> LENGTH: 43445
<212> TYPE: DNA
<213> ORGANISM: H. sapiens

<400> SEQUENCE: 8

```
accaagacag cgctcaggac tggttctcct cgtggctccc aattcagtcc aggagaagca      60
gagattttgt ccccatggtg ggtcatctga agaaggcacc cctggtcagg gcaggcttct     120
cagaccctga ggcgctggcc atggcccac tgagacacag gaagggccgc gccagagcac     180
tgaagacgct tggggaaggg aacccacctg ggacccagcc cctggtggct gcggctgcat     240
cccaggtggg ccccctcccc gaggctcttc aaggctcaaa gagaagccag tgtagaaaag     300
caaacaggtc aggcccggga ggcgcccttt ggacctttg caatcctggc gctcttgcag     360
cctgggcttc ctataaatgg ggtgcgggcg ccggccgcgc attcccaccg ggacctgcgg     420
ggctgagtgc ccttctcggt tgctgccgct gaggagcccg cccagccagc cagggccgcg     480
aggccgaggc caggccgcag cccaggagcc gccccaccgc agctggcgat ggacccgccg     540
aggcccgcgc tgctggcgct gctggcgctg cctgcgctgc tgctgctgct gctggcgggc     600
gccagggccg gtgagtgcgc ggccgctctg cgggcgcaga gggagcggga gggagccggc     660
ggcacgaggt tggccggggc agcctgggcc taggccagag ggagggcagc cacagggtcc     720
agggcgagtg gggggattgg accagctggc ggccctgca ggctcaggat ggggggcgcg      780
ggatggaggg gctgaggagg gggtctccgg agcctgcctc cctcctgaaa ggtgaaacct     840
gtgccggtgg tcccctgtc gggccctagc acccgctggg aagacgtggg aagctcacag     900
atttctttct cctgtcttac agaagaggaa atgctggaaa atgtcagcct ggtctgtcca     960
agtaaggcat ctgcgcatgg ggcgtggaag ggcgcccagc ccgtgcact ctcctacacc     1020 cgggtccctg agggcctccc actctacagg gctgagatgg catcgtggtg tgccttgctc    1080
tgaccccagg aagcaagttc cctgagcctc tgcccacacc caaggatgc caactctctt     1140 ctacctggcc ttctgttctg tcccaaaagt tcagcctggg ggcgggggag ggaagggatt    1200
gtctctccgc tggcctgtgc acactttgaa gaaacatcac tgtcctgttt atcagtgact    1260
agtcattgat tcgaagcatg tgagggtgag gaaatactga ctttaacctt tgtgaagaaa    1320
tcgaacctcc accccttcc tatttacctg acccctgggg gttaaaggaa ctggcctcca    1380
agcgcgaccc tgtgtgctgg agccgcgggg cggacttctg atgggcagc accgccatct    1440 agtggccgtc tgtcatcact gcagctggac tcaggaccca gatgttcttt ttcttcaatt    1500
```

```
gttcagaaaa ttcctctcaa ctacagtgga aacctccaga aattcttttc taggagtttg    1560
ttaagttagt tacgcttaat gcttaatgaa ctttgcctta agtatttggt agtcttagag    1620
tcacggaatt acggcgtgtt caagctaaaa aagcattaga gatagtacta tttgcgtaat    1680
gttgtcatct cttaatttgc cagagggtct ctcatgcaga ttttctgagc cccattactt    1740
gacacttgtc actcccttcc ctgtgcctca gatgagatat tcaagacatg ccagccaatt    1800
taaacattag cctcagcaaa acataatgg agaagtcaaa tctataaagg aaaattaagt     1860
ataaagtcaa ttaaaaaata atttgagttg aattaccatt tttaattctc tatgccactg    1920
cccctctctg cccagaattg gctgtccttg ggagagctat ttctgctatg tggctgacgt    1980
atttctcccc acgttagaag atgcgacccg attcaagcac ctccggaagt acacatacaa    2040
ctatgaggct gagagttcca gtggagtccc tgggactgct gattcaagaa gtgccaccag    2100
gatcaactgc aaggtatgga ggatgcaggc aggagggacc tagagcccac agctttcccc    2160
cagccctgtt ccagcgggcg cccaacacgc gaccttcccg gagggtgtgt actgagcaaa    2220
cgcagaacat cccagaactg ttgtaatctg atcaaagcac tgggactttg cctctgtttg    2280
taagtcagcc acattgctga gatgtggtct gcccccacca aatttcgcaa gtcagaagta    2340
ttttcccgtt aacttcccag atgcaatagg aatccatgat ctagattagc agcagtgtgg    2400
gtctgtagat ttcagcgtga gagaggccca gtaggtgagc tatgggaggc aggcaactcg    2460
gaatcgcact gtgaaatgca gttttttataa tttaagtcaa acagaatctg ttgctgaaaa    2520
atgaatggaa agaagaaaaa aatataaaca tacagtttgt tctaaaataa aactttgctt    2580
attattgaga ctggttgtac tcatgttaca tacatgtgga gcagatctac aggctgctat    2640
tggggtttgg gtggggaaga gaagtcaagc tgagcagtca cctttttta gagagtaccg     2700 tagctcttgt atgtgctgtc caatatggta gacatgagcc acattgggct atttaaatgg    2760
aatgaaatta aaaattcata ttcgttgtca cattagctgc atttcaactg ctcaacagcc    2820
accctggcta ctggctccca tattgaacag cacacatgta caacatttct ataaagttat    2880
ttgaatagtg ctggataata agtaggaatc cgttgaaact ccagctatat gcaaagctct    2940
aaataggccc taatagatat aaccagtttt tgggtgaca ttaaggagac atttgctgtg     3000
gaaacgaagg atggccctct tcctgctttc tgttttctt cttcactttc actcctagtc     3060
tgcagcgctt ctatttaacc acagctcttt ataattaaag tgagtaactt tagaaccaat    3120
aaaaggacat cctccttccc atgcctaggg gcaaacttaa gaaatgtgtt acccgggagg    3180
gggaaaacgt cagcaatagg actaagtcta ggttggtgca cagagaaccc aggaggcatg    3240
ttgataaggc atgtggtgtt gaggcgcagg cagtggtgtt cccagcacca ttcccttttgg   3300 tgctctgatt agagattaag ccctgggctt caggggccac ctctcattct tgatagacaa    3360
cctcaatgct ctgctaccct gaattctcag gttgagctgg aggttcccca gctctgcagc    3420
ttcatcctga agaccagcca gtgcaccctg aaagaggtgt atggcttcaa ccctgagggc    3480
aaagccttgc tgaagaaaac caagaactct gaggagtttg ctgcagccat gtccaggtaa    3540
gtcatgttgt acatgagcac acgcatgtgt gtgtgtccgc tgaggtatga acttgtgtgt    3600
ttgcaccagg cacggatgtg actgtaagta tttgtattcc gtatccatcg tggatcaggg    3660
aattactgag ttttcacaat catcaaaaag agagaagcat tagttaacct tccctagtta    3720
ggttccttta attatcattt tcatgtgttt ctaaaaatct catgctttaa acttcttgag    3780
attataaaac tgagatgctt tgtttaaaca agtgaattct tatttaaaga actagtcaag    3840
actagtgctt ggtggtcttt ggtgtggggt cccagaggca ctggctgctg tggccggcac    3900
```

```
atggcgggc agggtctgtt caccgcaggg cagaggagca ccaaggcttc ggtggctccc      3960
cctcctaggc tggcattcag ccactgcacg ctgatcggcc actgcagctg catctctgct      4020
gactggtcag ggcccatgtc gcacccattg taaatatttt caacatcacc cctgcctcat      4080
cctcaatcac agtttgtagg gtcctaggtg tgtatgaata caggcaggat agagttgtta      4140
acttggtagc atcagaaaac tctgtctgta ttagtctgtt ttcatgctgc tgataaagac      4200
atacctgaga ctgggcaatt tacaaaagaa aggtttattg gactcacagt tccacgtggc      4260
tggggaggtc tcacaatcat ggcggaaggt gagggacagc aagtcacatc ttatgtagat      4320
ggtggctgga aagagagct tgtgcagaga aactcctgtt tttagaacca tcagatctcc      4380
cgacacccat ctgcaatcac gagaacagca cgggaaagac ctgcccccat gattcaatca      4440
cctcccccg gtccctccc acaacacgtg gaattatga gagctacgag acgaaatttg      4500
ggtggggacg cagagccaaa ccatatcacc atccttgccc attttcagt tttgctaaac      4560
attagattca gatgccagtc ctttcttgcc aaaataggct gtgaggcttc tttctttcct      4620
atgctttatt ttctccaaga cttaactgta tatgagggag aggggtatgg tggcaggagg      4680
aaagagtggt ttattttttg gtccttggtc ttctccaaat acagaagaga ctcctgttct      4740
tgaaaggag ggctttccat gtttgcatct tcatgacttt aactgtcttt tttaaaaatt      4800
gacatacaat aattatacat atttattgag aacatagtga tattttgata catgtaatgt      4860
atggtgatca gatcagagta attagcatac ccatcatctc aaacatttat catttcttcg      4920
tgttgggaac tttctgagag agtgtaggct gtgggagata agtccgtcac cttttcctcc      4980
tgatgtaacc agagtggctg cagccaggtc ctcagaaact cagagagtac ccagtgggaa      5040
atccctaaga ccaaagtcag catgggcttc agccatggcc tgacaccata caaaagaatg      5100
actgtccaac aagtgtatga aaataagctc caattcactg gtagtcaaga aatgcgaatt      5160
aatgtaacaa caagatattt atctgctttt acccatcata ctgcaaaact ggaaaacagt      5220
gatagcacct gttgctggca ggccagtgag gaaaagtgtg ctgtcctgag ctgctggtgg      5280
aaacagagc catcaggcaa tatctactgt aatttaaaat acttaatacc ctttgacaca      5340
gatatttag tctttgggac tctagcccat gaaaataaaa gcagtaatgt gtgaagatag      5400
gcacataagg atgtttgttt tggtattgtt tgtgtggttt aaaaaaaatc cagaaagaga      5460
gagggcaaat gccatcaaat ggggcaatgt gtgaataaat tatatttagc catggaatgg      5520
aatgttctgc atgcagcttt taaaaaaatc tgttagagct gtaccaagtg actcagaagg      5580
attttttgtga agtataatta agtgagaaaa acaagataaa agtatgcata atacaatgcc      5640
acttgtataa aacaaacaat ggcaaaatct ttgtatgact ctgtttgcac tcacccatgt      5700
ttacagagga ttgtatgagt gtgcagaaac aaatggaaca accactcggg tgtccgtatg      5760
gggaggatgg gcaaagagac tgatatgggt ggagaacaga gcagggctgg atgagccaag      5820
caaaaaagt taaacacag ctggacctgg tggctcatgc ctgtagtccc agcactttgg      5880
gaggccgagg agggagaatc acctgaggtc aggagtttga gaccagcctg gccaacatgg      5940
tgaaaactgt ctctactaaa aatacaaaaa ttagctgggt gtgatggcac atgccagtag      6000
tcctagctac tccggaggct gaggcaggag aatcacttga tcccaggagg tggaggttgc      6060
agtgagctga ggttgcgcca ttgcactcca gcccgggcga ccgagcgaga ctccatttca      6120
aaaaagaaa aagaaaaaag aaaaaaagaa aaaaaagaa tcaccaaaac ttatgtatat      6180
gtgcatactt ttttgaaaat gtatgtctat gtgtagctat attctatatt tacaaataaa      6240
```

```
tgatgtcaga agaacaattg gttaaaaaaa tatgagaaaa gaaacttcag tgccacccag    6300
cttacttcca gcaagttgta atggagaagg acatttccgt gaccatcctc tctctgggac    6360
aggtatgagc tcaagctggc cattccagaa gggaagcagg ttttccttta cccggagaaa    6420
gatgaaccta cttacatcct gaacatcaag aggggcatca tttctgccct cctggttccc    6480
ccagagacag aagaagccaa gcaagtgttg tttctggtga ggatttagaa agctgatagc    6540
agtggccctt gaaactcatc ttcatgtgtt agagaccagt cctaccatat acaaagcaga    6600
tcactgagtc agctccatga ctagttacat aggaagccct ggattggcgt gaaatactgg    6660
tgcccgaggt tcctcctgcc ccttaggctc actgacagat catcccaagc aggcttatca    6720
ggttgggtct aattttaaaa cagtcattga ggagtcctgg ccaccccacc cctgcttttg    6780
tttgatgctt cacctgtgtt tgctgggtta tggtgtacac agtaaatcct gtgtgtattt    6840
taaacaccaa aaataatggg atctgttgct ggtctctttt acgaatttca ggtttcactg    6900
tgagacagaa ttcatttcac ctcagtccca tgagcacttt tgtgtgttct aatttctcta    6960
cgacaccata atgggagaag acaccgatgc aacctgcgga ggccttcctg cagacccacc    7020
tttaactggt tttctctctc ccaacttggg ctggccaggc actagcaaga ccacactctg    7080
cataggaaga aaagaaagt ccctcccaaa gctagattcc ttctgctttt tctttcacga    7140
tccccacccc atccctccca agtacccaag gatgttgccc gtgttgaata catgtggttg    7200
catcttcttc ctccatagga taccgtgtat ggaaactgct ccactcactt taccgtcaag    7260
acgaggaagg gcaatgtggc aacagaaata tccactgaaa gagacctggg gcagtgtgat    7320
cgcttcaagc ccatccgcac aggcatcagc ccacttgctc tcatcaaagg catggtaagt    7380
cccatgtcag cactgtcgtg cacagcaagg agcatcctct tattaataca attccagaac    7440
ttttgagcta gtgggcacct ttgaggacag cctgccctgg ctgttttta tacagactag    7500
agataggacc ctgagcaggc acgggaaggt ctgcccaggc ttcacggcct gggatcagtt    7560
gagccaaggc ttgagtcagg ctcctccctc ccagcccaga gctctgtctt tcctcctgtc    7620
cttctgtcac tggcaccaaa ctgcctctaa tctcatcact tgagagtaat gactactcac    7680
ctctgagaag gttccgggga tggatgtagg gcagcaaaac caccttctgt tcttttctgc    7740
acaaggactc cttgtgccag ctccaagcct ctggcctttg aagaagtccc aagacctgtg    7800
ttctcccct ctccctcatc ccatgaagtg gagtgactta gagtgctcca gcttcttgtc    7860
cttccacccc cagtaccacc ctgaccaaac atggcccac tgccaccggc ctggagcacc    7920
ctctcctctc tgttaactgg ggccatggag caccatatta cctgagcctg cctgacccct    7980
gcaacatctt ccctgatatg agcccagcc tgtctcagtg aacatgaata acttgggcaa    8040
tcactgtcat gctgggcgct gttcctggtc attgtcctta gggttgaaaa cagggagtct    8100
gatgaccatg agtgccacag tcagaagagg ataatgcact ggcttagggg tcttttctga    8160
gcatctgctg tttgctcaac cccactctgg gcagcaccaa ggaagggaca gtggcagatg    8220
aaccatggac cttcccctca ggatgcttcc agtctaatgc aggagccagg tcaataaagt    8280
atacgtggta tactcaataa ggtgataagc tgaacagtgc agacaagaag tcctgggcct    8340
gaccaggaag gagaaagaat tattcatgta gctcagcggg caacatttca tggaagatgt    8400
ggagcaggaa cccaaaaaat gcaaagaata tgtaaatgaa agagacatgt aagaatgggc    8460
ttttgggcaa agaaaagtta ctgagcaggt gtgtgagggg ctatgtggtg ggatgggcat    8520
gtggaggata caaagtttag acattgtcca gtgagggtga aaaagagga gtctacagct    8580
tgactcagct ttggggatgc cgacttgttg caccccctgg tctaaatgtc aagtacccag    8640
```

```
ttatcttctt tctctgagtt tatctagtgg tacaggactc ctgctcccct ctaccttgaa    8700
ggtaaatgct tttaacagaa gatacaggga ctgatcaaaa tgctcgtctc caatctcttt    8760
catagacccg ccccttgtca actctgatca gcagcagcca gtcctgtcag tacacactgg    8820
acgctaagag gaagcatgtg gcagaagcca tctgcaagga gcaacacctc ttcctgcctt    8880
tctcctacaa gtaggtcatg tgatgcaccc ctgatttgtc atttaatggg tcagtgtgaa    8940
ctgaacactt ctcaagtgct ctgttccagg caaacctgtg cctgggaggg aggaatggag    9000
agggataaaa tgccgcccct ccctgtcccc cttttaagc gaacaggcca tttggcagaa    9060
aagtcctagg catgcaaaac aatccaagac caacaaaaga tatctaagac ccattcttta    9120
agggctgtag atccagaaaa cctgaggatc actgcagggt accctggtta gaaaaggttt    9180 catgaagat ttgggatact gactggaaac ttgtgtatcc aaatccactt tgaaaactga    9240
taatcaatga atatatattg agtaactgcc atattcttgg ctctatgttg tggaagatac    9300
gaaagaattt tgagacattg cactagttcc tacctctggc cactccagac tagtggagag    9360
tataaggcac gcatgtcttt ttgatgggag gataactagc gtgaccagga agaggtggat    9420
gttattcatt cagggccaac aatggctgga tttacccatg ctttgaaaga tgggcaggac    9480
ttgggtagat gcagagacag ggaaaaacctt caacatggaa agaatagtat gttctggcca    9540
tccgtgacat ggtgtgcttc cttggttacc aggaataagt atgggatggt agcacaagtg    9600
acacagactt tgaaacttga agacacacca aagatcaaca gccgcttctt tggtgaaggt    9660
aagagtttct gtccacatag ttgctggaaa atctactcaa gatgtgccta tcatggctta    9720
gccacttgct gagccctgtt aaatgtctgc tgactaacaa gtgatacaga cactggtgtt    9780
ctggctacct ctagtgagaa agcaaactca tttcatgatg tcaagttgca atggcataaa    9840
ggaaaagaag ttcccaaagc tacttaggca tttgtaaata gaaaactgga atcctaagtt    9900
taacatgaca tatttgatag aactgacatc acccatcctg tgataagatc cagagctgtc    9960
ccagacgagg tggaccaagt gggagagaac cttcagagtc tggccagata gtaacctcag   10020
gagtcagtct ttagaggtag aaggaactct aacaatctca agtccaaccc ttacccagta   10080
ttgtattgta tttatatctg tccaaattcc ttcttgtaca ttacctcatt gtccttttg    10140 ctcatagcaa cctgtgatgt caggtggtag agatgtgatt ttatacctat tctacagagg   10200
agacagtgac acagagaggc ttagagtttg atgtagtcaa ggccgcagaa tattagaggg   10260
gggaaaataa gtgccaggtt gtaatctaag ccaggactat tctcattaca ccacatttcc   10320
atgatgactt ttacctctct tcctggcata ggtcacagta ggtggtggag aggatacaaa   10380
agtgtctccc ctccccacaa gctgctggta gacccaatta aagaaatgg tgataagcac    10440 ccatgtgcct ggtcccagtt gtaaccatgt caacagtagc acctcctcac caattatttc   10500
aagctaaggg taacctgatg atagactcag acaagtctgg attccacttt agctctacct   10560
cttagaccct gagagctctt gggaaaccta agttgctcat ctctgggtca cacttcctca   10620
tctctgggtc tcatctcttt gtctcatctc tgggactcag agctgagatc cagggatgag   10680
caatttacat ggcccaaaaa ctctgtgggt ctcagaagca gggctgaatt tatcattaaa   10740
ttgaacaata atgccacccc acagggatag gatgatgagt cagtgaaaac aagtcaatca   10800
cctatggcag agccagatct agcaggcatt gaatacagga tagtttcttt ccctttttcc   10860
ctgtgctgat actccacaat ttccagcttc cagtagacaa agatatggtt gagatgaaga   10920
aagctagagt tcctttgaca ctttccatct tccaggtact aagaagatgg gcctcgcatt   10980
```

-continued

```
tgagagcacc aaatccacat cacctccaaa gcaggccgaa gctgttttga agactctcca    11040
ggaactgaaa aaactaacca tctctgagca aaatatccag agagctaatc tcttcaataa    11100
gctggttact gagctgagag gcctcagtga tgaagcagtc acatctctct tgccacagct    11160
gattgaggtg tccaggtatc taatggttac agctcaactt tttataaaac tgatggtaac    11220
tgactgaact ttcaaacctt ggccaaatgg agaatctcag ggaccatttg gatatcaatc    11280
cagttaatca attagtcaat cagttcatga ttgctggata gagaactatc agctgctgcg    11340
ctgagttcca tgaaacacac acgcgcatac tgtgttcaag gcagctatgt atttgtgtgt    11400
taaaacagaa ggagaatagt tcccacattt tgatgggtaa cttttaattc ctaggtctat    11460
tgcaggtgct ctccagaagc ttataggctg gtggagagag aactcagacg aaaaatataa    11520
tatgatttct ctaccttca aggcactggc tttaagtgct atgaaggtga gagaagggac    11580
tgaggccagg aatgagaccc agctaatgtt ggccaggcat attctgtgtg ctggccaaag    11640
gactgtgata acagtcttct tgttgctaca gatccacagt cccctcttgg aacttttctc    11700
gattgggctt cttctgtggg taatattcct aaggaaagca tcatggttct gagctccaag    11760
ttgggttttg aagttagatt tgaatagtga atgaggtgat taagggctct cctggcagag    11820
gacacaccat gagcaatatt ttatgtgccc tgaaggtggt ctgtataact ttatccatgt    11880
ctttcttctc agccccatca ctttacaagc cttggttcag tgtggacagc ctcagtgctc    11940
cactcacatc ctccagtggc tgaaacgtgt gcatgccaac cccctctga tagatgtggt    12000 cacctacctg gtggccctga tccccgagcc ctcagcacag cagctgcgag agatcttcaa    12060
catggcgagg gatcagcgca gccgagccac cttgtatgcg ctgagccacg cggtcaacaa    12120
gtgagtttcc acactgtatt tctcctccta ggagcagagg aacatcttgc acctctgtgc    12180
atctctgtat taaaactgaa cccctccttc cactttcaaa ctctgctcct tactcttgtg    12240
ttttttcttg atcatttttg gggtaatgac ttgaaataag aaatcagcaa acacaaattg    12300 aattttaaa aatattttct ctacattata ttataaaagt ttttgaacat agcaaagttg    12360
acagaatttc acagggaaaa cccctagaaa accagctatc tcctactatt aagtgttat    12420 tatatttgct ttatcacata tacatccatc cattaattca tcttatttc tgaagcattt    12480 caaagtaaat tgcaaacatc aacacacttt cccctaagta ttacagcttg catattatta    12540
acttcagttc aatattagtt agcagttttt tcctctgaat ttttttgttt gtttgttttg    12600 ttttttttg ttgttgttgt tttttgaga tggtctcact gtgtcaccca ggctggagtg    12660
cagtgatgca gtcacggctc actgaagcct caaattcctg ggctgaagtg atcctcccac    12720
ctcagcctcc tgagtagctg ggaccacagg tgcatgctac catgccctgg ctaattttg    12780 tattcttggt agatacaggg tttcaccatg ttgctcaggc tagcaggttt ttcctttgat    12840 gaaattttt ggcttttct tttttacatt tttatataaa tttatgtgga acaagtgtaa    12900
ttttgttaca tgaatagatt gtgcagtagt taagtcaggg ctttcagggt atccatcacc    12960
cagacaacat atagtgtacc cactaagtaa tttctcacca tccatctccc tccacttcca    13020
caccttctga gtctcaattg tctatcattc cacacactat gtccttgtgt gcacattatt    13080
tcactcccac ttataaatga caacacgcaa tatttgtctt tctgtgactg tcctgtttca    13140
cttaagacaa tgacctccag ttccatccat gttgctgcaa atgacatgat tttattcttt    13200
ttatggccga atagtatttt attgcctata catttcacat ttttaatcca atcgtccatt    13260
gatagacact taggttgatt ccatgtcttt gctattgtga atagtgctgt gataaacata    13320
tgggtgcagg tttcctttgg atataatgat ttctttcct ttaggtatat acccagtaat    13380
```

```
gggattgttg gatttattgg tagttctatt tttagttctt tgagaaatct ctgtattgtt   13440
ttccatagtg gttgtactta tttacaatcc catcaacagt gattaactgt ttccttttct   13500
ctgtatcctc accaacaact gttattttt gtcttttgaa taatggccct cctgactctt    13560
gtaagatgtt atctcattgt ggttttaatt tacatttctc taatgattag taatgttatg   13620
cattttttca tatgcctatt gccatttgta tgtcttcttt tgaaaaaat gtctattcat    13680 gtcctttgcc tacttttta tgggattatt tggggattt ttttgttgag ttgtttgaat     13740
tgcttgtaca ttccggatat tagtaccca ttggatgaat agtttgcaaa tattttctcc    13800
cattctgcag gttacccccc tgttgattat ttgttttact gtgcagaaac tttttacttt   13860
aattaagttc tatttgtcta ttttttgttt ttgttgtctt tgcctttgag gtcttattca   13920
cgaattcttt gtctaggcca atgtccagag aagtttccc taggttttct tcttgcattt    13980
ttatagtctc aggtcttata tttaagtctt tgatccatct tgagttgatt tttttatatg   14040
gtgacagata ggagtccagt tttattcttc tgcatatggc aatccatctt tcccagcacc   14100
acttattgaa aagggtgtcc tttccctagt gtatgtttt gtcaattttg tcaaagatcc    14160
gttgactgta agtatgtgac tttatttctg ggttcagtat tctgttccat tgatctatgt   14220
gtctattttt atgccagtac catgctgttt agattactat agccttgttg tataatctga   14280
agtcaggtaa tgtgatgcct ccagctatgt tcttttgct taaaattgct tcagctattc    14340
aggctctttt tggattccat atgaatttta taattatttt ttctaattca caagtttggg   14400
ttttaagaca aacctaactg gggttaccaa gtcctgactc tcttctctta ttctgtagct   14460
atcataagac aaaccctaca gggacccagg agctgctgga cattgctaat tacctgatgg   14520
aacagattca agatgactgc actggggatg aagattacac ctatttgatt ctgcgggtaa   14580
tctcagtctt ttatatgaca tacatcattt cagaagcact tttcctggac acctttact    14640 tccctctcct gcaccctgat gggttcttgt ttctttttctt caatgcaggt cattggaaat   14700
atgggccaaa ccatggagca gttaactcca gaactcaagt cttcaatcct gaaatgtgtc   14760
caaagtacaa agccatcact gatgatccag aaagctgcca tccaggctct gcggaaaatg   14820
gagcctaaag acaaggtaaa gtccacaaga agaggtctga aagtgaaagt ttattaacaa   14880
ggatttggaa ggtactaggg gaatgagact ctagatttca tctactgact ttattctgct   14940
gtttctttcc tttccttcct tccttccttc cttccttcct ccctccctcc ctttcttctt   15000
tccttccttc cttccttctt tcgagatgga atctcactct attgcccagg ctggagtgca   15060
gtggcatgat ctcggctcac tgcaacttct gcctcctggg ttcaagcaat tctctctgcc   15120
tcagcctcct gagtaactgg gattacaggc atgtgccatt acacccagct aattttgta    15180 tttttagta gagatggagt tttgccatgt tggccaggct ggtcttgagc tcctgacctc    15240
aggtgatccg cctgcctcag ccttgcaaag tgctgggatt acaggcgtga gccactgcac   15300
ctggcctcta ctgttttcta attgcaaatt tcaacaagcc tattgacttg actgcctagc   15360
agtatgtgac gtgagagaaa tacttgactt tgctgctatg tcaacatgca gaacgtgaga   15420
tgtttttgct tcctaccgtc cacctaccag attgaccatc cctctcatca tggaaaaaca   15480
tgcttaattt tcccccaata agcttaggct aggatagcca acttggcccc ctcttaggtg   15540
caaagactcc agaactttgg aaactaccct atttattagc cccaaactct tactacccct   15600
tctcatcttt atcctcacat taaaataact tacgttaaaa caacttgatt ttcacttagt   15660
ggtggatctc caaacaaatc acaacttggc cataatttat gtgttttaat ggaattgaat   15720
```

```
tcaacaggca ttccacaggc ttttctgggg aacccttact tgatagtgct ctaggaaaca   15780
ctggcaagaa gattcaatac cagcatttga agaacgatta cagagaaatt agacctgtgc   15840
ttaagaaaga gctagcagac aatgccagtg tttgccaggc atgttctgtg ttctgaccac   15900
aggacagtga taaccatctc ctcttttgac tgcaggacca ggaggttctt cttcagactt   15960
tccttgatga tgcttctccg ggagataagc gactggctgc ctatcttatg ttgatgagga   16020
gtccttcaca ggcagatatt aacaaaattg tccaaattct accatgggaa cagaatgagc   16080
aagtgaagaa ctttgtggct tcccatattg ccaatatctt gaactcagaa gaattggata   16140
tccaagagta agtaagagct attcacccca tataccactg agggccctga gctggaattc   16200
caaccctagg ttttggcata gccactgtct gcccttgctt ctgaaacaaa cacttgtgca   16260
aatgtgtagc agatctagac ccaaagactt agggtcaatg aaatcaagac attttggtag   16320
tgattggaaa tccatattta cttggggtgc aagagtcaaa ggataataac atggtgtgtc   16380
agctcaaaat atacttcttc ttatctagtc tgaaaaagtt agtgaaagaa gctctgaaag   16440
aatctcaact tccaactgtc atggacttca gaaaattctc tcggaactat caactctaca   16500
aatctgtttc tcttccatca cttgaccag cctcagccaa aatagaaggg aatcttatat    16560
ttgatccaaa taactacctt cctaaagaaa gcatgctgaa aactaccctc actgcctttg   16620
gatttgcttc agctgacctc atcgaggtaa gtgtgaagag tttgaggttc tctagcccat   16680
tttgtacagc atcataaaca gagagtccct gggagccagg agctacccag aggaaaacta   16740
agaaccacca ggcacttcct accatgattc tgaggctttc ttctttccct ccttccccgc   16800
cttcctctct ccccgctagg ggtcacctga agcatgactt cttaacatta atagaaatgc   16860
aggcctggcg aggtggctca ctcctgtaat cccagcactt ggggaggccg aggcgggtgg   16920
atcatgaggt caggatatcg acaccatcct ggctaacacg gtgaaagccc atctctacta   16980
aaaatacaaa aaattagccg ggcgtggtgg caggcacctg tagtcccagc tacttgggag   17040
gatgaggcag gagaatggcg tgaacccagg aggctgagct tgcagtgagc cgagagattg   17100
cgccactgcg ctccagcctg ggcgacagag caagactcca tctcaaaaaa aaaaaaaaa    17160 aaaaaaattg aaatgcaaat gtctcgtctt taagtcccaa agccaaggaa gcatatgtgc   17220
tgcctagtca gatctgcttc aaatctcaaa tcactcccaa ctctgaatcc tttgttgaat   17280
tatttgtcct atctgaacct tagctgcctc ttctagaaaa aagcaagtaa taaggtcaag   17340
attctagtga gattttaata aagcagctcc tgtgaaatgc taaggtcagc tcctggcctg   17400
tggtattcaa atacttgttt agataaatgg acatcaagag tggggactac taggctggca   17460
tacaacaaag aaacctgatg ccatttctt gtctgatttt ctttctcaga ttggcttgga    17520
aggaaaaggc tttgagccaa cattggaagc tcttttgggg aagcaaggat ttttcccaga   17580
cagtgtcaac aaagctttgt actgggttaa tggtcaagtt cctgatggtg tctctaaggt   17640
cttagtggac cactttggct ataccaaaga tgataaacat gagcaggtgt gtatttgtga   17700
agtatcttct taaggaaagc tttgggtctc aatgcaaaaa caattctttt ctaagcatgg   17760
aagtcctcaa aatactatct aactgaaggg ataactatgg tttttatcaa ccagacctgc   17820
tggggtaagg gccagtatcc tctgcagtta agatctcct gaattcagtg tgcccagaaa    17880
ccagactcac aataagtact ctaggataac aagagtatga actctgggct gggtgtggtg   17940
gttcatgcct gtaatcccag cactttggga ggccaaggtg gcagatcac aaggtcagga    18000 atttgagacc agcctggcca acatactgaa accccgtctc tactaaaaat acaaaaaac    18060 tagctgggca tggtagtggg tgcctgtaat cctagctact cgggaggctg agacaggaga   18120
```

```
attgcttgaa cccgggaggt ggaggttgca gtgagccgag atcacgccgt tacactccag   18180
cccgggtgac agtgtgagac tgtatcttaa aaaaaaaaaa agtatgaact ctgggcatag   18240
atttaattct aacttccctg tcttgaagct gtgcgcactt ggggaagttg gttgatatta   18300
tgtgtatctg tttctgtctg tatcccagac tactaataac agtccaaacc tcacaaggtt   18360
atttaaagac aatgaaataa ggcatctaaa atgccaagca cagtgcctga tgctggcatt   18420
ggttgttcaa taagcagaca ctattacgag ttctaaatta atattttcat tattattaac   18480
tgctgtcttt ggctctcact cccatcagtg cactagcaaa tgagaccaaa cttccacttt   18540
gaagctagca atgagccccc atttaaggag ggaaataggt tgtatgatct ggagcttatt   18600
cttgaatttt ttgctaccca aagtgtggtc tggtcagaaa tacagcttct catgcttcac   18660
ccacaatcta ctgaatcaga agcgcatttt agcaagacct catgtgactt gtatgcacat   18720
tcaactttgc agagcaaggc agtaatttac ccctccaggc tcactgttga gcacgagctc   18780
catcttctaa tttcctgacc cccacttgag gccgaggatc tttgatctgc tttgagtctg   18840
tcagtttcac atttttttttt tcccaatgcc tgggcatcca tctctgagat tcttcttctc   18900
tctgagaaga acttgtctag gatcaagtgt ttttcaaact tctggtgaat ttatataaca   18960
gctacatttt cttaagaaac accttgtagt cttcactggt caaagaagag aaggctaagc   19020
agggaacggg tgggggatag aggatcttct aatcttgagg atcctggcat actggagaat   19080
agggacccct cctctcatcc caccacatct tactatgtct acagattttt taattaagaa   19140
tagctttagg agtgccacta tccctgacaa gaccttagtt cttttaatctc tgcttagagg   19200 aattagcctg gacttcagtg tctccctgtt cctcacctgg agcattttt aggcccatcc   19260 tggctgcatc agacaggtcc cacattggga actgaaaggt gtttgacatt gctgacatct   19320
cactggccat tttattacta aactctcagg atatggtaaa tggaataatg ctcagtgttg   19380
agaagctgat taaagatttg aaatccaaag aagtcccgga agccagagcc tacctccgca   19440
tcttgggaga ggagcttggt tttgccagtc tccatgacct ccagctcctg ggaaagctgc   19500
ttctgatggg tgcccgcact ctgcagggga tcccccagat ggtaagtcag caggccccac   19560
tgggggccca tgagaccaga cgttggtttt ttttagatc gcccagactc ccttacgatc   19620
ccagctgcac aagcccgaaa agatgcttgt actttcttca gagatggagg tttgccttga   19680
atttcactga agatgactct tggatcacat ggaaatgtta acatttagaa attaagctat   19740
tcataatgtt agctgtattt ttaagagcat taatttattc atctggaaaa caatgttcgg   19800
tataccttcc tctacctttg ctgaaggtcc tttattttt attttattt ttttaatttt   19860 ttgagatgga gtcttgctcc caggctggag tgcagtgata caatctcggc tcactgcaac   19920
tctgccttcc gggttcaagc aattctcctg cctcagcctc ccaagtagct gggactgtgg   19980
acgtgcacca gcatgcccgg ctaatttgtg tatctttagt agagacaagc ctgttgacaa   20040
ccatgtcagg ctggtttcga actcctgacc tcaagtgatc ctccagcctg ggcctcccac   20100
agtgctggaa taacaggtgt gagccactgc acctgacctg aaggtccttt taagattgaa   20160
atgatacaat gattataaaa gaaagtattt ggcaaactat aattcactat ctaaatatgc   20220
tataattttt attattaatt cataaaagga aatatataaa tgtactccta tggcttgatt   20280
aaaaaaatgt tgactttaag aaaacaggtc tcaagctatt ttattgaaat attatttaaa   20340
aaataaaacc caatgcaaat tgatatgtac atcatctcaa taggcctttg gtttcaaaaa   20400
attgatttta tcataatata atacattttca agtacacctt cacttacagt cagactccag   20460
```

```
aacaccagaa ttaagccatg gcatatatga tacttaaagt ccataaagct ctgaggccca    20520
gcaatattct taagagcctt ctgagtccac ttgaaaatga catgatatct atctagtgaa    20580
atttcttata tcctgattca ctgaaaacgg taaaaacatc agtttgatct ttatttatca    20640
aactattcag ctcatcaaaa tatgctagtc cttcctttcc agataaagag gaattactct    20700
ccaatgtatg ggaggttgta attaacaaaa ccgactttaa aaagacttac ttttatttgc    20760
tctcccttgt tgggtctaca gattggagag gtcatcagga agggctcaaa gaatgacttt    20820
tttcttcact acatcttcat ggagaatgcc tttgaactcc ccactggagc tggattacag    20880
ttgcaaatat cttcatctgg agtcattgct cccggagcca aggctggagt aaaactggaa    20940
gtagccaacg taagattctg tttgcctttt gatttcttag gttattactt tcttccaggg    21000
tgcatttctt gttaaaacat atttaaaaat gtgtttccac ttcaagacaa aatgcttcat    21060
cattgtaatc acctcattat tttttatga aaaacttcaa gcttccacca gaatgcacta    21120
cctcactagc tccagtagtg gtatggccat aagacaagaa ctcagttctc tcaacaaatg    21180
agtattccta tcatcttttt aatctggttt tgcctcacgt taactcaggt gctttctagt    21240
tctgggtagt atactccaac tctagagaac tgagaactcg ctttccttct tccaaacaaa    21300
tcccagtaat gtttccaaag gtctgagtta tccaggaaat ctttgcccgg aggtgagaaa    21360
gggtggttga tctgactgac aggggactga agtatttaat gaatctgaat aggttgtttt    21420
ctgacttata gatgcaggct gaactggtgg caaaaccctc cgtgtctgtg gagtttgtga    21480
caaatatggg catcatcatt ccggacttcg ctaggagtgg ggtccagatg aacaccaact    21540
tcttccacga gtcgggtctg gaggctcatg ttgccctaaa agctgggaag ctgaagttta    21600
tcattccttc cccaaagaga ccagtcaagc tgctcagtgg agggtaattc tttcagccaa    21660
gtctgcctag ccagtttgaa agagagaaca gagaatgtac ctgcagaatt ttgccaggct    21720
aaacagttga ttgagatcat tcaggtcctg aggaagcagg agaggagtag aaaggaaaga    21780
ttccgggtta cctattttaa ttctagccta gacttactac ataactacat aattacctt    21840 cttctacttt tcacatttta ctaaactgtc ctttatcttt ctgctttgag acttattaag    21900
acctactgct taattagttt ttattaagtt gtgattttt gttatctatt tgttttgaga    21960
atgaagaaac aatagctctg gagagatcat ctttggaaaa ttaatatttt ccccccaaa    22020 aaatacctaa gaacatattg atttgaggta gctaggtagg taaagcatga aactcctaac    22080
ctcgtgataa tggaatacag cctcttttgg agagttccat tttaagtggc accctcaacc    22140
attgatttgc cttagttttc atattttaga cacattcatg tgttcattca aaaataaat    22200 ttaattggcc agccacggtg gttcatgcct gtaatcctag cactttggga gccccaggtg    22260
gatggatcgc ttgagccctg gtgtttggat accagcctgg gcaacatggc aaaaccccat    22320
ctctacaaaa aaaattaaat aaataacaaa attagccagt cgtggtggca catgcctgta    22380
gctccagcta ctcagaaggc tgagatggga ggatcaactg agcccaagag ttcaagcctt    22440
cagtgaacca tgcttgcacc actgcactcc agcctgggag acagagcaag atcctgtctc    22500
acaaaaaaca aaaatagta tatttaattg cctaatatat accacgtatg ttgagtgaga    22560
cacacaaggt ccctgacctt tgaacgctta cattttataa gggagacaca caattaagca    22620
agcagtaatc atagagtaag ggctaagtta tagaaagtat tagagtacca tgaaattta    22680 tatcatgtag cctgtgctag tcagggaatg cattctgaag caagtgtact tgacctgata    22740
actgaggact gtgtcagagt catttaggca aaggagaaag gagtgagtgt tccaggcaaa    22800
aggaaaagca tgtaatggcc tgaaggtaaa ggaatatggt tcaaggaact ggaagaagtg    22860
```

```
cagaatggta aggggctcag agatgatggg gagaggtagg caggggagag agcatgccca   22920
gctgcgaaag ccatcctaag gagtttggac tcttttgaag gcacaggagt tgaaaagggg   22980
agcagaaata agatagggt gatgttttag aagaaatact ctgactctag tgtggaagat    23040
```

```
cagaatggta aggggctcag agatgatggg gagaggtagg caggggagag agcatgccca   22920
gctgcgaaag ccatcctaag gagtttggac tcttttgaag gcacaggagt tgaaaagggg   22980
agcagaaata agatagggt gatgttttag aagaaatact ctgactctag tgtggaagat    23040
gggtgagaag gaggcacagc tggacacgaa gagaccattg acatctctt acgatcctat    23100 gtggctaaga gctgataatg gcctgcagtg gagaaaagcc aggtatagaa aggagtgagc    23160
agattctaca actttctaag aggcagaatc ataagtactg ggtgattaac tgggtatggg    23220
gacaaggcaa agaaagaag aaaagaggaa ggaggcgccc ttcattttaa taagaactac    23280
agtgggagag cttctggttt caaggaaagt gacaaattca gttttggatg tgctgtattt    23340
gatgtcctcc tatgaaacaa ccagtttaga aatctagctg tcaaatagac ctatggatct    23400
gagcccagta aagaggcttg ggctccacat atggatttgg gaatcattag tatacagagg    23460
ttgttgtggt taaacagcaa ctggtataga gtgagacatg agagatgagg acagaaatat    23520
ggagaagaca aacatataaa ggaagaaggg gaataaccag caatgagtta gaagaagtga    23580
ccagagaagc agaaggagaa ccaaagccat aaaaggtcac agaagccaaa gagcagccac    23640
aggggagatc accccatggg taggcgaaag ctggcattag gactccagca catcagcaaa    23700
gcttggtctt gtggcacccc caacttggag aaacaatact tggaggaaaa tgtgctatttt   23760 caaagaaagc atccttagaa aaaccaggc caatgttgaa cttttcttaca tgtactaagt    23820 ttttaagtac acacttggaa ggaaggtgcc atcatctctt cagatgtgag aggctccagc    23880
gtcttagtct ggtcatgagt gcgcaactct atggaaggct tctgggaggt caaggaagat    23940
gaaacctaaa tatgcccatt ggatgtagga gcaaggaggg cattagagac attgatgaaa    24000
gcattttcag gagatggagt gagcagtcag agcacattgg gaggaagtag agactgcaaa    24060
ggcagacaac tcttgatggt gaggaagatg agaaagcaag aaaagaaaga aaggagcata    24120 ggggagggc acaggggaag agacttgagc gtgcttaatg caggtggaag gaagcaggta    24180
gagagtagga gatttcatat gaaagagaca gtttctcttg ccctgcattg taggaaggaa    24240
ggggcacact gaagttcagc cccagtgatc agctatttaa catctctgag cctctgcttc    24300
tgtaaaatga gaaccataag cctactgttg tggggattac aggtaacaga tggaaagaac    24360
tcagccagaa gcttcagagt cactctcatg gcttgtcatg ttgatgttct ttctaatatt    24420
atttgtttct cagtaaatta aatagttaga gataggtgtg gactgaggga agacaggagg    24480 ataaggggt atttgcaccc tgagaatttg tgatgtccat tttgattcat gacttggcaa    24540
taactcaggt attttttgttc ttcaccagca acacattaca tttggtctct accaccaaaa    24600
cggaggtgat cccacctctc attgagaaca ggcagtcctg gtcagtttgc aagcaagtct    24660
ttcctggcct gaattactgc acctcaggcg cttactccaa cgccagctcc acagactccg    24720
cctcctacta tccgctgacc ggggacacca ggttagagat gctcagtgcc tgacccagca    24780
ttttctcacc ttccacatca tggccaccta gcatggcaca ggaaaaaata ctctgtgttg    24840
taagaccctg tcactagcct tctgggtttg caccatcttt gggtatttaa agcagggtcc    24900
tctggccaac acattgggtg tcaccttttg cttccttgtg catgggatgg gatcacagca    24960
cagatcccaa tttgctccta attcagtgtc catgtttctg agcctccaga cccatcgcta    25020
tgagcttcct ggagcccacc aatgtgcttg aagccttcac cgtacttagg tggctccctg    25080
tcttcagccc ccaagttcca gtgcttgttc tcagcttttgc tgaaacaacc agccaactcc    25140
tgctctgctt gtccaaagtc ttgggaatcc tggtgtctgc ccttgccttg ggttcttgta    25200
```

```
ggactgaggg atcaaaaaga tcatcttagt taagggcaag agacaatgtt aaaataagga    25260 ccatatttt  gttgcatttg aggctgaatt gttttgggaa cataatcacc atccttgaaa    25320
gctctaacat tatgcactgt cttcattgta atgtctttag attagagctg gaactgaggc    25380
ctacaggaga gattgagcag tattctgtca gcgcaaccta tgagctccag agagaggaca    25440
gagccttggt ggatacccctg aagtttgtaa ctcaagcaga aggtgagtat tcaaaacaca   25500
gctgcctcat ctctgctcgc agtctccaggt tcagaattca tgaggagaag acatgtaatt   25560
taacctattt aacaaatagg ttaactgagt acccactaag cggcaggcct attctaagac    25620
ctgggttaac tgagtaccca ataagcggca ggcctattct aagacctggg gctagaacag    25680
tgaacaatgg agtctctgcc ttcatggaag ttacagtgaa caaccaaaca agttaatatt    25740
tggaatatca gataagtact gaggaggaaa acagagcgta gactggtcta tggagggcta    25800
ggagtaggag ggaggaagaa gggcagggaa agcagtgcat ttggaataat aagggaaagt   25860
ctccctggta aagtgagcat aaggagacct atcagaaata agaggagaag ccgtgtggta   25920
agactgttaa caggcagagg gaccagcaag tgcaaaggcc ctgaggctga cacactacta   25980
ccatgtttca aggaaaggaa ggaagacagt atggctggag cagaaagacc agggagaaaa   26040
gaggtagaag atgaggacag agagatatgg agaggtgaag gaaggataat ctcataggcc   26100
atggtaagaa cttggctttt ttctatgaat taaacgaaag ccattgggga gtcctcatga   26160 tttgattat gtttatgttg agaaaagact atgggcagac aagggcagag aaactaatat     26220
gtaggttatc acaataatcc aggcaggaat cagtgttgtt ttggatcagg gcaatggcag    26280
aagagatatg agaaggggat ggattctggc catattttga agattaggct gacaagattt    26340
gctgatacag tggatgttga gtgtaagagg aaaagggaa tgaagacaaa cctaaggttt    26400
ttggcccggg caactgaaaa atggaacttc catttattga gatggaaagg gctactggag    26460
gagcaggttt tagggaatgg gagaaattta ggtgttcact ttggaaaaaa aattatatag    26520
ggatagcgag gagcaggttt tagggaatgg ggcacattta ggtgttcact ttggaaaaat    26580
ttttatatag ggatagcata tcacagaatt aaactaggaa gaaaatccca tgatagaaag    26640
cactggagga gcaggcacg  ctggggaaat agtgtttggt aaacattgtt ttacgaagga    26700
tataaaatgg accagcctat ggattgaagg acgcccggga atcttgttac aaagaaaggg    26760
ggagttgggg agatggagcc cagggcaagg gcagcaagga accaggacag gcatcttggg   26820
tagaaagtaa tatagagatg tcgtgtcttc ctggcccaga agggctgcga gcctttgctg    26880
ttccacaaac aagctaagtg ctccccattt cagggccttt gcattcctga ccttctgcct    26940
ggaatgtgct cctcccagaa ctcagcgtgg ctccaacctc ttttcattct ggtctctgcc    27000
cacatgtgcc cttatcagag agaatttctc tgaccaccaa gtatgaaata acacttcttc    27060
tatccctttc ttttatcctt gtatccagtt ttactcttct tcataacatt cattaccatc    27120
tgacatgagc aagttacttg tttattgcct gtacacctcc cccactagaa ggtaagcccc    27180
atgaaagcaa ggattcccca gtaccaagag cagtgcccag cacacaatag gctcataaca    27240
ggcaatccat aaagacttgc atacatgaac acaactgagt ttaaaattat cagtaaatga    27300
gacccattaa aaaattttaa tgagaaaaaa aaattcagt aaaatcctga actgtgtttt      27360
tgtttaagca cattgattcc ttggagtttc tctacctttt cctctctttc cttccaaaac     27420
atagcttctt tatttattta tttatttatt tgtttgttta tttatttatt tatttattta      27480
tttatttttt gagatggagt ctcgctcttt tgcccaggct gcagtgcagt ggtgccatct     27540
cggctcactg caagccccgc ctcccgggtt catgccattc tcctgcctca gcctcctgag    27600
```

```
tagctgggac tacaggcacc caccaacgcg cccggctaat ttttgtatt tttagtagag   27660 acggggtttc accatgttag ccagaatggt cttgatctcc tgacctcatg atctgcccgc   27720
cttggcctcc caaagtgctg ggattacagg tgtgagccac cgcacccggc ccaaaacata   27780
gcttcttacc acacatctct tgattctctt atacactcgt ccaggtgcga agcagactga   27840
ggctaccatg acattcaaat ataatcggca gagtatgacc ttgtccagtg aagtccaaat   27900
tccggatttt gatgttgacc tcggaacaat cctcagagtt aatgatgaat ctactgaggg   27960
caaaacgtct tacagactca ccctggacat tcagaacaag aaaattactg aggtcgccct   28020
catgggccac ctaaggtaaa gaaggccgag ggtcatctga cctgcactgc aggcctgggt   28080
ggttcttttc attattcctc ttccacttca tacctgacca agccatgttc tccctagtc    28140 tacaatcaga gtggcagaga gagccctcaa caatttttt tttttttgag atggagtctc   28200
actctgtcac caggctggag tgcagtggca caatctcggc tcactgcaac ctccgcctcc   28260
cgagttcaag tgattctcct gcttaagcct cccaaggagc tggaactata ggtgcatgcc   28320
accacaccca gctaattttt atattttag tagagacagg gtttcaccat attgaccagg    28380
atggtctcga tctcctgacc tcgtgatcca cctgccttgg cctcccaaag tgctgggatt   28440
acaggtgtaa gccactgcac ccggccaagc tctcaacatt ttaaccctct gcgcatgtcc   28500
agttggattt tcctaccatt tatcaggcac ttactattca tgtatcaagc acagtgctgg   28560
gtgctttaaa gaaattatct cggtcctcac aataaactgc gaggtcactg tgagttttcc   28620
tgtttcatgg ataaggaaat ggtagctcag aggggttaaa tcatttggtc aaaatcacag   28680
agctagtaaa tagcagagca ggattcaaac agttttcaaa aaacttctct ttctcctaaa   28740 cctgttgca aagtccttaa tttgtgctga atgttggctt tagaagttga tgagtttgat    28800
ctgtggctgt ttctctgaac catccttgta tctggttttg atcaccacaa atggaacttc   28860
tgtttaatcc tgcatatctc cattgaaagg acaaaatcat tggtgccaac tgattttctt   28920
taccatagtt gtgacacaaa ggaagaaaga aaatcaagg gtgttatttc catacccgt    28980 ttgcaagcag aagccagaag tgagatcctc gcccactggt cgcctgccaa actgcttctc   29040
caaatggact catctgctac agcttatggc tccacagttt ccaagagggt ggcatggcat   29100
tatggtatgt gtctcttccc ctgtgtgagc acttccaaag taatgcaggt gttgagacct   29160
gtggttacag gctgaactag taccattcac aactatttcc tacgtatttt cagatgaaga   29220
gaagattgaa tttgaatgga acacaggcac caatgtagat accaaaaaaa tgacttccaa   29280
tttccctgtg gatctctccg attatcctaa gagcttgcat atgtatgcta atagactcct   29340
ggatcacaga gtccctcaaa cagacatgac tttccggcac gtgggttcca aattaatagt   29400
tgtaagtatg agtctgccag tcaataaata catggatata agtgctaatt acatcctcaa   29460
ctctgagcta ggtgcaggaa ggtttccaaa gatgtataag gcatgcttcc ttccccccag   29520
ggaattcttg gggagaaaaa aaaactttca caagtgtgta gttacccagt tacacaaagc   29580
tgaatgtgat acatatcaaa gagatgctac taagtagaac agttctttgc ctagtggtat   29640
caaaggaagc ttcaggacac cagctaggag gctgactatg ttagacattc cttttataaa   29700 tatgacagt gatcagtgac tggcaacgaa gattcataat tttctgttat ttatttttaa    29760
ctttcagtgc attgtccagc ttaataatta acttgtcaaa tcggtatttt tgcctaatgt   29820
tcattgctct ttgaggctca tccaagccca ttaccttaaa aatctcctgt cattttgtag   29880
gcaatgagct catggcttca gaaggcatct gggagtcttc cttatacccca gactttgcaa   29940
```

```
gaccacctca atagcctgaa ggagttcaac ctccagaaca tgggattgcc agacttccac   30000
atcccagaaa acctcttctt aaaaaggtaa aagaagaaag cagcaaggct tcttgaacca   30060
tgcaaagtaa atgaaagatt ttacatagca tgatttagac atttttttaa attttttaaag  30120 gaaataattt aagcatttta aggagattaa aactatagc acaaacactg tggcatcttt    30180
gcattagtaa acatgagaac accaaccctg tcaggaagaa tctaagaaag tcattagagg   30240
attctggtac tttcacccta agatatttta ttcagtacaa cctgttataa gcaaattctc   30300
cctctgactg tgaagaattc agaatggcta gaggcgttat tgactacagg cttgctgtta   30360
agctagagag agtcagaaca gccattgagc actaaatgga ggcagcattc tgagaaaata   30420
ctttaaccca ggcttactga cttccatacc tatgttcttt ccacaaatca agttgtctca   30480
attcagttta gcaaatttgt atcaagtatc ccctatgtgc aaaatgctag actaggtaca   30540
gtgagaagat agaaactggg taaggtatag ccttttcttt caagaagata ccatggagac   30600
atcaacaaat gagaaataat taattatata agcaaaatta tgcatgctc tttgagaaag    30660 gtgcaaggga ctatgtaact gtaagaatga acaaattgg ctatgactta ggtgggatgg    30720
taatgataag gagtggccct tagaagagct ttgtcaggat ttgagtgttt gacaggtgga   30780
ggtaaaagca aaggggtcca ggcataggag tagcacaaag aaaagtgcag agtggctttg   30840
ggaatggggc aagtacaata ttgttgtgaa ggtcagaggc agagaacttt gaatgactga   30900
tgtctgactg tggggatgtt atctttgttg ttcatttcag cgatggccgg gtcaaatata   30960
ccttgaacaa gaacagtttg aaaattgaga ttcctttgcc ttttggtggc aaatcctcca   31020
gagatctaaa gatgttagag actgttagga caccagccct ccacttcaag tctgtgggat   31080
tccatctgcc atctcgagag ttccaagtcc ctacttttac cattcccaag ttgtatcaac   31140
tgcaagtgcc tctcctgggt gttctagacc tctccacgaa tgtctacagc aacttgtaca   31200
actggtccgc ctcctacagt ggtggcaaca ccagcacaga ccatttcagc cttcgggctc   31260
gttaccacat gaaggctgac tctgtggttg acctgctttc ctacaatgtg caaggtgagc   31320
tatgctcagg taaagggtgc accgggctag ttcatggcag gctctaagag gagagcctcc   31380
tccagggagg aaaggacttt ggcttttctag cagataatct tccttgctac ttggaagtct   31440 tttatttat tcaacaaata gaaatattta ttaaacatat cacgtgtatt aaatattcta     31500
gtaggcagta acagaaagta gacagataag ccagcaatta taattcagtg tgagaggtgc   31560
tatgataaag tgtagtatat aagtataagg tagagtggaa gcactcaaca agggaaccta   31620
aacaaagcct gtggtggtca ggcaaggctt cctggaggaa tgccttttgc tatcagattt    31680
tatctttgca ttacagatgg aggagtctat tgcacaattg gcccagaaaa atgggctttt   31740
attattgaaa gactttcaac atagagattg ctctggaaat gtactgctta atttaaccaa   31800
tgtcttttca ttttatgtt aggatctgga gaaacaacat atgaccacaa gaatacgttc    31860
acactatcat atgatgggtc tctacgccac aaatttctag attcgaatat caaattcagt   31920
catgtagaaa aacttggaaa caacccagtc tcaaaaggtt tactaatatt cgatgcatct   31980
agttcctggg gaccacagat gtctgcttca gttcatttgg actccaaaaa gaaacagcat   32040
ttgtttgtca aagaagtcaa gattgatggg cagttcagag tctcttcgtt ctatgctaaa   32100
ggcacatatg gcctgtcttg tcagagggat cctaacactg gccggctcaa tggagagtcc   32160
aacctgaggt ttaactcctc ctacctccaa ggcaccaacc agataacagg aagatatgaa   32220 gatgggaaccc tctccctcac ctccacctct gatctgcaaa gtggcatcat taaaaatact   32280
gcttccctaa agtatgagaa ctacgagctg actttaaaat ctgacaccaa tgggaagtat   32340
```

```
aagaactttg ccacttctaa caagatggat atgaccttct ctaagcaaaa tgcactgctg    32400
cgttctgaat atcaggctga ttacgagtca ttgaggttct tcagcctgct ttctggatca    32460
ctaaattccc atggtcttga gttaaatgct gacatcttag gcactgacaa aattaatagt    32520
ggtgctcaca aggcgacact aaggattggc caagatggaa tatctaccag tgcaacgacc    32580
aacttgaagt gtagtctcct ggtgctggag aatgagctga atgcagagct tggcctctct    32640
ggggcatcta tgaaattaac aacaaatggc cgcttcaggg aacacaatgc aaaattcagt    32700
ctggatggga agccgccct cacagagcta tcactgggaa gtgcttatca ggccatgatt     32760
ctgggtgtcg acagcaaaaa cattttcaac ttcaaggtca gtcaagaagg acttaagctc    32820
tcaaatgaca tgatgggctc atatgctgaa atgaaatttg accacacaaa cagtctgaac    32880
attgcaggct tatcactgga cttctcttca aaacttgaca acatttacag ctctgacaag    32940
ttttataagc aaactgttaa tttacagcta cagccctatt ctctggtaac tactttaaac    33000
agtgacctga aatacaatgc tctggatctc accaacaatg ggaaactacg gctagaaccc    33060
ctgaagctgc atgtggctgg taacctaaaa ggagcctacc aaaataatga aataaaacac    33120
atctatgcca tctcttctgc tgccttatca gcaagctata aagcagacac tgttgctaag    33180
gttcagggtg tggagtttag ccatcggctc aacacagaca tcgctgggct ggcttcagcc    33240
attgacatga gcacaaacta taattcagac tcactgcatt tcagcaatgt cttccgttct    33300
gtaatggccc cgtttaccat gaccatcgat gcacatacaa atggcaatgg gaaactcgct    33360
ctctggggag aacatactgg gcagctgtat agcaaattcc tgttgaaagc agaacctctg    33420
gcatttactt tctctcatga ttacaaaggc tccacaagtc atcatctcgt gtctaggaaa    33480
agcatcagtg cagctcttga acacaaagtc agtgccctgc ttactccagc tgagcagaca    33540
ggcacctgga aactcaagac ccaatttaac aacaatgaat acagccagga cttggatgct    33600
tacaacacta aagataaaat tggcgtggag cttactggac gaactctggc tgacctaact    33660
ctactagact ccccaattaa agtgccactt ttactcagtg agcccatcaa tatcattgat    33720
gctttagaga tgagagatgc cgttgagaag ccccaagaat ttacaattgt tgcttttgta    33780
aagtatgata aaaaccaaga tgttcactcc attaacctcc cattttttga gaccttgcaa    33840
gaatattttg agaggaatcg acaaaccatt atagttgtac tggaaaacgt acagagaaac    33900
ctgaagcaca tcaatattga tcaatttgta agaaaatatca gagcagccct gggaaaactc    33960
ccacagcaag ctaatgatta tctgaattca ttcaattggg agagacaagt ttcacatgcc    34020
aaggagaaac tgactgctct cacaaaaaag tatagaatta cagaaaatga tatacaaatt    34080
gcattagatg atgccaaaat caactttaat gaaaaactat ctcaactgca gacatatatg    34140
atacaatttg atcagtatat taagatagt tatgatttac atgatttgaa atagctatt     34200 gctaatatta ttgatgaaat cattgaaaaa ttaaaaagtc ttgatgagca ctatcatatc    34260
cgtgtaaatt tagtaaaaac aatccatgat ctacatttgt ttattgaaaa tattgatttt    34320
aacaaaagtg gaagtagtac tgcatcctgg attcaaaatg tggatactaa gtaccaaatc    34380
agaatccaga tacaagaaaa actgcagcag cttaagagac acatacagaa tatagacatc    34440
cagcacctag ctggaaagtt aaaacaacac attgaggcta ttgatgttag agtgcttta    34500 gatcaattgg gaactacaat ttcatttgaa agaataaatg acattcttga gcatgtcaaa    34560
cactttgtta taaatcttat tggggatttt gaagtagctg agaaaatcaa tgccttcaga    34620
gccaaagtcc atgagttaat cgagaggtat gaagtagacc aacaaatcca ggttttaatg    34680
```

```
gataaattag tagagttggc ccaccaatac aagttgaagg agactattca gaagctaagc    34740
aatgtcctac aacaagttaa gataaaagat tactttgaga aattggttgg atttattgat    34800
gatgctgtca agaagcttaa tgaattatct tttaaaacat tcattgaaga tgttaacaaa    34860
ttccttgaca tgttgataaa gaaattaaag tcatttgatt accaccagtt tgtagatgaa    34920
accaatgaca aaatccgtga ggtgactcag agactcaatg gtgaaattca ggctctggaa    34980
ctaccacaaa aagctgaagc attaaaactg ttttttagagg aaaccaaggc cacagttgca    35040
gtgtatctgg aaagcctaca ggacaccaaa ataaccttaa tcatcaattg gttacaggag    35100
gctttaagtt cagcatcttt ggctcacatg aaggccaaat tccgagagac cctagaagat    35160
acacgagacc gaatgtatca aatggacatt cagcaggaac ttcaacgata cctgtctctg    35220
gtaggccagg tttatagcac acttgtcacc tacatttctg attggtggac tcttgctgct    35280 aagaaccctta ctgactttgc agagcaatat tctatccaag attgggctaa acgtatgaaa    35340
gcattggtag agcaagggtt cactgttcct gaaatcaaga ccatccttgg gaccatgcct    35400
gcctttgaag tcagtcttca ggctcttcag aaagctacct tccagacacc tgattttata    35460 gtcccccctaa cagatttgag gattccatca gttcagataa acttcaaaga cttaaaaaat    35520
ataaaaatcc catccaggtt ttccacacca gaatttacca tccttaacac cttccacatt    35580
ccttccttta caattgactt tgtagaaatg aaagtaaaga tcatcagaac cattgaccag    35640
atgctgaaca gtgagctgca gtggcccgtt ccagatatat atctcaggga tctgaaggtg    35700
gaggacattc ctctagcgag aatcacccctg ccagacttcc gtttaccaga aatcgcaatt    35760
ccagaattca taatcccaac tctcaacctt aatgattttc aagttcctga ccttcacata    35820
ccagaattcc agcttccccca catctcacac acaattgaag tacctacttt tggcaagcta    35880
tacagtattc tgaaaatcca atctcctctt ttcacattag atgcaaatgc tgacataggg    35940
aatggaacca cctcagcaaa cgaagcaggt atcgcagctt ccatcactgc caaaggagag    36000
tccaaattag aagttctcaa ttttgatttt caagcaaatg cacaactctc aaaccctaag    36060
attaatccgc tggctctgaa ggagtcagtg aagttctcca gcaagtacct gagaacggag    36120
catgggagtg aaatgctgtt ttttggaaat gctattgagg gaaaatcaaa cacagtggca    36180
agtttacaca cagaaaaaaa tacactggag cttagtaatg gagtgattgt caagataaac    36240
aatcagctta ccctggatag caacactaaa tacttccaca aattgaacat ccccaaactg    36300
gacttctcta gtcaggctga cctgcgcaac gagatcaaga cactgttgaa agctggccac    36360
atagcatgga cttcttctgg aaaagggtca tggaaatggg cctgccccag attctcagat    36420
gagggaacac atgaatcaca aattagtttc accatagaag gacccctcac ttcctttgga    36480
ctgtccaata agatcaatag caaacaccta agagtaaacc aaaacttggt ttatgaatct    36540
ggctccctca actttctaa acttgaaatt caatcacaag tcgattccca gcatgtgggc    36600
cacagtgttc taactgctaa aggcatggca ctgtttggag aagggaaggc agagtttact    36660 gggagggcatg atgctcattt aaatggaaag gttattggaa ctttgaaaaaa ttctctttttc    36720 ttttcagccc agccatttga gatcacggca tccacaaaca atgaagggaa tttgaaagtt    36780
cgttttccat taaggttaac agggaagata gacttcctga ataactatgc actgtttctg    36840
agtcccagtg cccagcaagc aagttggcaa gtaagtgcta ggttcaatca gtataagtac    36900
aaccaaaatt tctctgctgg aaacaacgag aacattatgg aggcccatgt aggaataaat    36960
ggagaagcaa atcggatttt cttaaacatt cctttaacaa ttcctgaaat gcgtctacct    37020
tacacaataa tcacaactcc tccactgaaa gatttctctc tatgggaaaa aacaggcttg    37080
```

```
aaggaattct tgaaaacgac aaagcaatca tttgatttaa gtgtaaaagc tcagtataag    37140
aaaaacaaac acaggcattc catcacaaat cctttggctg tgctttgtga gtttatcagt    37200
cagagcatca aatcctttga caggcatttt gaaaaaaaca gaaacaatgc attagatttt    37260
gtcaccaaat cctataatga aacaaaaatt aagtttgata agtacaaagc tgaaaaatct    37320
cacgacgagc tccccaggac ctttcaaatt cctggataca ctgttccagt tgtcaatgtt    37380
gaagtgtctc cattcaccat agagatgtcg gcattcggct atgtgttccc aaaagcagtc    37440
agcatgccta gtttctccat cctaggttct gacgtccgtg tgccttcata cacattaatc    37500
ctgccatcat tagagctgcc agtccttcat gtccctagaa atctcaagct ttctcttcca    37560
gatttcaagg aattgtgtac cataagccat attttattc ctgccatggg caatattacc    37620
tatgatttct cctttaaatc aagtgtcatc acactgaata ccaatgctga acttttaac    37680 cagtcagata ttgttgctca tctcctttct tcatcttcat ctgtcattga tgcactgcag    37740
tacaaattag agggcaccac aagattgaca agaaaaaggg gattgaagtt agccacagct    37800
ctgtctctga gcaacaaatt tgtggagggt agtcataaca gtactgtgag cttaaccacg    37860
aaaaatatgg aagtgtcagt ggcaacaacc acaaaagccc aaattccaat tttgagaatg    37920
aatttcaagc aagaacttaa tggaaatacc aagtcaaaac ctactgtctc ttcctccatg    37980
gaatttaagt atgatttcaa ttcttcaatg ctgtactcta ccgctaaagg agcagttgac    38040
cacaagctta gcttggaaag cctcacctct tacttttcca ttgagtcatc taccaaagga    38100
gatgtcaagg gttcggttct ttctcgggaa tattcaggaa ctattgctag tgaggccaac    38160
acttacttga attccaagag cacacggtct tcagtgaagc tgcagggcac ttccaaaatt    38220
gatgatatct ggaaccttga agtaaaagaa aattttgctg gagaagccac actccaacgc    38280
atatattccc tctgggagca cagtacgaaa aaccacttac agctagaggg cctcttttc    38340 accaacggag aacatacaag caaagccacc ctggaactct ctccatggca aatgtcagct    38400
cttgttcagg tccatgcaag tcagcccagt tccttccatg atttccctga ccttggccag    38460
gaagtggccc tgaatgctaa cactaagaac cagaagatca gatggaaaaa tgaagtccgg    38520
attcattctg ggtctttcca gagccaggtc gagctttcca atgaccaaga aaaggcacac    38580
cttgacattg caggatcctt agaaggacac ctaaggttcc tcaaaaatat catcctacca    38640
gtctatgaca agagcttatg ggatttccta agctggatg taaccaccag cattggtagg    38700
agacagcatc ttcgtgtttc aactgccttt gtgtacacca aaaacccaa tggctattca    38760 ttctccatcc ctgtaaaagt tttggctgat aaattcatta ttcctgggct gaaactaaat    38820
gatctaaatt cagttcttgt catgcctacg ttccatgtcc catttacaga tcttcaggtt    38880
ccatcgtgca aacttgactt cagagaaata caaatctata agaagctgag aacttcatca    38940
tttgccctca acctaccaac actccccgag gtaaaattcc ctgaagttga tgtgttaaca    39000
aaatattctc aaccagaaga ctccttgatt cccttttttg agataaccgt gcctgaatct    39060
cagttaactg tgtcccagtt cacgcttcca aaaagtgttt cagatggcat tgctgctttg    39120
gatctaaatg cagtagccaa caagatcgca gactttgagt tgcccaccat catcgtgcct    39180
gagcagacca ttgagattcc ctccattaag ttctctgtac ctgctggaat tgtcattcct    39240
tcctttcaag cactgactgc acgctttgag gtagactctc ccgtgtataa tgccacttgg    39300
agtgccagtt tgaaaaacaa agcagattat gttgaaacag tcctggattc cacatgcagc    39360
tcaaccgtac agttcctaga atatgaacta aatggtaaga aatatcctgc ctcctctcct    39420
```

```
agatactgta tattttcaat gagagttatg agtaaataat tatgtattta gttgtgagta    39480
gatgtacaat tactcaatgt cacaaaattt taagtaagaa aagagataca tgtatacccct   39540 acacgtaaaa accaaactgt agaaaatcta gtgtcattca agacaaacag ctttaaagaa    39600 aatgatttt tctgtaatta ttttaggact aacaatgtct tttaactatt tatttttaaaa   39660 taagtgtgag ctgtacattg catattttaa acacaagtga aatatctggt taggatagaa   39720
ttctcccagt tttcacaatg aaaacatcaa cgtcctactg ttatgaatct aataaaatac   39780
aaaatctctc ctatacagtt ttgggaacac acaaaatcga agatggtacg ttagcctcta   39840
agactaaagg aacatttgca caccgtgact tcagtgcaga atatgaagaa gatggcaaat   39900
atgaaggact tcagtatgga gcttttattg aattgaaacc ttataccttt tgaaaactca   39960
ttgtgatttt cttcatctcc atacccctt cgtgatagct catctgtttt tctgctttca    40020
gggaatggga aggaaaagcg cacctcaata tcaaaagccc agcgttcacc gatctccatc   40080
tgcgctacca gaaagacaag aaaggcatct ccacctcagc agcctcccca gccgtaggca   40140
ccgtgggcat ggatatggat gaagatgacg acttttctaa atggaacttc tactacagcc   40200
ctcaggtaaa taccacctaa tgagtgacac gcccccaaga gcgagtggag aattggggca   40260
gatacattta attcaggacc aaatattcag agattcccca aactaggtga agacaggcg    40320 gtaagcaact tcttctctga ggaaatattc tctagaaagt attacaatga gtccttgatt   40380 gatttaatg tttagatgca cacatgacat cccatcagca ctattattta ttaattctgg    40440
gcaaatccag gaagatgagg ttataccctc atcatctaaa tcataggcaa gctcagccat   40500
aggcagggta tatttttcag agaggactgg tttctgtagt atttaaaact ttaaaattct   40560
tccccacaat agaattgcta gatgagatac atcaaattcc tctcatgtca tttacaagct   40620
ctgccagggc caaatcaagg gtgacattac cagaggagaa gaccaaacat ggttctatga   40680
ctgttactaa aagtttgtca tgggcttgga gaatgcgtac tgatgttggg attctgggtc   40740
tctgcagggt gggctccaac ttgccttttt tgctatttct tcttttccta tctgtcattt   40800
cctgactctt cttctctctc ctcttctttc tcttcccccc actcctcttc cagttttcag   40860
tcctaggaag gctttaattt taagtgtcac aatgtaaatg acaaacagca agcgttttttg  40920 ttaaatcctt tctggggcat gtgataaaga gaaattaaca acagtagact tatttaacca   40980
taaaacaaac acatgaactg acatatgaaa gataaatccc tttcagtata tgaaagattc   41040
tctgatcttt attttaact gctaatgaag ttttagtgta ctatattgtg taattggagt    41100
aattgaaaac atgttatttt tttttttctc tctgtttagt cctctccaga taaaaaactc   41160
accatattca aaactgagtt gagggtccgg gaatctgatg aggaaactca gatcaaagtt   41220
aattgggaag aagaggcagc ttctggcttg ctaacctctc tgaaagacaa cgtgcccaag   41280
gccacagggg tcctttatga ttatgtcaac aagtaccact gggaacacac agggctcacc   41340
ctgagagaag tgtcttcaaa gctgagaaga aatctgcaga acaatgctga gtgggtttat   41400 caagggcca ttaggcaaat tgatgatatc gacgtgaggt tccagaaagc agccagtggc    41460
accactggga cctaccaaga gtggaaggac aaggcccaga atctgtacca ggaactgttg   41520
actcaggaag gccaagccag tttccaggga ctcaaggata acgtgtttga tggcttggta   41580
cgagttactc aagaattcca tatgaaagtc aagcatctga ttgactcact cattgatttt   41640
ctgaacttcc ccagattcca gttcccgggg aaacctggga tatacactag ggaggaactt   41700
tgcactatgt tcataaggga ggtagggacg gtactgtccc aggtatattc gaaagtccat   41760
aatggttcag aaatactgtt ttcctatttc caagacctag tgattacact tcctttcgag   41820
```

```
ttaaggaaac ataaactaat agatgtaatc tcgatgtata gggaactgtt gaaagattta    41880
tcaaaagaag cccaagaggt atttaaagcc attcagtctc tcaagaccac agaggtgcta    41940
cgtaatcttc aggacctttt acaattcatt ttccaactaa tagaagataa cattaaacag    42000
ctgaaagaga tgaaatttac ttatcttatt aattatatcc aagatgagat caacacaatc    42060
ttcagtgatt atatcccata tgttttaaa ttgttgaaag aaaacctatg ccttaatctt     42120
cataagttca atgaatttat tcaaaacgag cttcaggaag cttctcaaga gttacagcag    42180
atccatcaat acattatggc ccttcgtgaa gaatattttg atccaagtat agttggctgg    42240
acagtgaaat attatgaact tgaagaaaag atagtcagtc tgatcaagaa cctgttagtt    42300
gctcttaagg acttccattc tgaatatatt gtcagtgcct ctaactttac ttcccaactc    42360
tcaagtcaag ttgagcaatt tctgcacaga aatattcagg aatatcttag catccttacc    42420
gatccagatg gaaaagggaa agagaagatt gcagagcttt ctgccactgc tcaggaaata    42480
attaaaagcc aggccattgc gacgaagaaa ataatttctg attaccacca gcagtttaga    42540
tataaactgc aagatttttc agaccaactc tctgattact atgaaaaatt tattgctgaa    42600
tccaaaagat tgattgacct gtccattcaa aactaccaca catttctgat atacatcacg    42660
gagttactga aaaagctgca atcaaccaca gtcatgaacc cctacatgaa gcttgctcca    42720
ggagaactta ctatcatcct ctaattttt aaagaaatc ttcatttatt cttcttttcc      42780
aattgaactt tcacatagca cagaaaaaat tcaaactgcc tatattgata aaaccataca    42840
gtgagccagc cttgcagtag gcagtagact ataagcagaa gcacatatga actggacctg    42900
caccaaagct ggcaccaggg ctcggaaggt ctctgaactc agaaggatgg cattttttgc    42960
aagttaaaga aaatcaggat ctgagttatt ttgctaaact tggggagga ggaacaaata    43020 aatggagtct ttattgtgta tcataccact gaatgtggct catttgtatt gaaagacagt    43080
gaaacgaggg cattgataaa atgttctggc acagcaaaac ctctagaaca catagtgtga    43140
tttaagtaac agaataaaaa tggaaacgga gaaattatgg agggaaatat tttgcaaaaa    43200
tatttaaaaa gatgaggtaa ttgtgttttt ataattaaat attttataat taaaatatttt   43260 ataattaaaa tatttataat taaatatttt ataattaaaa tatttataat taaatatttt    43320
ataattaaag tatttataat taaatatttt ataattaaaa tatttataat taaatatttt    43380
ataattaaaa tatttataat taaatatttt ataattaaaa tatttataat taaatatttt    43440
ataat                                                                43445

<210> SEQ ID NO 9
<211> LENGTH: 568
<212> TYPE: DNA
<213> ORGANISM: H. sapiens
<220> FEATURE:
<221> NAME/KEY: misc_feature
<222> LOCATION: 44, 99, 156, 468
<223> OTHER INFORMATION: n = A,T,C or G

<400> SEQUENCE: 9
ccaaaagatt gattgactgt ccattcaaag ctacacgcaa tttntgatat acatcacgta      60
gttactgaaa aagctgcaat caacacagtt catggaccnc taccatgaag cttgctccag    120
gagaacttct atcattcctc taatttttta aaaganatct tcatttattc ttcttttcca    180
attgaacttt cacatagcac agaaaaaatt caaactgcct atattgataa aaccatacag    240
tgagccagcc ttgcagtagg cagtagacta taagcagaag cacatatgaa ctggacctgc    300
```

```
accaaagctg gcaccagggc tcggaaggtc tctgaactca gaaggatggc attttttgca      360
agttaaagaa aatcaggatc tgagttattt tgctaaactt ggggggaggag gaacaaataa      420 atggagtctt tattgtgtat cataccactg aatgtggctc atttgtanta aaagacagtg      480
aaacgagggc attgataaaa tgttctggca cagcaaaacc tctagaacac atagtgtgat      540
ttaagtaaca gaataaaaat ggaaacgg                                         568

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
gcctcagtct gcttcgcacc                                                   20

<210> SEQ ID NO 11
<211> LENGTH: 518
<212> TYPE: DNA
<213> ORGANISM: Mus musculus

<400> SEQUENCE: 11
cctgctcagt tttatcccta gaagcagcta gctactccag gtacgtaggt gccatgcagc       60
cccggacgct cctcactgtg gccctcttgg ctctcctggc atctgcccga gctgaagagg      120
tagagggatc cttgctgctg ggctctgtgc agggctacat ggaacaagcc tccaagacgg      180
tccaggatgc gctaagtagc gtgcaggagt ccgatatagc tgcggtggcc aggggctgga      240
tggacaatca cttcagattc ctgaaaggct actggagcaa gtttactgac aagttcaccg      300
gcttctggga ttctaacccct gaggaccaac caactccagc tattgagtcg tgagacttct      360
gtgttgcaga tgtgcctgtt cctccatcct gctgccccccc tccaggcctg ccaggtggcc      420
cctgaaggtt gctttaaggg gaaagtatgt tctcatgtct tcacccctcc ctagatctca      480
cctaaacatg ctgtccctaa taaagctgga taagaagc                              518

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
tcacgactca atagctggag                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
agacatgaga acatactttc                                                   20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 14
catgtttagg tgagatctag                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
tcttatccag ctttattagg                                              20
```